(12) United States Patent
Bauche et al.

(10) Patent No.: US 11,674,153 B2
(45) Date of Patent: Jun. 13, 2023

(54) VIRAL VECTOR CONSTRUCTS FOR EXPRESSION OF GENETIC ADJUVANTS ACTIVATING THE CD40 AND STING PATHWAYS

(71) Applicant: aratinga.bio AIO, Villejuif (FR)

(72) Inventors: Cécile Bauche, Paris (FR); Renaud Vaillant, Gentilly (FR); Emeline Sarry, Malakoff (FR); Frédéric Mourlane, Nice (FR)

( * ) Notice: Subject to any disclaimer, the term of this patent is extended or adjusted under 35 U.S.C. 154(b) by 983 days.

(21) Appl. No.: 16/464,496

(22) PCT Filed: Nov. 28, 2017

(86) PCT No.: PCT/IB2017/001553
§ 371 (c)(1),
(2) Date: May 28, 2019

(87) PCT Pub. No.: WO2018/096399
PCT Pub. Date: May 31, 2018

(65) Prior Publication Data
US 2020/0199620 A1 Jun. 25, 2020

Related U.S. Application Data

(60) Provisional application No. 62/426,860, filed on Nov. 28, 2016.

(51) Int. Cl.
| | | |
|---|---|---|
| *C12N 15/00* | (2006.01) | |
| *C12N 15/86* | (2006.01) | |
| *A61K 39/00* | (2006.01) | |
| *A61K 39/39* | (2006.01) | |
| *C12N 7/00* | (2006.01) | |
| *A61K 48/00* | (2006.01) | |

(52) U.S. Cl.
CPC .......... *C12N 15/86* (2013.01); *A61K 39/0011* (2013.01); *A61K 39/39* (2013.01); *C12N 7/00* (2013.01); *A61K 48/00* (2013.01); *A61K 2039/6031* (2013.01); *C12N 2710/16222* (2013.01); *C12N 2740/15043* (2013.01)

(58) Field of Classification Search
CPC ................................................ C12N 15/86
See application file for complete search history.

(56) References Cited

U.S. PATENT DOCUMENTS

| | | | | |
|---|---|---|---|---|
| 7,253,333 B2 * | 8/2007 | Tanaka | .................. | C07K 14/715 800/9 |
| 2005/0208078 A1 * | 9/2005 | Hoffman | .................. | A61P 33/06 424/272.1 |
| 2006/0094649 A1 * | 5/2006 | Keogh | ............. | C07K 14/70503 514/19.3 |
| 2013/0259833 A1 * | 10/2013 | Pan | ...................... | A61K 48/005 435/456 |
| 2015/0252080 A1 | 9/2015 | Stone et al. | | |

FOREIGN PATENT DOCUMENTS

| | | | | |
|---|---|---|---|---|
| WO | 2011/119628 A2 | 9/2011 | | |
| WO | WO-2014039961 A1 * | 3/2014 | ........... | A61K 39/245 |
| WO | 2017/100338 A1 | 6/2017 | | |

OTHER PUBLICATIONS

Zufferey et al (Journal of Virology vol. 72, No. 12, pp. 9873-9880) (Year: 1998).*
S. Gupta et al., "Constitutively Active MAVS Inhibits HIV-1 Replication via Type I Interferon Secretion and Induction of HIV-1 Restriction Factors", PLOS ONE, vol. 11, No. 2, Feb. 5, 2016, 25 pgs.
S. Gupta et al., "Latent Membrane Protein 1 as a molecular adjuvant for single-cycle lentiviral vaccines", Retrovirology, vol. 8, No. 1, May 18, 2011, 12 pgs.
F. Hou et al., "MAVS Forms Functional Prion-like Aggregates to Activate and Propagate Antiviral Innate Immune Response", Cell, vol. 146, No. 3, Jun. 21, 2011, pp. 448-461.
E.D. Tang et al., "MAVS Self-Association Mediates Antiviral Innate Immune Signaling", Journal of Virology, vol. 83, No. 8, Apr. 15, 2009, pp. 3420-3428.
U. Dirmeier et al., "Latent Membrane Protein Is Critical for Efficient Growth Transformation of Human B Cells by Epstein-Barr Virus", Cancer Research, Jun. 1, 2003, pp. 2982-2989.
A.G. Eliopoulos et al., "LMP1 structure and signal transduction", Seminars in Cancer Biology, vol. 11, No. 6, Dec. 1, 2001, pp. 435-444.

* cited by examiner

*Primary Examiner* — Albert M Navarro
(74) *Attorney, Agent, or Firm* — Verrill Dana, LLP

(57) ABSTRACT

Viral vectors are provided for use as genetic immunotherapeutic agents, including preventive and therapeutic vaccines as well as compositions to enhance cellular immune responses and innate immune responses. The vectors are particularly useful for treating or preventing cancer and infectious diseases. The vectors include lentiviral vectors that encode one or more antigens, a combination of adjuvants, and optionally may encode one or more soluble and secreted checkpoint inhibitor molecules. The adjuvants include latent membrane protein 1 (LMP1) from Epstein Barr virus and a fusion protein including LMP1 with in which the intracytoplasmic domain has been replaced by human IPS1 or a variant thereof capable of activating the STING pathway. The vector-encoded sequences are codon optimized for human expression.

10 Claims, 23 Drawing Sheets
Specification includes a Sequence Listing.

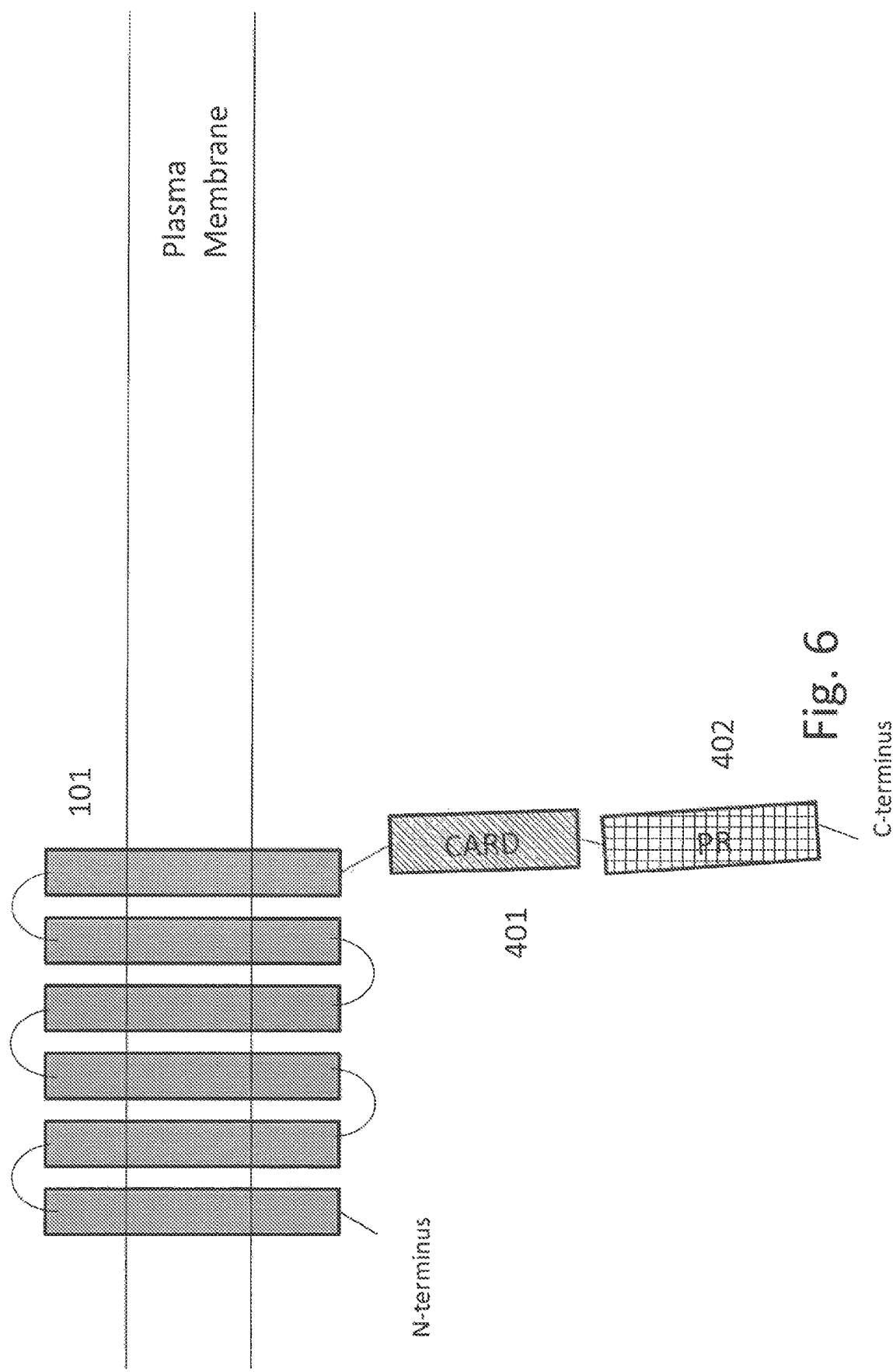

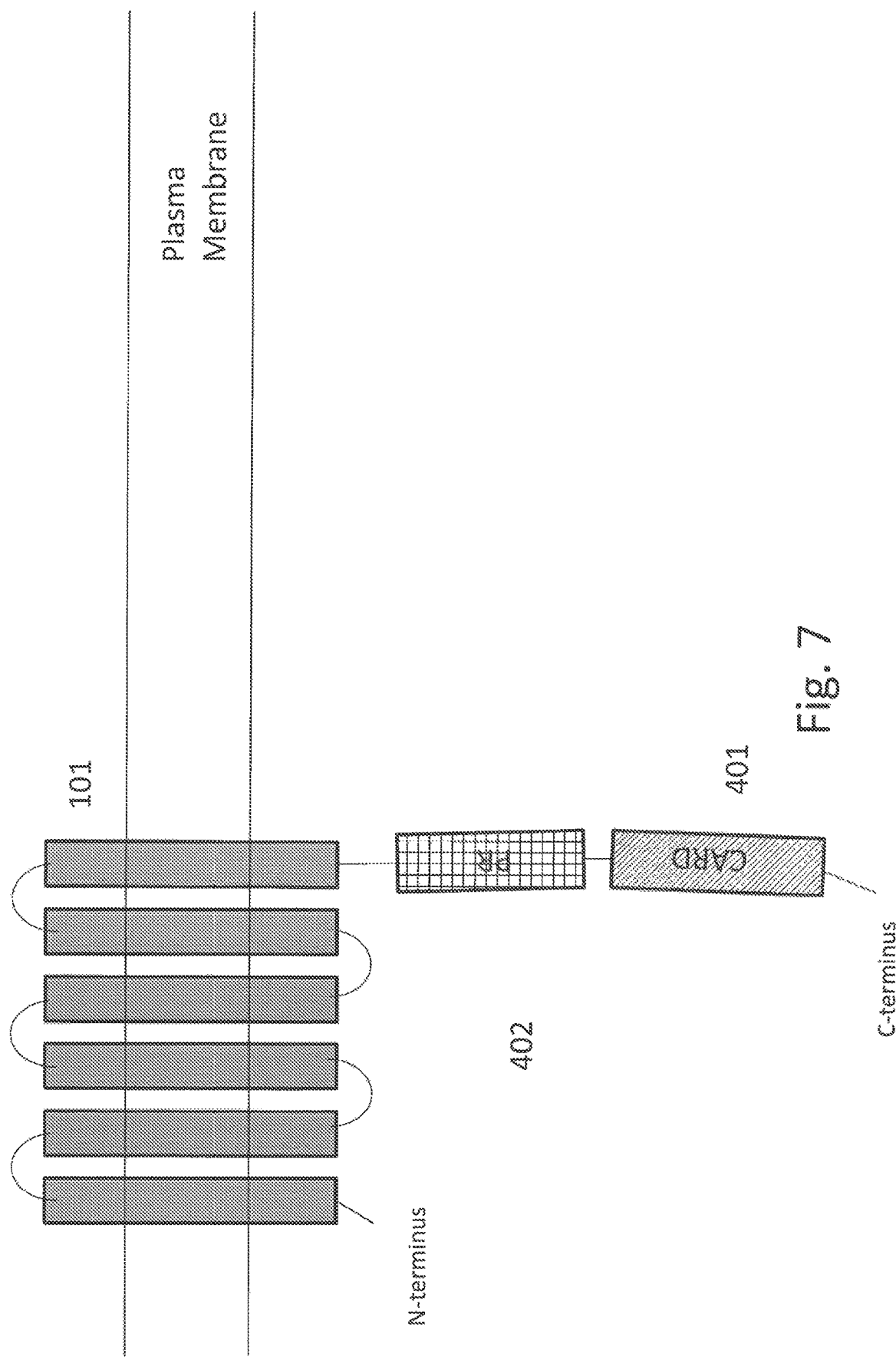

SEQUENCE LISTING

<160> NUMBER OF SEQ ID NOS: 24

<210> SEQ ID NO 1
<211> LENGTH: 1158
<212> TYPE: DNA
<213> ORGANISM: Epstein Barr virus

<400> SEQUENCE: 1

```
atggatctgg acctggaaag aggacctcct ggacctagac ggcctcctag aggaccacct      60
ctgagcagct ctattggact ggccctgctg ctgcttctgc tggctctgct gttctggctg     120
tacatcatca tgagcaactg gaccggcgga gcactgctgg tgctgtatgc ctttgctctg     180
atgctggtca tcatcatcct gatcatcttc atcttccggc gggacctgct gtgtcctctg     240
ggagcacttt gtctgttgct gctgatgatc accctcctgc tgatcgccct gtggaacctg     300
catggacagg ccctgtatct gggaatcgtg ctgttcatct tcggctgcct gctggttctc     360
ggcctgtgga tctacctgct ggaaatcctt tggagactgg cgccaccat ctggcagctg     420
ctggcctttt tcctggcctt ctttctggat atcatcctcc tcatcattgc cctgtacctg     480
cagcagaact ggtggaccct gctggtggat ctgctttggc tgctgctctt tctggccatc     540
ctgatttgga tgtactacca cggccagcgg cacagcgacg aacaccacca tgatgacagc     600
ctgcctcatc ctcagcaggc caccgacgat agcagcaacc agagcgacag caacagcaac     660
gagggcagac atctgctgct ggtgtctggt gctggcgacg acctcctct gtgttctcaa     720
aatcttggcg cccctggcgg cggaccaaac aatggacctc aggaccccga caacaccgac     780
gacaatggcc ctcaagatcc tgataatacc gatgacaacg cccacacga ccctctgcct     840
caagacccag ataacacaga cgataacggt ccacaagatc cggacaatac tgacgataat     900
ggaccccacg atccactgcc tcacaaccct agcgatagcg ccggaaatga tggcggacct     960
ccacagctga ccgaggaagt ggaaaacaaa ggcggagatc agggccctcc tctgatgacc    1020
gatggcggag gtggacactc tcacgattct ggccacgacg gcatcgaccc tcatctgcct    1080
acactgctgc tcggcacatc tggctctggc ggcgacgatg atgatcctca tggacctgtg    1140
cagctgagct actacgac                                                  1158
```

<210> SEQ ID NO 2
<211> LENGTH: 386
<212> TYPE: PRT
<213> ORGANISM: Epstein Barr virus

<400> SEQUENCE: 2

```
Met Asp Leu Asp Leu Glu Arg Gly Pro Pro Gly Pro Arg Arg Pro Pro
1

Ile Phe Gly Cys Leu Leu Val Leu Gly Leu Trp Ile Tyr Leu Leu Glu
            115                 120                 125

Ile Leu Trp Arg Leu Gly Ala Thr Ile Trp Gln Leu Leu Ala Phe Phe
        130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg His Ser
            180                 185                 190

Asp Glu His His His Asp Asp Ser Leu Pro His Pro Gln Gln Ala Thr
        195                 200                 205

Asp Asp Ser Ser Asn Gln Ser Asp Ser Asn Ser Glu Gly Arg His
210                 215                 220

Leu Leu Leu Val Ser Gly Ala Gly Asp Gly Pro Pro Leu Cys Ser Gln
225                 230                 235                 240

Asn Leu Gly Ala Pro Gly Gly Gly Pro Asn Asn Gly Pro Gln Asp Pro
                245                 250                 255

Asp Asn Thr Asp Asp Asn Gly Pro Gln Asp Pro Asp Asn Thr Asp Asp
            260                 265                 270

Asn Gly Pro His Asp Pro Leu Pro Gln Asp Pro Asp Asn Thr Asp Asp
        275                 280                 285

Asn Gly Pro Gln Asp Pro Asp Asn Thr Asp Asp Asn Gly Pro His Asp
    290                 295                 300

Pro Leu Pro His Asn Pro Ser Asp Ser Ala Gly Asn Asp Gly Gly Pro
305                 310                 315                 320

Pro Gln Leu Thr Glu Glu Val Glu Asn Lys Gly Asp Gln Gly Pro
                325                 330                 335

Pro Leu Met Thr Asp Gly Gly Gly Gly His Ser His Asp Ser Gly His
            340                 345                 350

Asp Gly Ile Asp Pro His Leu Pro Thr Leu Leu Gly Thr Ser Gly
        355                 360                 365

Ser Gly Gly Asp Asp Asp Pro His Gly Pro Val Gln Leu Ser Tyr
    370                 375                 380

Tyr Asp
385

<210> SEQ ID NO 3
<211> LENGTH: 570
<212> TYPE: DNA
<213> ORGANISM: Epstein Barr virus

<400> SEQUENCE: 3
atggatctgg atctcgaaag aggacctcct ggacctagac ggcctcctag aggaccacct     60
ctgagcagct ctattggact ggccctgctg ctgcttctgc tggctctgct gttctggctg    120
tacatcatca tgagcaactg gaccggcgga gcactgctgg tgctgtatgc ctttgctctg    180
atgctggtca tcatcatcct gatcatcttc atcttccggc gggacctgct gtgtcctctg    240
ggagcacttt gtctgttgct gctgatgatc accctcctgc tgatcgccct gtggaacctg    300
catggacagg ccctgtatct gggcatcgtg ctgttcatct tcggctgcct gctggttctc    360
ggcctgtgga tctaccctgct ggaaatcctt tggagactgg cgccaccat ctggcagctg    420 ctggcctttt tcctggcctt ctttctggat atcatcctcc tcatcattgc cctgtacctg    480

```
cagcagaact ggtggaccct gctggtggat ctgctttggc tgctgctctt tctggccatc    540
ctgatttgga tgtactacca cggccagcgg                                     570

<210> SEQ ID NO 4
<211> LENGTH: 190
<212> TYPE: PRT
<213> ORGANISM: Epstein Barr virus

<400> SEQUENCE: 4

Met Asp Leu Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
            20                  25                  30

Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
    50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
    130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg
            180                 185                 190

<210> SEQ ID NO 5
<211> LENGTH: 2187
<212> TYPE: DNA
<213> ORGANISM: Artificial sequence
<220> FEATURE:
<223> OTHER INFORMATION: Fusion of LMP-1 from Epstein Barr virus and
      ISP1 from Homo sapiens

<400> SEQUENCE: 5
atggatctgg atctcgaaag aggacctcct ggacctagac ggcctcctag aggaccacct    60
ctgagcagct ctattggact ggccctgctg ctgcttctgc tggctctgct gttctggctg   120
tacatcatca tgagcaactg gaccggcgga gcactgctgg tgctgtatgc ctttgctctg   180
atgctggtca tcatcatcct gatcatcttc atcttccggc gggacctgct gtgtcctctg   240
ggagcacttt gtctgttgct gctgatgatc accctcctgc tgatcgccct gtggaacctg   300
catggacagg ccctgtatct gggcatcgtg ctgttcatct tcggctgcct gctggttctc   360
ggcctgtgga tctacctgct ggaaatcctt tggagactgg gcgccaccat ctggcagctg   420
ctggcctttt tcctggcctt ctttctggat atcatcctcc tcatcattgc cctgtacctg   480
cagcagaact ggtggaccct gctggtggat ctgctttggc tgctgctctt tctggccatc   540
ctgatttgga tgtactacca cggccagcgg cctttcgccg aggacaagac ctacaagtac   600
```

-continued

```
atctgccgga acttcagcaa cttctgcaac gtggacgtgg tggaaattct gccctacctg    660
ccttgcctga ccgccagaga tcaggacaga ctgagagcca catgtaccct gagcggcaac    720
agagacacac tgtggcacct gttcaacacc ctgcagagaa ggcctggctg ggtcgagtac    780
tttatcgccg ctctgagagg ctgcgagctg gtcgatctgg ctgatgaagt ggccagcgtg    840
taccagagct accagcctag aaccagcgac cggcctcctg atcctctcga acctccatct    900
ctgcccgccg aaagacctgg acctcctaca ccagctgccg ctcacagcat cccttacaac    960
agctgcagag agaaagaacc tagctacccc atgcctgtgc aagagacaca ggccccagaa   1020
agccctggcg agaatagcga acaggctctg cagacactga gccccagagc cattcctaga   1080
aaccctgatg gcggccctct ggaaagctct agtgatctgg ccgctctgtc ccctctgaca   1140
agctctggac accaagagca ggataccgag ctgggcagca cacatacagc cggcgctaca   1200
agcagcctga caccttctag aggccccgtg tctcccagcg tgtcatttca gcctctggcc   1260
aggtctaccc ctagggcttc tagactgcct ggaccaacag gcagcgtggt gtctaccggc   1320
acaagcttca gctctagctc tcctggactg gctagtgccg gtgccgctga gggaaaacaa   1380
ggcgccgaat ctgatcaggc cgagcctatc atctgtagca gcggagcaga agcccctgcc   1440
aatagcctgc ctagcaaggt gccaaccaca ctgatgcccg tgaacacagt ggccctgaag   1500
gtgccagcta tcctgcctc cgtgtccacc gtgccttcta agctgccaac cagctctaag   1560
ccacctggcg ccgtgccatc taacgccctg acaaatcctg ctccaagcaa gctgcccatc   1620
aactccacaa gagccggcat ggtgccctct aaggtgccca catctatggt gctgaccaag   1680
gtgtccgcca gcaccgtgcc aacagatggc agctccagaa cgaggaaaac ccctgccgct   1740
cctactcctg ctggcgctac aggcggatct tctgcttggc tggatagcag cagcgagaac   1800
agaggcctgg gcagcgagct ttctaaacct ggcgtgctgg cttcccaggt ggacagccca   1860
ttttccggct gctttgagga cctggctatc agcgcctcta caagcctcgg catgggacct   1920
tgtcacggcc ccgaggaaaa cgagtacaag agcgagggca ccttcggcat ccacgtggcc   1980
gagaatccta gcatccaact gctggaaggc aaccccggac tccagctga tccagatggc   2040 ggaccaagac ctcaggccga cagaaagttc aagagcgcg aggtgccctg ccacagacct   2100
tctccaggtg ctctgtggct gcaggttgca gtgacaggcg tcctggtggt tacactgctc   2160
gtggtcctgt atagacggcg gctgcac                                        2187
```

<210> SEQ ID NO 6
<211> LENGTH: 729
<212> TYPE: PRT
<213> ORGANISM: Artificial sequence
<220> FEATURE:
<223> OTHER INFORMATION: Fusion of LMP1 from Epstein Barr virus and ISP1
      from Homo sapiens

<400> SEQUENCE: 6

Met Asp Leu Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
            20                  25                  30

Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
    50                  55                  60

-continued

```
Ile Ile Leu Ile Ile Phe Ile Phe Arg Arg Asp Leu Leu Cys Pro Leu
 65                  70                  75                  80

Gly Ala Leu Cys Leu Leu Leu Met Ile Thr Leu Leu Leu Ile Ala
             85                  90                  95

Leu Trp Asn Leu His Gly Gln Ala Leu Tyr Leu Gly Ile Val Leu Phe
                100                 105                 110

Ile Phe Gly Cys Leu Leu Val Leu Gly Leu Trp Ile Tyr Leu Leu Glu
            115                 120                 125

Ile Leu Trp Arg Leu Gly Ala Thr Ile Trp Gln Leu Leu Ala Phe Phe
130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Pro Phe
            180                 185                 190

Ala Glu Asp Lys Thr Tyr Lys Tyr Ile Cys Arg Asn Phe Ser Asn Phe
        195                 200                 205

Cys Asn Val Asp Val Val Glu Ile Leu Pro Tyr Leu Pro Cys Leu Thr
210                 215                 220

Ala Arg Asp Gln Asp Arg Leu Arg Ala Thr Cys Thr Leu Ser Gly Asn
225                 230                 235                 240

Arg Asp Thr Leu Trp His Leu Phe Asn Thr Leu Gln Arg Arg Pro Gly
                245                 250                 255

Trp Val Glu Tyr Phe Ile Ala Ala Leu Arg Gly Cys Glu Leu Val Asp
            260                 265                 270

Leu Ala Asp Glu Val Ala Ser Val Tyr Gln Ser Tyr Gln Pro Arg Thr
        275                 280                 285

Ser Asp Arg Pro Pro Asp Pro Leu Glu Pro Pro Ser Leu Pro Ala Glu
    290                 295                 300

Arg Pro Gly Pro Pro Thr Pro Ala Ala Ala His Ser Ile Pro Tyr Asn
305                 310                 315                 320

Ser Cys Arg Glu Lys Glu Pro Ser Tyr Pro Met Pro Val Gln Glu Thr
                325                 330                 335

Gln Ala Pro Glu Ser Pro Gly Glu Asn Ser Glu Gln Ala Leu Gln Thr
            340                 345                 350

Leu Ser Pro Arg Ala Ile Pro Arg Asn Pro Asp Gly Gly Pro Leu Glu
        355                 360                 365

Ser Ser Ser Asp Leu Ala Ala Leu Ser Pro Leu Thr Ser Ser Gly His
    370                 375                 380

Gln Glu Gln Asp Thr Glu Leu Gly Ser Thr His Thr Ala Gly Ala Thr
385                 390                 395                 400

Ser Ser Leu Thr Pro Ser Arg Gly Pro Val Ser Pro Ser Val Ser Phe
                405                 410                 415

Gln Pro Leu Ala Arg Ser Thr Pro Arg Ala Ser Arg Leu Pro Gly Pro
            420                 425                 430

Thr Gly Ser Val Val Ser Thr Gly Thr Ser Phe Ser Ser Ser Ser Pro
        435                 440                 445

Gly Leu Ala Ser Ala Gly Ala Ala Glu Gly Lys Gln Gly Ala Glu Ser
    450                 455                 460

Asp Gln Ala Glu Pro Ile Ile Cys Ser Ser Gly Ala Glu Ala Pro Ala
465                 470                 475                 480
```

```
Asn Ser Leu Pro Ser Lys Val Pro Thr Thr Leu Met Pro Val Asn Thr
                485                 490                 495

Val Ala Leu Lys Val Pro Ala Asn Pro Ala Ser Val Ser Thr Val Pro
            500                 505                 510

Ser Lys Leu Pro Thr Ser Ser Lys Pro Pro Gly Ala Val Pro Ser Asn
        515                 520                 525

Ala Leu Thr Asn Pro Ala Pro Ser Lys Leu Pro Ile Asn Ser Thr Arg
    530                 535                 540

Ala Gly Met Val Pro Ser Lys Val Pro Thr Ser Met Val Leu Thr Lys
545                 550                 555                 560

Val Ser Ala Ser Thr Val Pro Thr Asp Gly Ser Ser Arg Asn Glu Glu
                565                 570                 575

Thr Pro Ala Ala Pro Thr Pro Ala Gly Ala Thr Gly Gly Ser Ser Ala
            580                 585                 590

Trp Leu Asp Ser Ser Ser Glu Asn Arg Gly Leu Gly Ser Glu Leu Ser
        595                 600                 605

Lys Pro Gly Val Leu Ala Ser Gln Val Asp Ser Pro Phe Ser Gly Cys
    610                 615                 620

Phe Glu Asp Leu Ala Ile Ser Ala Ser Thr Ser Leu Gly Met Gly Pro
625                 630                 635                 640

Cys His Gly Pro Glu Glu Asn Glu Tyr Lys Ser Glu Gly Thr Phe Gly
                645                 650                 655

Ile His Val Ala Glu Asn Pro Ser Ile Gln Leu Leu Glu Gly Asn Pro
            660                 665                 670

Gly Pro Pro Ala Asp Pro Asp Gly Gly Pro Arg Pro Gln Ala Asp Arg
        675                 680                 685

Lys Phe Gln Glu Arg Glu Val Pro Cys His Arg Pro Ser Pro Gly Ala
    690                 695                 700

Leu Trp Leu Gln Val Ala Val Thr Gly Val Leu Val Val Thr Leu Leu
705                 710                 715                 720

Val Val Leu Tyr Arg Arg Arg Leu His
                725
```

<210> SEQ ID NO 7
<211> LENGTH: 2106
<212> TYPE: DNA
<213> ORGANISM: Artificial sequence
<220> FEATURE:
<223> OTHER INFORMATION: Fusion of LMP1 from Epstein Barr virus and IPS1
      from Homo sapiens

<400> SEQUENCE: 7

```
atggatctgg atctcgaaag aggacctcct ggacctagac ggcctcctag aggaccacct      60
ctgagcagct ctattggact ggccctgctg ctgcttctgc tggctctgct gttctggctg     120
tacatcatca tgagcaactg daccggcgga gcactgctgg tgctgtatgc ctttgctctg     180
atgctggtca tcatcatcct gatcatcttc atcttccggc gggacctgct gtgtcctctg     240
ggagcacttt gtctgttgct gctgatgatc accctcctgc tgatcgccct gtggaacctg     300
catggacagg ccctgtatct gggcatcgtg ctgttcatct tcggctgcct gctggttctc     360
ggcctgtgga tctacctgct ggaaatcctt ggagactgg cgccaccat ctggcagctg     420 ctggcctttt tcctggcctt ctttctggat atcatcctcc tcatcattgc cctgtacctg     480
cagcagaact ggtggaccct gctggtggat ctgcttggc tgctgctctt tctggccatc     540
ctgatttgga tgtactacca cggccagcgg cctttcgccg aggacaagac ctacaagtac     600
```

-continued

```
atctgccgga acttcagcaa cttctgcaac gtggacgtgg tggaaattct gccctacctg      660
ccttgcctga ccgccagaga tcaggacaga ctgagagcca catgtaccct gagcggcaac      720
agagacacac tgtggcacct gttcaacacc ctgcagagaa ggcctggctg ggtcgagtac      780
tttatcgccg ctctgagagg ctgcgagctg gtcgatctgg ctgatgaagt ggccagcgtg      840
taccagagct accagcctag aaccagcgac cggcctcctg atcctctcga acctccatct      900
ctgcccgccg aaagacctgg acctcctaca ccagctgccg ctcacagcat cccttacaac      960
agctgcagag agaaagaacc tagctacccc atgcctgtgc aagagacaca ggccccagaa     1020
agccctggcg agaatagcga acaggctctg cagacactga gccccagagc cattcctaga     1080
aaccctgatg gcggccctct ggaaagctct agtgatctgg ccgctctgtc ccctctgaca     1140
agctctggac accaagagca ggataccgag ctgggcagca cacatacagc cggcgctaca     1200
agcagcctga caccttctag aggccccgtg tctcccagcg tgtcatttca gcctctggcc     1260
aggtctaccc ctagggcttc tagactgcct ggaccaacag gcagcgtggt gtctaccggc     1320
acaagcttca gctctagctc tcctggactg gctagtgccg gtgccgctga gggaaaacaa     1380
ggcgccgaat ctgatcaggc cgagcctatc atctgtagca gcggagcaga agcccctgcc     1440
aatagcctgc ctagcaaggt gccaaccaca ctgatgcccg tgaacacagt ggccctgaag     1500
gtgccagcta atcctgcctc cgtgtccacc gtgccttcta agctgccaac cagctctaag     1560
ccacctggcg ccgtgccatc taacgccctg acaaatcctg ctccaagcaa gctgcccatc     1620
aactccacaa gagccggcat ggtgccctct aaggtgccca catctatggt gctgaccaag     1680
gtgtccgcca gcaccgtgcc aacagatggc agctccagaa cgaggaaaac ccctgccgct     1740
cctactcctg ctggcgctac aggcggatct tctgcttggc tggatagcag cagcgagaac     1800
agaggcctgg gcagcgagct ttctaaacct ggcgtgctgg cttcccaggt ggacagccca     1860
ttttccggct gctttgagga cctggctatc agcgcctcta caagcctcgg catgggacct     1920
tgtcacggcc ccgaggaaaa cgagtacaag agcgagggca ccttcggcat ccacgtggcc     1980
gagaatccta gcatccaact gctggaaggc aaccccggac ctccagctga tccagatggc     2040
ggaccaagac tcaggccga cagaaagttc aagagcgcg aggtgccctg ccacagacct     2100
tctcca                                                                2106
```

<210> SEQ ID NO 8
<211> LENGTH: 702
<212> TYPE: PRT
<213> ORGANISM: Artificial sequence
<220> FEATURE:
<223> OTHER INFORMATION: Fusion of LMP1 from Epstein Barr virus and IPS1
      from Homo sapiens

<400> SEQUENCE: 8

```
Met Asp Leu Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
                20                  25                  30

Leu Leu Ala Leu Leu Phe Trp Leu Tyr Ile Ile Met Ser Asn Trp Thr
            35                  40                  45

Gly Gly Ala Leu Leu Val Leu Tyr Ala Phe Ala Leu Met Leu Val Ile
        50                  55                  60

Ile Ile Leu Ile Ile Phe Ile Phe Arg Arg Asp Leu Leu Cys Pro Leu
65                  70                  75                  80
```

-continued

Gly Ala Leu Cys Leu Leu Leu Met Ile Thr Leu Leu Ile Ala
                85              90              95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
            115                 120                 125

Ile Leu Trp Arg Leu Gly Ala Thr Ile Trp Gln Leu Leu Ala Phe Phe
130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Pro Phe
            180                 185                 190

Ala Glu Asp Lys Thr Tyr Lys Tyr Ile Cys Arg Asn Phe Ser Asn Phe
            195                 200                 205

Cys Asn Val Asp Val Val Glu Ile Leu Pro Tyr Leu Pro Cys Leu Thr
    210                 215                 220

Ala Arg Asp Gln Asp Arg Leu Arg Ala Thr Cys Thr Leu Ser Gly Asn
225                 230                 235                 240

Arg Asp Thr Leu Trp His Leu Phe Asn Thr Leu Gln Arg Arg Pro Gly
                245                 250                 255

Trp Val Glu Tyr Phe Ile Ala Ala Leu Arg Gly Cys Glu Leu Val Asp
            260                 265                 270

Leu Ala Asp Glu Val Ala Ser Val Tyr Gln Ser Tyr Gln Pro Arg Thr
            275                 280                 285

Ser Asp Arg Pro Pro Asp Pro Leu Glu Pro Pro Ser Leu Pro Ala Glu
            290                 295                 300

Arg Pro Gly Pro Pro Thr Pro Ala Ala Ala His Ser Ile Pro Tyr Asn
305                 310                 315                 320

Ser Cys Arg Glu Lys Glu Pro Ser Tyr Pro Met Pro Val Gln Glu Thr
                325                 330                 335

Gln Ala Pro Glu Ser Pro Gly Glu Asn Ser Glu Gln Ala Leu Gln Thr
            340                 345                 350

Leu Ser Pro Arg Ala Ile Pro Arg Asn Pro Asp Gly Gly Pro Leu Glu
            355                 360                 365

Ser Ser Ser Asp Leu Ala Ala Leu Ser Pro Leu Thr Ser Ser Gly His
370                 375                 380

Gln Glu Gln Asp Thr Glu Leu Gly Ser Thr His Thr Ala Gly Ala Thr
385                 390                 395                 400

Ser Ser Leu Thr Pro Ser Arg Gly Pro Val Ser Pro Ser Val Ser Phe
                405                 410                 415

Gln Pro Leu Ala Arg Ser Thr Pro Arg Ala Ser Arg Leu Pro Gly Pro
            420                 425                 430

Thr Gly Ser Val Val Ser Thr Gly Thr Ser Phe Ser Ser Ser Ser Pro
            435                 440                 445

Gly Leu Ala Ser Ala Gly Ala Ala Glu Gly Lys Gln Gly Ala Glu Ser
            450                 455                 460

Asp Gln Ala Glu Pro Ile Ile Cys Ser Ser Gly Ala Glu Ala Pro Ala
465                 470                 475                 480

Asn Ser Leu Pro Ser Lys Val Pro Thr Thr Leu Met Pro Val Asn Thr
                485                 490                 495

-continued

```
Val Ala Leu Lys Val Pro Ala Asn Pro Ala Ser Val Ser Thr Val Pro
            500                 505                 510

Ser Lys Leu Pro Thr Ser Ser Lys Pro Pro Gly Ala Val Pro Ser Asn
        515                 520                 525

Ala Leu Thr Asn Pro Ala Pro Ser Lys Leu Pro Ile Asn Ser Thr Arg
    530                 535                 540

Ala Gly Met Val Pro Ser Lys Val Pro Thr Ser Met Val Leu Thr Lys
545                 550                 555                 560

Val Ser Ala Ser Thr Val Pro Thr Asp Gly Ser Ser Arg Asn Glu Glu
                565                 570                 575

Thr Pro Ala Ala Pro Thr Pro Ala Gly Ala Thr Gly Gly Ser Ser Ala
            580                 585                 590

Trp Leu Asp Ser Ser Ser Glu Asn Arg Gly Leu Gly Ser Glu Leu Ser
        595                 600                 605

Lys Pro Gly Val Leu Ala Ser Gln Val Asp Ser Pro Phe Ser Gly Cys
    610                 615                 620

Phe Glu Asp Leu Ala Ile Ser Ala Ser Thr Ser Leu Gly Met Gly Pro
625                 630                 635                 640

Cys His Gly Pro Glu Glu Asn Glu Tyr Lys Ser Glu Gly Thr Phe Gly
                645                 650                 655

Ile His Val Ala Glu Asn Pro Ser Ile Gln Leu Leu Glu Gly Asn Pro
            660                 665                 670

Gly Pro Pro Ala Asp Pro Asp Gly Gly Pro Arg Pro Gln Ala Asp Arg
        675                 680                 685

Lys Phe Gln Glu Arg Glu Val Pro Cys His Arg Pro Ser Pro
    690                 695                 700
```

<210> SEQ ID NO 9
<211> LENGTH: 1953
<212> TYPE: DNA
<213> ORGANISM: Artificial sequence
<220> FEATURE:
<223> OTHER INFORMATION: Fusion of LMP1 of Epstein Barr virus and IPS1
      from Homo sapiens

<400> SEQUENCE: 9

```
atggatctgg atctcgaaag aggacctcct ggacctagac ggcctcctag aggaccacct      60
ctgagcagct ctattggact ggccctgctg ctgcttctgc tggctctgct gttctggctg     120
tacatcatca tgagcaactg daccggcgga gcactgctgg tgctgtatgc ctttgctctg     180
atgctggtca tcatcatcct gatcatcttc atcttccggc gggacctgct gtgtcctctg     240
ggagcacttt gtctgttgct gctgatgatc accctcctgc tgatcgccct gtggaacctg     300
catggacagg ccctgtatct gggcatcgtg ctgttcatct tcggctgcct gctggttctc     360
ggcctgtgga tctacctgct ggaaatcctt tggagactgg cgccaccat ctggcagctg      420 ctggcctttt cctggccttt ctttctggat atcatcctcc tcatcattgc cctgtacctg     480
cagcagaact ggtggaccct gctggtggat ctgctttggc tgctgctctt ctgccatc      540 ctgatttgga tgtactacca cggccagcgg cctttcgccg aggacaagac ctacaagtac    600
atctgccgga acttcagcaa cttctgcaac gtgacgtgg tggaaattct gcccctacctg    660 ccttgcctga ccgccagaga tcaggacaga ctgagagcca catgtaccct gagcggcaac     720
agagacacac tgtggcacct gttcaacacc ctgcagagaa ggcctggctg gtcgagtac     780 tttatcgccg ctctgagagg ctgcgagctg gtcgatctgg ctgatgaagt ggccagcgtg    840
taccagagct accagcctag aaccagcgac cggggcgaga tagcgaaca ggctctgcag    900
```

```
acactgagcc ccagagccat tcctagaaac cctgatggcg gccctctgga aagctctagt    960
gatctggccg ctctgtcccc tctgacaagc tctggacacc aagagcagga taccgagctg   1020
ggcagcacac atacagccgg cgctacaagc agcctgacac cttctagagg ccccgtgtct   1080
cccagcgtgt catttcagcc tctggccagg tctacccta gggcttctag actgcctgga    1140
ccaacaggca gcgtggtgtc taccggcaca agcttcagct ctagctctcc tggactggct   1200
agtgccggtg ccgctgaggg aaaacaaggc gccgaatctg atcaggccga gcctatcatc   1260
tgtagcagcg agcagaagc ccctgccaat agcctgccta gcaaggtgcc aaccacactg    1320
atgcccgtga acacagtggc cctgaaggtg ccagctaatc ctgcctccgt gtccaccgtg   1380
ccttctaagc tgccaaccag ctctaagcca cctggcgccg tgccatctaa cgccctgaca   1440
aatcctgctc caagcaagct gcccatcaac tccacaagag ccggcatggt gccctctaag   1500
gtgcccacat ctatggtgct gaccaaggtg tccgccagca ccgtgccaac agatggcagc   1560
tccagaaacg aggaaacccc tgccgctcct actcctgctg cgctacagg cggatcttct    1620
gcttggctgg atagcagcag cgagaacaga ggcctgggca gcgagctttc taaacctggc   1680
gtgctggctt cccaggtgga cagcccattt tccggctgct ttgaggacct ggctatcagc   1740
gcctctacaa gcctcggcat gggaccttgt cacggccccg aggaaaacga gtacaagagc   1800
gagggcacct tcggcatcca cgtggccgag aatcctagca tccaactgct ggaaggcaac   1860
cccggacctc cagctgatcc agatggcgga ccaagacctc aggccgacag aaagttccaa   1920
gagcgcgagg tgccctgcca cagaccttct cca                                1953
```

<210> SEQ ID NO 10
<211> LENGTH: 651
<212> TYPE: PRT
<213> ORGANISM: Artificial Sequence
<220> FEATURE:
<223> OTHER INFORMATION: Fustion of LMP1 of Epstein Barr virus and IPS1
      of Homo sapiens

<400> SEQUENCE: 10

```
Met Asp Leu Asp Leu Glu Arg Gly Pro Pro Gly Pro Arg Arg Pro Pro
1               5                   10                  15

Arg Gly Pro Pro Leu Ser Ser Ile Gly Leu Ala Leu Leu Leu Leu
            20                  25                  30

Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
    50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
    130                 135                 140

Leu Ala Phe Phe Leu Asp Ile Ile Leu Leu Ile Ile Ala Leu Tyr Leu
145                 150                 155                 160
```

```
Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Pro Phe
            180                 185                 190

Ala Glu Asp Lys Thr Tyr Lys Tyr Ile Cys Arg Asn Phe Ser Asn Phe
        195                 200                 205

Cys Asn Val Asp Val Val Glu Ile Leu Pro Tyr Leu Pro Cys Leu Thr
    210                 215                 220

Ala Arg Asp Gln Asp Arg Leu Arg Ala Thr Cys Thr Leu Ser Gly Asn
225                 230                 235                 240

Arg Asp Thr Leu Trp His Leu Phe Asn Thr Leu Gln Arg Arg Pro Gly
                245                 250                 255

Trp Val Glu Tyr Phe Ile Ala Ala Leu Arg Gly Cys Glu Leu Val Asp
            260                 265                 270

Leu Ala Asp Glu Val Ala Ser Val Tyr Gln Ser Tyr Gln Pro Arg Thr
        275                 280                 285

Ser Asp Arg Gly Glu Asn Ser Glu Gln Ala Leu Gln Thr Leu Ser Pro
    290                 295                 300

Arg Ala Ile Pro Arg Asn Pro Asp Gly Gly Pro Leu Glu Ser Ser Ser
305                 310                 315                 320

Asp Leu Ala Ala Leu Ser Pro Leu Thr Ser Ser Gly His Gln Glu Gln
                325                 330                 335

Asp Thr Glu Leu Gly Ser Thr His Thr Ala Gly Ala Thr Ser Ser Leu
            340                 345                 350

Thr Pro Ser Arg Gly Pro Val Ser Pro Ser Val Ser Phe Gln Pro Leu
        355                 360                 365

Ala Arg Ser Thr Pro Arg Ala Ser Arg Leu Pro Gly Pro Thr Gly Ser
    370                 375                 380

Val Val Ser Thr Gly Thr Ser Phe Ser Ser Ser Pro Gly Leu Ala
385                 390                 395                 400

Ser Ala Gly Ala Ala Glu Gly Lys Gln Gly Ala Glu Ser Asp Gln Ala
                405                 410                 415

Glu Pro Ile Ile Cys Ser Ser Gly Ala Glu Ala Pro Ala Asn Ser Leu
            420                 425                 430

Pro Ser Lys Val Pro Thr Thr Leu Met Pro Val Asn Thr Val Ala Leu
        435                 440                 445

Lys Val Pro Ala Asn Pro Ala Ser Val Ser Thr Val Pro Ser Lys Leu
    450                 455                 460

Pro Thr Ser Ser Lys Pro Pro Gly Ala Val Pro Ser Asn Ala Leu Thr
465                 470                 475                 480

Asn Pro Ala Pro Ser Lys Leu Pro Ile Asn Ser Thr Arg Ala Gly Met
                485                 490                 495

Val Pro Ser Lys Val Pro Thr Ser Met Val Leu Thr Lys Val Ser Ala
            500                 505                 510

Ser Thr Val Pro Thr Asp Gly Ser Ser Arg Asn Glu Thr Pro Ala
        515                 520                 525

Ala Pro Thr Pro Ala Gly Ala Thr Gly Gly Ser Ala Trp Leu Asp
    530                 535                 540

Ser Ser Ser Glu Asn Arg Gly Leu Gly Ser Glu Leu Ser Lys Pro Gly
545                 550                 555                 560

Val Leu Ala Ser Gln Val Asp Ser Pro Phe Ser Gly Cys Phe Glu Asp
                565                 570                 575
```

```
Leu Ala Ile Ser Ala Ser Thr Ser Leu Gly Met Gly Pro Cys His Gly
            580                 585                 590

Pro Glu Glu Asn Glu Tyr Lys Ser Glu Gly Thr Phe Gly Ile His Val
    595                 600                 605

Ala Glu Asn Pro Ser Ile Gln Leu Leu Glu Gly Asn Pro Gly Pro Pro
610                 615                 620

Ala Asp Pro Asp Gly Gly Pro Arg Pro Gln Ala Asp Arg Lys Phe Gln
625                 630                 635                 640

Glu Arg Glu Val Pro Cys His Arg Pro Ser Pro
                645                 650

<210> SEQ ID NO 11
<211> LENGTH: 2109
<212> TYPE: DNA
<213> ORGANISM: Artificial sequence
<220> FEATURE:
<223> OTHER INFORMATION: Fustion of LMP1 of Epstein Barr virus and IPS1
      of Homo sapiens

<400> SEQUENCE: 11
atggatctgg atctcgaaag aggacctcct ggacctagac ggcctcctag aggaccacct      60
ctgagcagct ctattggact ggccctgctg ctgcttctgc tggctctgct gttctggctg     120
tacatcatca tgagcaactg gaccggcgga gcactgctgg tgctgtatgc ctttgctctg     180
atgctggtca tcatcatcct gatcatcttc atcttccggc gggacctgct gtgtcctctg     240
ggagcacttt gtctgttgct gctgatgatc accctcctgc tgatcgccct gtggaacctg     300
catgacaggc cctgtatctg ggcatcgtg ctgttcatct tcggctgcct gctggttctc     360
ggcctgtgga tctacctgct ggaaatcctt tggagactgg cgccaccat ctggcagctg     420 ctggcctttt tcctggcctt ctttctggat atcatcctcc tcatcattgc cctgtacctg     480
cagcagaact ggtggaccct gctggtggat ctgctttggc tgctgctctt tctggccatc     540
ctgatttgga tgtactacca cggcagcgg cccagcccca gacactgccc cgtggagaga     600
gagcagttca gagagacgc ccagcccaga cccggcggcg accccgacgc cccccccggc     660
cccaacggcg agctgctgca gatcagcccc aacgaggccg tgcacatcgg cttcaccggc     720
gagagcaagt acgagaacga ggagcccggc cactgccccg catgggcct gagcaccagc     780 gccagcatcg ccctggacga gttctgcggc agcttcccca gcgacgtgca gagcgccctg     840
gtgggcccca gagcctgga gagcggcctg ggcagaaacg agagcagcag cgacctgtgg     900
gccagcagcg gcggcaccgc cggcgccccc accccgccg cccccaccga ggagaacaga     960
agcagcggcg acaccccgt gaccagcgcc agcgtgaaga ccctggtgat gagcacccc    1020 gtgaagagcc ccgtgatggg cgccagaacc agcaacatcc ccctgaagag ccccgccccc    1080
aacaccctgg ccaacagccc cgtggccggc ccccccaaga gcagcacccc cctgaagagc    1140
cccgtgacca gcgtgagcgc cccaacgccc cgtgaagc tggccgtgac caacgtgccc    1200
atgctgacca ccccgtgaa gagccccctg agcaacgccc cgccgaggc cggcagcagc    1260 tgcatcatcc ccgaggccca ggacagcgag gccggccaga agggcgaggc cgccggcgcc    1320
agcgccctgg gccccagcag cagcagcttc agcaccggca ccagcgtggt gagcggcacc    1380 cccggcccc tgagaagcgc cagacccacc agcagagccc tgccccagtt cagcgtgagc    1440
cccagcgtgc ccggcagaag ccccacccct agcagcaccg ccggcgccac ccacaccagc    1500
ggcctggaga ccgaccagga gcagcacggc agcagcaccc tgccccagcct ggccgccctg    1560 gacagcagca gcgagctgcc cggcggcgac cccaacagac ccatcgccag acccagcctg    1620
```

-continued

```
acccagctgg cccaggagag caacgagggc cccagcgagc ccgcccagac cgagcaggtg    1680
cccatgccct acagccccga gaaggagaga tgcagcaact accccatcag ccacgccgcc    1740
gcccccaccc ccccggcccc cagagaggcc ccctgagcc ccccgagct gcccgacccc     1800 cccagagaca gcaccagacc ccagtacagc cagtacgtga gcgccgtgga ggacgccctg    1860
gacgtgctgg agtgcggcag actggccgcc atcttctacg aggtgtgggg ccccagaaga    1920
cagctgacca acttcctgca ctggctgacc gacagaaacg gcagcctgac ctgcaccgcc    1980
agactgagag accaggacag agccaccctg tgccccctgt accccctgat cgaggtggtg    2040
gacgtgaact gcttcaacag cttcaacaga tgcatctaca agtacaccaa ggacgaggcc    2100
ttccccatg                                                            2109
```

<210> SEQ ID NO 12
<211> LENGTH: 703
<212> TYPE: PRT
<213> ORGANISM: Artificial sequence
<220> FEATURE:
<223> OTHER INFORMATION: Fusion of LMP1 of Epstein Barr Virus and IPS1
      of Homo sapiens

<400> SEQUENCE: 12

```
Met Asp Leu Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
                20                  25                  30

Leu Leu Ala Leu Leu Phe Trp Leu Tyr Ile Ile Met Ser Asn Trp Thr
            35                  40                  45

Gly Gly Ala Leu Leu Val Leu Tyr Ala Phe Ala Leu Met Leu Val Ile
        50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
    130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Pro Ser
            180                 185                 190

Pro Arg His Cys Pro Val Glu Arg Glu Gln Phe Lys Arg Asp Ala Gln
        195                 200                 205

Pro Arg Pro Gly Gly Asp Pro Asp Ala Pro Pro Gly Pro Asn Gly Glu
    210                 215                 220

Leu Leu Gln Ile Ser Pro Asn Glu Ala Val His Ile Gly Phe Thr Gly
225                 230                 235                 240

Glu Ser Lys Tyr Glu Asn Glu Glu Pro Gly His Cys Pro Gly Met Gly
                245                 250                 255
```

-continued

Leu Ser Thr Ser Ala Ser Ile Ala Leu Asp Glu Phe Cys Gly Ser Phe
            260                 265                 270

Pro Ser Asp Val Gln Ser Ala Leu Val Gly Pro Lys Ser Leu Glu Ser
            275                 280                 285

Gly Leu Gly Arg Asn Glu Ser Ser Ser Asp Leu Trp Ala Ser Ser Gly
        290                 295                 300

Gly Thr Ala Gly Ala Pro Thr Pro Ala Pro Thr Glu Glu Asn Arg
305                 310                 315                 320

Ser Ser Gly Asp Thr Pro Val Thr Ser Ala Ser Val Lys Thr Leu Val
            325                 330                 335

Met Ser Thr Pro Val Lys Ser Pro Val Met Gly Ala Arg Thr Ser Asn
            340                 345                 350

Ile Pro Leu Lys Ser Pro Ala Pro Asn Thr Leu Ala Asn Ser Pro Val
        355                 360                 365

Ala Gly Pro Pro Lys Ser Ser Thr Pro Leu Lys Ser Pro Val Thr Ser
        370                 375                 380

Val Ser Ala Pro Asn Ala Pro Val Lys Leu Ala Val Thr Asn Val Pro
385                 390                 395                 400

Met Leu Thr Thr Pro Val Lys Ser Pro Leu Ser Asn Ala Pro Ala Glu
            405                 410                 415

Ala Gly Ser Ser Cys Ile Ile Pro Glu Ala Gln Asp Ser Glu Ala Gly
            420                 425                 430

Gln Lys Gly Glu Ala Ala Gly Ala Ser Ala Leu Gly Pro Ser Ser Ser
        435                 440                 445

Ser Phe Ser Thr Gly Thr Ser Val Val Ser Gly Thr Pro Gly Pro Leu
        450                 455                 460

Arg Ser Ala Arg Pro Thr Ser Arg Ala Leu Pro Gln Phe Ser Val Ser
465                 470                 475                 480

Pro Ser Val Pro Gly Arg Ser Pro Thr Leu Ser Ser Thr Ala Gly Ala
            485                 490                 495

Thr His Thr Ser Gly Leu Glu Thr Asp Gln Glu Gln His Gly Ser Ser
            500                 505                 510

Thr Leu Pro Ser Leu Ala Ala Leu Asp Ser Ser Glu Leu Pro Gly
        515                 520                 525

Gly Asp Pro Asn Arg Pro Ile Ala Arg Pro Ser Leu Thr Gln Leu Ala
        530                 535                 540

Gln Glu Ser Asn Glu Gly Pro Ser Glu Pro Ala Gln Thr Glu Gln Val
545                 550                 555                 560

Pro Met Pro Tyr Ser Pro Glu Lys Glu Arg Cys Ser Asn Tyr Pro Ile
            565                 570                 575

Ser His Ala Ala Ala Pro Thr Pro Pro Gly Pro Arg Glu Ala Pro Leu
        580                 585                 590

Ser Pro Pro Glu Leu Pro Asp Pro Arg Asp Ser Thr Arg Pro Gln
        595                 600                 605

Tyr Ser Gln Tyr Val Ser Ala Val Glu Asp Ala Leu Asp Val Leu Glu
        610                 615                 620

Cys Gly Arg Leu Ala Ala Ile Phe Tyr Glu Val Trp Gly Pro Arg Arg
625                 630                 635                 640

Gln Leu Thr Asn Phe Leu His Trp Leu Thr Asp Arg Asn Gly Ser Leu
            645                 650                 655

Thr Cys Thr Ala Arg Leu Arg Asp Gln Asp Arg Ala Thr Leu Cys Pro
            660                 665                 670

```
Leu Tyr Pro Leu Ile Glu Val Val Asp Val Asn Cys Phe Asn Ser Phe
            675                 680                 685

Asn Arg Cys Ile Tyr Lys Tyr Thr Lys Asp Glu Ala Phe Pro Met
    690                 695                 700

<210> SEQ ID NO 13
<211> LENGTH: 2694
<212> TYPE: DNA
<213> ORGANISM: Artificial sequence
<220> FEATURE:
<223> OTHER INFORMATION: Fusion of LMP1 of Epstein Barr virus and IPS1
      of Homo sapiens

<400> SEQUENCE: 13
atggatctgg acctggaaag aggacctcct ggacctagac ggcctcctag aggaccacct       60
ctgagcagct ctattggact ggccctgctg ctgcttctgc tggctctgct gttctggctg      120
tacatcatca tgagcaactg gaccggcgga gcactgctgg tgctgtatgc ctttgctctg      180
atgctggtca tcatcatcct gatcatcttc atcttccggc gggacctgct gtgtcctctg      240
ggagcacttt gtctgttgct gctgatgatc accctcctgc tgatcgccct gtggaacctg      300
catggacagg ccctgtatct gggaatcgtg ctgttcatct tcggctgcct gctggttctc      360
ggcctgtgga tctacctgct ggaaatcctt tggagactgg cgccaccat ctggcagctg       420 ctggcctttt tcctggcctt cttctctgat atcatcctcc tcatcattgc cctgtacctg      480
cagcagaact ggtggaccct gctggtggat ctgctttggc tgctgctctt tctggccatc      540
ctgatttgga tgtactacca cggccagcgg cacagcgacg aacaccacca tgatgacagc      600
ctgcctcatc ctcagcaggc caccgacgat agcagcaacc agagcgacag caacagcaac      660
gagggcagac atctgctgct ggtgtctggt gctggcgacg acctcctct gtgttctcaa       720 aatcttggcg cccctggcgg cggaccaaac aatggacctc aggaccccga aacaccgac       780 gacaatggcc ctcaagatcc tgataatacc gatgacaacg cccacacga ccctctgcct       840 caagacccag ataacacaga cgataacggt ccacaagatc cggacaatac tgacgataat      900
ggaccccacg atccactgcc tcacaaccct agcgatagcg ccggaaatga tgcggaccct      960
ccacagctga ccgaggaagt ggaaaacaaa ggcgagatca gggccctcc tctgatgacc      1020 gatggcggag tggacactc tcacgattct ggccacgacg gcatcgaccc tcatctgcct      1080
acactgctgc tcggcacatc tggctctggc ggcgacgatg atgatcctca tggacctgtg      1140
cagctgagct actacgaccc tttcgccgag gacaagacct acaagtacat ctgccggaac      1200
ttcagcaact tctgcaacgt ggacgtggtg gaaattctgc cctacctgcc ttgcctgacc      1260
gccagagatc aggacagact gagagccaca tgtaccctga cggcaacag agacacactg      1320 tggcacctgt caacaccct gcagagaagg cctggctggg tcgagtactt tatcgccgct      1380
ctgagaggct gcgagctggt cgatctggct gatgaagtgg ccagcgtgta ccagagctac      1440
cagcctagaa ccagcgaccg gcctcctgat cctctcgaac tccatctct gcccgccgaa      1500 agacctggac tcctacacc agctgccgct cacagcatcc cttacaacag ctgcagagag      1560
aaagaaccta gctaccccat gcctgtgcaa gagacacagg cccagaaag ccctggcgag      1620 aatagcgaac aggctctgca gacactgagc cccagagcca ttcctagaaa ccctgatggc      1680
ggccctctgg aaagctctag tgatctggcc gctctgtccc ctgacaagt ctctggacac      1740 caagagcagg ataccgagct gggcagcaca catacagccg cgctacaag cagcctgaca      1800 ccttctagag gccccgtgtc tcccagcgtg tcatttcagc ctctggccag gtctacccct      1860
```

```
agggcttcta gactgcctgg accaacaggc agcgtggtgt ctaccggcac aagcttcagc    1920
tctagctctc ctggactggc tagtgccggt gccgctgagg gaaaacaagg cgccgaatct    1980
gatcaggccg agcctatcat ctgtagcagc ggagcagaag cccctgccaa tagcctgcct    2040
agcaaggtgc caaccacact gatgcccgtg aacacagtgg ccctgaaggt gccagctaat    2100
cctgcctccg tgtccaccgt gccttctaag ctgccaacca gctctaagcc acctggcgcc    2160
gtgccatcta acgccctgac aaatcctgct ccaagcaagc tgcccatcaa ctccacaaga    2220
gccggcatgg tgccctctaa ggtgcccaca tctatggtgc tgaccaaggt gtccgccagc    2280
accgtgccaa cagatggcag ctccagaaac gaggaaaccc ctgccgctcc tactcctgct    2340
ggcgctacag gcggatcttc tgcttggctg gatagcagca gcgagaacag aggcctgggc    2400
agcgagcttt ctaaacctgg cgtgctggct tcccaggtgg acagcccatt ttccggctgc    2460
tttgaggacc tggctatcag cgcctctaca agcctcggca tgggaccttg tcacggcccc    2520
gaggaaaacg agtacaagag cgagggcacc ttcggcatcc acgtggccga gaatcctagc    2580
atccaactgc tggaaggcaa ccccggacct ccagctgatc cagatggcgg accaagacct    2640
caggccgaca gaaagttcca agagcgcgag gtgccctgcc acagaccttc tcca          2694
```

<210> SEQ ID NO 14
<211> LENGTH: 898
<212> TYPE: PRT
<213> ORGANISM: Artificial sequence
<220> FEATURE:
<223> OTHER INFORMATION: Fusion of LMP1 of Epstein Barr virus and IPS1
      of Homo sapiens

<400> SEQUENCE: 14

```
Met Asp Leu Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
            20                  25                  30

Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
    50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
    130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg His Ser
            180                 185                 190

Asp Glu His His His Asp Asp Ser Leu Pro His Pro Gln Gln Ala Thr
        195                 200                 205
```

```
Asp Asp Ser Ser Asn Gln Ser Asp Ser Asn Ser Asn Glu Gly Arg His
    210                 215                 220

Leu Leu Leu Val Ser Gly Ala Gly Asp Gly Pro Pro Leu Cys Ser Gln
225                 230                 235                 240

Asn Leu Gly Ala Pro Gly Gly Pro Asn Asn Gly Pro Gln Asp Pro
                245                 250                 255

Asp Asn Thr Asp Asp Asn Gly Pro Gln Asp Pro Asp Asn Thr Asp Asp
            260                 265                 270

Asn Gly Pro His Asp Pro Leu Pro Gln Asp Pro Asp Asn Thr Asp Asp
        275                 280                 285

Asn Gly Pro Gln Asp Pro Asn Thr Asp Asp Asn Gly Pro His Asp
    290                 295                 300

Pro Leu Pro His Asn Pro Ser Asp Ser Ala Gly Asn Asp Gly Pro
305                 310                 315                 320

Pro Gln Leu Thr Glu Glu Val Glu Asn Lys Gly Gly Asp Gln Gly Pro
                325                 330                 335

Pro Leu Met Thr Asp Gly Gly Gly His Ser His Asp Ser Gly His
                340                 345                 350

Asp Gly Ile Asp Pro His Leu Pro Thr Leu Leu Leu Gly Thr Ser Gly
            355                 360                 365

Ser Gly Gly Asp Asp Asp Pro His Gly Pro Val Gln Leu Ser Tyr
370                 375                 380

Tyr Asp Pro Phe Ala Glu Asp Lys Thr Tyr Lys Tyr Ile Cys Arg Asn
385                 390                 395                 400

Phe Ser Asn Phe Cys Asn Val Asp Val Val Glu Ile Leu Pro Tyr Leu
                405                 410                 415

Pro Cys Leu Thr Ala Arg Asp Gln Asp Arg Leu Arg Ala Thr Cys Thr
            420                 425                 430

Leu Ser Gly Asn Arg Asp Thr Leu Trp His Leu Phe Asn Thr Leu Gln
        435                 440                 445

Arg Arg Pro Gly Trp Val Glu Tyr Phe Ile Ala Ala Leu Arg Gly Cys
    450                 455                 460

Glu Leu Val Asp Leu Ala Asp Glu Val Ala Ser Val Tyr Gln Ser Tyr
465                 470                 475                 480

Gln Pro Arg Thr Ser Asp Arg Pro Pro Asp Pro Leu Glu Pro Pro Ser
                485                 490                 495

Leu Pro Ala Glu Arg Pro Gly Pro Pro Thr Pro Ala Ala Ala His Ser
                500                 505                 510

Ile Pro Tyr Asn Ser Cys Arg Glu Lys Glu Pro Ser Tyr Pro Met Pro
            515                 520                 525

Val Gln Glu Thr Gln Ala Pro Glu Ser Pro Gly Glu Asn Ser Glu Gln
        530                 535                 540

Ala Leu Gln Thr Leu Ser Pro Arg Ala Ile Pro Arg Asn Pro Asp Gly
545                 550                 555                 560

Gly Pro Leu Glu Ser Ser Ser Asp Leu Ala Ala Leu Ser Pro Leu Thr
                565                 570                 575

Ser Ser Gly His Gln Glu Gln Asp Thr Glu Leu Gly Ser Thr His Thr
            580                 585                 590

Ala Gly Ala Thr Ser Ser Leu Thr Pro Ser Arg Gly Pro Val Ser Pro
        595                 600                 605

Ser Val Ser Phe Gln Pro Leu Ala Arg Ser Thr Pro Arg Ala Ser Arg
    610                 615                 620
```

```
Leu Pro Gly Pro Thr Gly Ser Val Val Ser Thr Gly Thr Ser Phe Ser
625                 630                 635                 640

Ser Ser Ser Pro Gly Leu Ala Ser Ala Gly Ala Ala Glu Gly Lys Gln
            645                 650                 655

Gly Ala Glu Ser Asp Gln Ala Glu Pro Ile Ile Cys Ser Ser Gly Ala
        660                 665                 670

Glu Ala Pro Ala Asn Ser Leu Pro Ser Lys Val Pro Thr Thr Leu Met
    675                 680                 685

Pro Val Asn Thr Val Ala Leu Lys Val Pro Ala Asn Pro Ala Ser Val
690                 695                 700

Ser Thr Val Pro Ser Lys Leu Pro Thr Ser Ser Lys Pro Pro Gly Ala
705                 710                 715                 720

Val Pro Ser Asn Ala Leu Thr Asn Pro Ala Pro Ser Lys Leu Pro Ile
                725                 730                 735

Asn Ser Thr Arg Ala Gly Met Val Pro Ser Lys Val Pro Thr Ser Met
            740                 745                 750

Val Leu Thr Lys Val Ser Ala Ser Thr Val Pro Thr Asp Gly Ser Ser
        755                 760                 765

Arg Asn Glu Glu Thr Pro Ala Ala Pro Thr Pro Ala Gly Ala Thr Gly
770                 775                 780

Gly Ser Ser Ala Trp Leu Asp Ser Ser Glu Asn Arg Gly Leu Gly
785                 790                 795                 800

Ser Glu Leu Ser Lys Pro Gly Val Leu Ala Ser Gln Val Asp Ser Pro
                805                 810                 815

Phe Ser Gly Cys Phe Glu Asp Leu Ala Ile Ser Ala Ser Thr Ser Leu
            820                 825                 830

Gly Met Gly Pro Cys His Gly Pro Glu Glu Asn Glu Tyr Lys Ser Glu
        835                 840                 845

Gly Thr Phe Gly Ile His Val Ala Glu Asn Pro Ser Ile Gln Leu Leu
    850                 855                 860

Glu Gly Asn Pro Gly Pro Pro Ala Asp Pro Asp Gly Gly Pro Arg Pro
865                 870                 875                 880

Gln Ala Asp Arg Lys Phe Gln Glu Arg Glu Val Pro Cys His Arg Pro
                885                 890                 895

Ser Pro

<210> SEQ ID NO 15
<211> LENGTH: 2541
<212> TYPE: DNA
<213> ORGANISM: Artificial sequence
<220> FEATURE:
<223> OTHER INFORMATION: LMP1 of Epstein Barr virus and IPS1 of Homo
      sapiens

<400> SEQUENCE: 15
atggatctgg acctggaaag aggacctcct ggacctagac ggcctcctag aggaccacct       60
ctgagcagct ctattggact ggccctgctg ctgcttctgc tggctctgct gttctggctg      120
tacatcatca tgagcaactg gaccggcgga gcactgctgg tgctgtatgc ctttgctctg      180
atgctggtca tcatcatcct gatcatcttc atcttccggc gggacctgct gtgtcctctg      240
ggagcacttt gtctgttgct gctgatgatc accctcctgc tgatcgccct gtggaacctg      300
catggacagg ccctgtatct gggaatcgtg ctgttcatct tcggctgcct gctggttctc      360
ggctgtggga tctaccctgc tggaaatcct tggagactgg cgccaccat ctggcagctg      420 ctggcctttt tcctggcctt ctttctggat atcatcctcc tcatcattgc cctgtacctg      480
```

```
cagcagaact ggtggaccct gctggtggat ctgctttggc tgctgctctt tctggccatc    540
ctgatttgga tgtactacca cggccagcgg cacagcgacg aacaccacca tgatgacagc    600
ctgcctcatc ctcagcaggc caccgacgat agcagcaacc agagcgacag caacagcaac    660
gagggcagac atctgctgct ggtgtctggt gctggcgacg gacctcctct gtgttctcaa    720
aatcttggcg ccctggcgg cggaccaaac aatggacctc aggaccccga caacaccgac    780
gacaatggcc tcaagatcc tgataatacc gatgacaacg ccccacacga ccctctgcct    840
caagacccag ataacacaga cgataacggt ccacaagatc cggacaatac tgacgataat    900
ggaccccacg atccactgcc tcacaaccct agcgatagcg ccggaaatga tggcggacct    960
ccacagctga ccgaggaagt ggaaaacaaa ggcggagatc agggccctcc tctgatgacc    1020
gatggcggag gtggacactc tcacgattct ggccacgacg gcatcgaccc tcatctgcct    1080
acactgctgc tcggcacatc tggctctggc ggcgacgatg atgatcctca tggacctgtg    1140
cagctgagct actacgaccc tttcgccgag gacaagacct acaagtacat ctgccggaac    1200
ttcagcaact tctgcaacgt ggacgtggtg gaaattctgc cctacctgcc ttgcctgacc    1260
gccagagatc aggacagact gagagccaca tgtaccctga gcggcaacag agacacactg    1320
tggcacctgt tcaacaccct gcagagaagg cctggctggg tcgagtactt tatcgccgct    1380
ctgagaggct gcgagctggt cgatctggct gatgaagtgg ccagcgtgta ccagagctac    1440
cagcctagaa ccagcgaccg gggcgagaat agcgaacagg ctctgcagac actgagcccc    1500
agagccattc ctagaaaccc tgatggcggc cctctggaaa gctctagtga tctggccgct    1560 ctgtccctc tgacaagctc tggacaccaa gagcaggata ccgagctggg cagcacacat    1620
acagccggcg ctacaagcag cctgacacct tctagaggcc ccgtgtctcc cagcgtgtca    1680
tttcagcctc tggccaggtc taccctagg gcttctagac tgcctggacc aacaggcagc    1740
gtggtgtcta ccggcacaag cttcagctct agctctcctg gactggctag tgccggtgcc    1800
gctgagggaa acaaggcgc cgaatctgat caggccgagc ctatcatctg tagcagcgga    1860
gcagaagccc ctgccaatag cctgcctagc aaggtgccaa ccacactgat gcccgtgaac    1920
acagtggccc tgaaggtgcc agctaatcct gcctccgtgt ccaccgtgcc ttctaagctg    1980
ccaaccagct ctaagccacc tggcgccgtg ccatctaacg ccctgacaaa tcctgctcca    2040
agcaagctgc ccatcaactc cacaagagcc ggcatggtgc cctctaaggt gcccacatct    2100
atggtgctga ccaaggtgtc cgccagcacc gtgccaacag atggcagctc cagaaacgag    2160
gaaacccctg ccgctcctac tcctgctggc gctacaggcg atcttctgc ttggctggat    2220 agcagcagcg agaacagagg cctgggcagc gagctttcta aacctggcgt gctggcttcc    2280
caggtggaca gccatttc cggctgcttt gaggacctgg ctatcagcgc ctctacaagc    2340
ctcggcatgg gaccttgtca cggccccgag gaaaacgagt acaagagcga gggcaccttc    2400
ggcatccacg tggccgagaa tcctagcatc caactgctgg aaggcaaccc cggacctcca    2460
gctgatccag atggcggacc aagacctcag gccgacagaa agttccaaga gcgcgaggtg    2520
ccctgccaca gaccttctcc a                                             2541
```

<210> SEQ ID NO 16
<211> LENGTH: 847
<212> TYPE: PRT
<213> ORGANISM: Artificial sequence
<220> FEATURE:
<223> OTHER INFORMATION: Fusion of LMP1 of Epstein Barr virus and IPS1
   of Homo sapiens

<400> SEQUENCE: 16

```
Met Asp Leu Asp Leu Glu Arg Gly Pro Pro Gly Pro Arg Arg Pro Pro
1               5                   10                  15

Arg Gly Pro Pro Leu Ser Ser Ile Gly Leu Ala Leu Leu Leu Leu Leu
            20                  25                  30

Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
    50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
    130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
            165                 170                 175

Phe Leu Ala Ile Leu Ile Trp Met Tyr Tyr His Gly Gln Arg His Ser
        180                 185                 190

Asp Glu His His His Asp Asp Ser Leu Pro His Pro Gln Gln Ala Thr
    195                 200                 205

Asp Asp Ser Ser Asn Gln Ser Asp Ser Asn Ser Asn Glu Gly Arg His
210                 215                 220

Leu Leu Leu Val Ser Gly Ala Gly Asp Gly Pro Pro Leu Cys Ser Gln
225                 230                 235                 240

Asn Leu Gly Ala Pro Gly Gly Pro Asn Asn Gly Pro Gln Asp Pro
            245                 250                 255

Asp Asn Thr Asp Asp Asn Gly Pro Gln Asp Pro Asp Asn Thr Asp Asp
        260                 265                 270

Asn Gly Pro His Asp Pro Leu Pro Gln Asp Pro Asp Asn Thr Asp Asp
    275                 280                 285

Asn Gly Pro Gln Asp Pro Asp Asn Thr Asp Asp Asn Gly Pro His Asp
290                 295                 300

Pro Leu Pro His Asn Pro Ser Asp Ser Ala Gly Asn Asp Gly Gly Pro
305                 310                 315                 320

Pro Gln Leu Thr Glu Glu Val Glu Asn Lys Gly Gly Asp Gln Gly Pro
            325                 330                 335

Pro Leu Met Thr Asp Gly Gly Gly His Ser His Asp Ser Gly His
        340                 345                 350

Asp Gly Ile Asp Pro His Leu Pro Thr Leu Leu Gly Thr Ser Gly
    355                 360                 365

Ser Gly Gly Asp Asp Asp Pro His Gly Pro Val Gln Leu Ser Tyr
370                 375                 380

Tyr Asp Pro Phe Ala Glu Asp Lys Thr Tyr Lys Tyr Ile Cys Arg Asn
385                 390                 395                 400
```

```
Phe Ser Asn Phe Cys Asn Val Asp Val Val Glu Ile Leu Pro Tyr Leu
                405                 410                 415
Pro Cys Leu Thr Ala Arg Asp Gln Asp Arg Leu Arg Ala Thr Cys Thr
            420                 425                 430
Leu Ser Gly Asn Arg Asp Thr Leu Trp His Leu Phe Asn Thr Leu Gln
        435                 440                 445
Arg Arg Pro Gly Trp Val Glu Tyr Phe Ile Ala Ala Leu Arg Gly Cys
    450                 455                 460
Glu Leu Val Asp Leu Ala Asp Glu Val Ala Ser Val Tyr Gln Ser Tyr
465                 470                 475                 480
Gln Pro Arg Thr Ser Asp Arg Gly Glu Asn Ser Glu Gln Ala Leu Gln
            485                 490                 495
Thr Leu Ser Pro Arg Ala Ile Pro Arg Asn Pro Asp Gly Gly Pro Leu
        500                 505                 510
Glu Ser Ser Ser Asp Leu Ala Ala Leu Ser Pro Leu Thr Ser Ser Gly
    515                 520                 525
His Gln Glu Gln Asp Thr Glu Leu Gly Ser Thr His Thr Ala Gly Ala
530                 535                 540
Thr Ser Ser Leu Thr Pro Ser Arg Gly Pro Val Ser Pro Ser Val Ser
545                 550                 555                 560
Phe Gln Pro Leu Ala Arg Ser Thr Pro Arg Ala Ser Arg Leu Pro Gly
            565                 570                 575
Pro Thr Gly Ser Val Val Ser Thr Gly Thr Ser Phe Ser Ser Ser Ser
        580                 585                 590
Pro Gly Leu Ala Ser Ala Gly Ala Glu Gly Lys Gln Gly Ala Glu
    595                 600                 605
Ser Asp Gln Ala Glu Pro Ile Ile Cys Ser Ser Gly Ala Glu Ala Pro
610                 615                 620
Ala Asn Ser Leu Pro Ser Lys Val Pro Thr Thr Leu Met Pro Val Asn
625                 630                 635                 640
Thr Val Ala Leu Lys Val Pro Ala Asn Pro Ala Ser Val Ser Thr Val
            645                 650                 655
Pro Ser Lys Leu Pro Thr Ser Ser Lys Pro Pro Gly Ala Val Pro Ser
        660                 665                 670
Asn Ala Leu Thr Asn Pro Ala Pro Ser Lys Leu Pro Ile Asn Ser Thr
    675                 680                 685
Arg Ala Gly Met Val Pro Ser Lys Val Pro Thr Ser Met Val Leu Thr
690                 695                 700
Lys Val Ser Ala Ser Thr Val Pro Thr Asp Gly Ser Ser Arg Asn Glu
705                 710                 715                 720
Glu Thr Pro Ala Ala Pro Thr Pro Ala Gly Ala Thr Gly Gly Ser Ser
            725                 730                 735
Ala Trp Leu Asp Ser Ser Ser Glu Asn Arg Gly Leu Gly Ser Glu Leu
        740                 745                 750
Ser Lys Pro Gly Val Leu Ala Ser Gln Val Asp Ser Pro Phe Ser Gly
    755                 760                 765
Cys Phe Glu Asp Leu Ala Ile Ser Ala Ser Thr Ser Leu Gly Met Gly
770                 775                 780
Pro Cys His Gly Pro Glu Glu Asn Glu Tyr Lys Ser Glu Gly Thr Phe
785                 790                 795                 800
Gly Ile His Val Ala Glu Asn Pro Ser Ile Gln Leu Leu Glu Gly Asn
            805                 810                 815
```

Pro Gly Pro Pro Ala Asp Pro Asp Gly Gly Pro Arg Pro Gln Ala Asp
          820                 825                 830

Arg Lys Phe Gln Glu Arg Glu Val Pro Cys His Arg Pro Ser Pro
    835                 840                 845

<210> SEQ ID NO 17
<211> LENGTH: 2697
<212> TYPE: DNA
<213> ORGANISM: Artificial sequence
<220> FEATURE:
<223> OTHER INFORMATION: Fusion of LMP1 of Epstein Barr virus and IPS1
      of Homo sapiens

<400> SEQUENCE: 17

| | | | | | | |
|---|---|---|---|---|---|---|
| atggatctgg | acctggaaag | aggacctcct | ggacctagac | ggcctcctag | aggaccacct | 60 |
| ctgagcagct | ctattggact | ggccctgctg | ctgcttctgc | tggctctgct | gttctggctg | 120 |
| tacatcatca | tgagcaactg | accggcgga | gcactgctgg | tgctgtatgc | ctttgctctg | 180 |
| atgctggtca | tcatcatcct | gatcatcttc | atcttccggc | gggacctgct | gtgtcctctg | 240 |
| ggagcactt | gtctgttgct | gctgatgatc | accctcctgc | tgatcgccct | gtggaacctg | 300 |
| catggacagg | ccctgtatct | gggaatcgtg | ctgttcatct | tcggctgcct | gctggttctc | 360 |
| ggcctgtgga | tctacctgct | ggaaatcctt | tggagactgg | gcgccaccat | ctggcagctg | 420 |
| ctggcctttt | tcctggcctt | ctttctggat | atcatcctcc | tcatcattgc | cctgtacctg | 480 |
| cagcagaact | ggtggaccct | gctggtggat | ctgctttggc | tgctgctctt | tctggccatc | 540 |
| ctgatttgga | tgtactacca | cggccagcgg | cacagcgacg | aacaccacca | tgatgacagc | 600 |
| ctgcctcatc | ctcagcaggc | caccgacgat | agcagcaacc | agagcgacag | caacagcaac | 660 |
| gagggcagac | atctgctgct | ggtgtctggt | gctggcgacg | gacctcctct | gtgttctcaa | 720 |
| aatcttggcg | ccccctggcgg | cggaccaaac | aatggacctc | aggaccccga | caacaccgac | 780 |
| gacaatggcc | ctcaagatcc | tgataatacc | gatgacaacg | cccacacga | ccctctgcct | 840 |
| caagacccag | ataacacaga | cgataacggt | ccacaagatc | cggacaatac | tgacgataat | 900 |
| ggaccccacg | atccactgcc | tcacaaccct | agcgatagcg | ccggaaatga | tgcggacct | 960 |
| ccacagctga | ccgaggaagt | ggaaaacaaa | ggcgagatc | agggccctcc | tctgatgacc | 1020 |
| gatggcggag | tggacactc | tcacgattct | ggccacgacg | gcatcgaccc | tcatctgcct | 1080 |
| acactgctgc | tcggcacatc | tggctctggc | ggcgacgatg | atgatcctca | tggacctgtg | 1140 |
| cagctgagct | actacgaccc | ttctccaaga | cactgcccag | tggaaagaga | gcagttcaag | 1200 |
| agggacgccc | agcctagacc | tggcggagat | cctgatgctc | cacctggacc | aaatggcgag | 1260 |
| ctgctgcaga | tcagccctaa | tgaggccgtg | cacatcggct | tcaccggcga | gtctaagtac | 1320 |
| gagaacgagg | aacccggcca | ctgtcctggc | atgggccttt | ctacatctgc | ctctatcgcc | 1380 |
| ctggacgagt | tctgcggcag | ctttccatct | gatgtgcagt | ctgccctcgt | gggccctaag | 1440 |
| tctctggaat | ctggcctggg | cagaaacgag | agcagctccg | atctgtgggc | tagctctggt | 1500 |
| ggaacagctg | gcgctcctac | accagccgct | cctaccgaag | agaatagaag | cagcggcgac | 1560 |
| accctgtga | caagcgcctc | tgtgaaaacc | ctggtcatga | gcaccccagt | gaagtcccca | 1620 |
| gtgatgggcg | ccagaacctc | caacattccc | ctgagtctc | ccgctcctaa | cacactggcc | 1680 |
| aactctccag | tggctggccc | tcctaagtct | agcacccctc | tgaaaagccc | cgtgacctct | 1740 |
| gtgtctgccc | ctaacgctcc | tgtgaaactg | ccgtgacca | acgtgccat | gctgaccaca | 1800 |
| cctgtgaaat | ccccactgag | caatgcccct | gccgaggccg | gaagctcttg | tatcattccc | 1860 |

```
gaggctcagg atagcgaggc tggccaaaaa ggcgaagctg caggcgcttc tgctctgggc    1920
cctagctcta gctcttttag caccggcacc agcgtggtgt ctggcacacc aggacctctg    1980
agaagcgcca gacctacctc tagagccctg cctcagttta gcgtgtcccc tagtgtgcct    2040
ggcagaagcc ctacactgtc tagtacagcc ggcgctacac acaccagcgg actggaaaca    2100
gaccaagaac agcatggcag cagcaccctg ccttctctgg ctgcccttga ttctagcagc    2160
gaactgccag gcggcgaccc caatagacct atcgctagac ctagcctgac acagctggcc    2220
caagagagca atgagggccc ttctgagcct gctcagaccg aacaggtgcc aatgccttac    2280
agccccgaga agagcggtg cagcaactac cctatcagcc atgccgctgc tcccacacct    2340
cctggtccaa gagaagctcc tctgagccct cctgagctgc ccgatcctcc aagagatagc    2400
accagacctc agtactccca gtacgtgtcc gccgtggaag atgccctgga tgtgctggaa    2460
tgtggcagac tggccgccat cttctacgaa gtgtggggcc ctagaaggca gctgaccaac    2520
tttctgcact ggctgaccga cagaaacggc agcctgacat gtaccgccag actgagagat    2580
caggaccggg ccacactgtg ccctctgtat cctctgatcg aggtggtgga cgtgaactgc    2640
ttcaacagct tcaaccggtg catctacaag tacaccaagg acgaggcttt ccctatg      2697
```

<210> SEQ ID NO 18
<211> LENGTH: 899
<212> TYPE: PRT
<213> ORGANISM: Artificial sequence
<220> FEATURE:
<223> OTHER INFORMATION: Fusion of LMP1 of Epstein Barr virus and IPS1
      of Homo sapiens

<400> SEQUENCE: 18

```
Met Asp Leu Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
            20                  25                  30

Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
    50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
    130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu
                165                 170                 175

Phe Leu Ala Ile Leu Ile Trp Met Tyr Tyr His Gly Gln Arg His Ser
            180                 185                 190

Asp Glu His His His Asp Asp Ser Leu Pro His Pro Gln Gln Ala Thr
        195                 200                 205
```

```
Asp Asp Ser Ser Asn Gln Ser Asp Ser Asn Ser Asn Glu Gly Arg His
            210                 215                 220

Leu Leu Leu Val Ser Gly Ala Gly Asp Gly Pro Pro Leu Cys Ser Gln
225                 230                 235                 240

Asn Leu Gly Ala Pro Gly Gly Pro Asn Asn Gly Pro Gln Asp Pro
                245                 250                 255

Asp Asn Thr Asp Asp Asn Gly Pro Gln Asp Pro Asp Asn Thr Asp Asp
            260                 265                 270

Asn Gly Pro His Asp Pro Leu Pro Gln Asp Pro Asp Asn Thr Asp Asp
            275                 280                 285

Asn Gly Pro Gln Asp Pro Asp Asn Thr Asp Asp Asn Gly Pro His Asp
            290                 295                 300

Pro Leu Pro His Asn Pro Ser Asp Ser Ala Gly Asn Asp Gly Gly Pro
305                 310                 315                 320

Pro Gln Leu Thr Glu Glu Val Glu Asn Lys Gly Gly Asp Gln Gly Pro
                325                 330                 335

Pro Leu Met Thr Asp Gly Gly Gly His Ser His Asp Ser Gly His
            340                 345                 350

Asp Gly Ile Asp Pro His Leu Pro Thr Leu Leu Gly Thr Ser Gly
            355                 360                 365

Ser Gly Gly Asp Asp Asp Pro His Gly Pro Val Gln Leu Ser Tyr
    370                 375                 380

Tyr Asp Pro Ser Pro Arg His Cys Pro Val Glu Arg Glu Gln Phe Lys
385                 390                 395                 400

Arg Asp Ala Gln Pro Arg Pro Gly Gly Asp Pro Asp Ala Pro Pro Gly
                405                 410                 415

Pro Asn Gly Glu Leu Leu Gln Ile Ser Pro Asn Glu Ala Val His Ile
            420                 425                 430

Gly Phe Thr Gly Glu Ser Lys Tyr Glu Asn Glu Glu Pro Gly His Cys
            435                 440                 445

Pro Gly Met Gly Leu Ser Thr Ser Ala Ser Ile Ala Leu Asp Glu Phe
450                 455                 460

Cys Gly Ser Phe Pro Ser Asp Val Gln Ser Ala Leu Val Gly Pro Lys
465                 470                 475                 480

Ser Leu Glu Ser Gly Leu Gly Arg Asn Glu Ser Ser Ser Asp Leu Trp
                485                 490                 495

Ala Ser Ser Gly Gly Thr Ala Gly Ala Pro Thr Pro Ala Ala Pro Thr
                500                 505                 510

Glu Glu Asn Arg Ser Ser Gly Asp Thr Pro Val Thr Ser Ala Ser Val
            515                 520                 525

Lys Thr Leu Val Met Ser Thr Pro Val Lys Ser Pro Val Met Gly Ala
530                 535                 540

Arg Thr Ser Asn Ile Pro Leu Lys Ser Pro Ala Pro Asn Thr Leu Ala
545                 550                 555                 560

Asn Ser Pro Val Ala Gly Pro Pro Lys Ser Ser Thr Pro Leu Lys Ser
                565                 570                 575

Pro Val Thr Ser Val Ser Ala Pro Asn Ala Pro Val Lys Leu Ala Val
            580                 585                 590

Thr Asn Val Pro Met Leu Thr Thr Pro Val Lys Ser Pro Leu Ser Asn
            595                 600                 605

Ala Pro Ala Glu Ala Gly Ser Ser Cys Ile Ile Pro Glu Ala Gln Asp
610                 615                 620
```

```
Ser Glu Ala Gly Gln Lys Gly Glu Ala Ala Gly Ser Ala Leu Gly
625                 630                 635                 640

Pro Ser Ser Ser Phe Ser Thr Gly Thr Ser Val Val Ser Gly Thr
            645                 650                 655

Pro Gly Pro Leu Arg Ser Ala Arg Pro Thr Ser Arg Ala Leu Pro Gln
        660                 665                 670

Phe Ser Val Ser Pro Ser Val Pro Gly Arg Ser Pro Thr Leu Ser Ser
    675                 680                 685

Thr Ala Gly Ala Thr His Thr Ser Gly Leu Glu Thr Asp Gln Glu Gln
690                 695                 700

His Gly Ser Ser Thr Leu Pro Ser Leu Ala Ala Leu Asp Ser Ser Ser
705                 710                 715                 720

Glu Leu Pro Gly Gly Asp Pro Asn Arg Pro Ile Ala Arg Pro Ser Leu
                725                 730                 735

Thr Gln Leu Ala Gln Glu Ser Asn Glu Gly Pro Ser Glu Pro Ala Gln
            740                 745                 750

Thr Glu Gln Val Pro Met Pro Tyr Ser Pro Glu Lys Glu Arg Cys Ser
        755                 760                 765

Asn Tyr Pro Ile Ser His Ala Ala Ala Pro Thr Pro Pro Gly Pro Arg
    770                 775                 780

Glu Ala Pro Leu Ser Pro Pro Glu Leu Pro Asp Pro Pro Arg Asp Ser
785                 790                 795                 800

Thr Arg Pro Gln Tyr Ser Gln Tyr Val Ser Ala Val Glu Asp Ala Leu
                805                 810                 815

Asp Val Leu Glu Cys Gly Arg Leu Ala Ala Ile Phe Tyr Glu Val Trp
            820                 825                 830

Gly Pro Arg Arg Gln Leu Thr Asn Phe Leu His Trp Leu Thr Asp Arg
        835                 840                 845

Asn Gly Ser Leu Thr Cys Thr Ala Arg Leu Arg Asp Gln Asp Arg Ala
    850                 855                 860

Thr Leu Cys Pro Leu Tyr Pro Leu Ile Glu Val Val Asp Val Asn Cys
865                 870                 875                 880

Phe Asn Ser Phe Asn Arg Cys Ile Tyr Lys Tyr Thr Lys Asp Glu Ala
                885                 890                 895

Phe Pro Met

<210> SEQ ID NO 19
<211> LENGTH: 2694
<212> TYPE: DNA
<213> ORGANISM: Artificial sequence
<220> FEATURE:
<223> OTHER INFORMATION: Fusion of LMP1 of Epstein Barr virus and IPS1
      of Homo sapiens

<400> SEQUENCE: 19
atggatctgg atctcgaaag aggacctcct ggacctagac ggcctcctag aggaccacct      60
ctgagcagct ctattggact ggccctgctg ctgcttctgc tggctctgct gttctggctg     120
tacatcatca tgagcaactg gaccggcgga gcactgctgg tgctgtatgc ctttgctctg     180
atgctggtca tcatcatcct gatcatcttc atcttccggc gggacctgct gtgtcctctg     240
ggagcacttt gtctgttgct gctgatgatc accctcctgc tgatcgccct gtggaacctg     300
catggacagg ccctgtatct gggcatcgtg ctgttcatct tcggctgcct gctggttctc     360
ggctgtggaa tctacctgct ggaaatcctt tggagactgg cgccaccat ctggcagctg     420 ctggcctttt tcctggcctt ctttctggat atcatcctcc tcatcattgc cctgtacctg     480
```

```
cagcagaact ggtggaccct gctggtggat ctgctttggc tgctgctctt tctggccatc    540
ctgatttgga tgtactacca cggccagcgg cctttcgccg aggacaagac ctacaagtac    600
atctgccgga acttcagcaa cttctgcaac gtggacgtgg tggaaattct gccctacctg    660
ccttgcctga ccgccagaga tcaggacaga ctgagagcca catgtaccct gagcggcaac    720
agagacacac tgtggcacct gttcaacacc ctgcagagaa ggcctggctg ggtcgagtac    780
tttatcgccg ctctgagagg ctgcgagctg gtcgatctgg ctgatgaagt ggccagcgtg    840
taccagagct accagcctag aaccagcgac cggcctcctg atcctctcga acctccatct    900
ctgcccgcca aagacctgga acctcctaca ccagctgccg ctcacagcat cccttacaac    960
agctgcagag agaaagaacc tagctacccc atgcctgtgc aagagacaca ggccccagaa   1020
agccctggcg agaatagcga acaggctctg cagacactga gccccagagc cattcctaga   1080
aaccctgatg gcggccctct ggaaagctct agtgatctgg ccgctctgtc ccctctgaca   1140
agctctggac accaagagca ggataccgag ctgggcagca cacatacagc cggcgctaca   1200
agcagcctga caccttctag aggccccgtg tctcccagcg tgtcatttca gcctctggcc   1260
aggtctaccc ctagggcttc tagactgcct ggaccaacag gcagcgtggt gtctaccggc   1320
acaagcttca gctctagctc tcctggactg gctagtgccg gtgccgctga gggaaaacaa   1380
ggcgccgaat ctgatcaggc cgagcctatc atctgtagca gcggagcaga agcccctgcc   1440
aatagcctgc ctagcaaggt gccaaccaca ctgatgcccg tgaacacagt ggccctgaag   1500
gtgccagcta atcctgcctc cgtgtccacc gtgccttcta agctgccaac cagctctaag   1560
ccacctggcg ccgtgccatc taacgccctg acaaatcctg ctccaagcaa gctgcccatc   1620
aactccacaa gagccggcat ggtgccctct aaggtgccca catctatggt gctgaccaag   1680
gtgtccgcca gcaccgtgcc aacagatggc agctccagaa cgaggaaac cctgccgct   1740 cctactcctg ctggcgctac aggcggatct tctgcttggc tggatagcag cagcgagaac   1800
agaggcctgg gcagcgagct ttctaaacct ggcgtgctgg cttcccaggt ggacagccca   1860
ttttccggct gctttgagga cctggctatc agcgcctcta caagcctcgg catgggacct   1920
tgtcacggcc ccgaggaaaa cgagtacaag agcgagggca ccttcggcat ccacgtggcc   1980
gagaatccta gcatccaact gctggaaggc aaccccggac ctccagctga tccagatggc   2040
ggaccaagac ctcaggccga cagaaagttc aagagcgcg aggtgccctg ccacagacct   2100
tctccacaca cgacgaaca ccaccatgat gacagcctgc ctcatcctca gcaggccacc   2160
gacgatagca gcaaccagag cgacagcaac agcaacgagg cagacatct gctgctggtg   2220 tctggtgctg gcgacggacc tcctctgtgt tctcaaaatc ttggcgcccc tggcggcgga   2280
ccaaacaatg gacctcagga ccccgacaac accgacgaca atggccctca agatcctgat   2340
aataccgatg acaacggccc acacgaccct ctgcctcaag acccagataa cacagacgat   2400
aacggtccac aagatccgga caatactgac gataatggac cccacgatcc actgcctcac   2460
aaccctagcg atagcgccgg aaatgatggc ggacctccac agctgaccga ggaagtggaa   2520
aacaaaggcg gagatcaggg ccctcctctg atgaccgatg gcggaggtgg acactctcac   2580
gattctggcc acgacggcat cgaccctcat ctgcctacac tgctgctcgg cacatctggc   2640
tctggcggcg acgatgatga tcctcatgga cctgtgcagc tgagctacta cgac         2694
```

<210> SEQ ID NO 20
<211> LENGTH: 898
<212> TYPE: PRT

<213> ORGANISM: Artificial sequence
<220> FEATURE:
<223> OTHER INFORMATION: Fusion of LMP1 of Epstein Barr virus and IPS1 of Homo sapieins

<400> SEQUENCE: 20

```
Met Asp Leu Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
            20                  25                  30

Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
    50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
    130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
            165                 170                 175

Phe Leu Ala Ile Leu Ile Trp Met Tyr Tyr His Gly Gln Arg Pro Phe
        180                 185                 190

Ala Glu Asp Lys Thr Tyr Lys Tyr Ile Cys Arg Asn Phe Ser Asn Phe
    195                 200                 205

Cys Asn Val Asp Val Val Glu Ile Leu Pro Tyr Leu Pro Cys Leu Thr
210                 215                 220

Ala Arg Asp Gln Asp Arg Leu Arg Ala Thr Cys Thr Leu Ser Gly Asn
225                 230                 235                 240

Arg Asp Thr Leu Trp His Leu Phe Asn Thr Leu Gln Arg Arg Pro Gly
            245                 250                 255

Trp Val Glu Tyr Phe Ile Ala Ala Leu Arg Gly Cys Glu Leu Val Asp
        260                 265                 270

Leu Ala Asp Glu Val Ala Ser Val Tyr Gln Ser Tyr Gln Pro Arg Thr
    275                 280                 285

Ser Asp Arg Pro Pro Asp Pro Leu Glu Pro Pro Ser Leu Pro Ala Glu
290                 295                 300

Arg Pro Gly Pro Pro Thr Pro Ala Ala Ala His Ser Ile Pro Tyr Asn
305                 310                 315                 320

Ser Cys Arg Glu Lys Glu Pro Ser Tyr Pro Met Pro Val Gln Glu Thr
            325                 330                 335

Gln Ala Pro Glu Ser Pro Gly Glu Asn Ser Glu Gln Ala Leu Gln Thr
        340                 345                 350

Leu Ser Pro Arg Ala Ile Pro Arg Asn Pro Asp Gly Gly Pro Leu Glu
    355                 360                 365

Ser Ser Ser Asp Leu Ala Ala Leu Ser Pro Leu Thr Ser Ser Gly His
370                 375                 380
```

```
Gln Glu Gln Asp Thr Glu Leu Gly Ser Thr His Thr Ala Gly Ala Thr
385                 390                 395                 400

Ser Ser Leu Thr Pro Ser Arg Gly Pro Val Ser Pro Ser Val Ser Phe
        405                 410                 415

Gln Pro Leu Ala Arg Ser Thr Pro Arg Ala Ser Arg Leu Pro Gly Pro
        420                 425                 430

Thr Gly Ser Val Val Ser Thr Gly Thr Ser Phe Ser Ser Ser Ser Pro
        435                 440                 445

Gly Leu Ala Ser Ala Gly Ala Ala Glu Gly Lys Gln Gly Ala Glu Ser
        450                 455                 460

Asp Gln Ala Glu Pro Ile Ile Cys Ser Ser Gly Ala Glu Ala Pro Ala
465                 470                 475                 480

Asn Ser Leu Pro Ser Lys Val Pro Thr Thr Leu Met Pro Val Asn Thr
        485                 490                 495

Val Ala Leu Lys Val Pro Ala Asn Pro Ala Ser Val Ser Thr Val Pro
        500                 505                 510

Ser Lys Leu Pro Thr Ser Ser Lys Pro Gly Ala Val Pro Ser Asn
        515                 520                 525

Ala Leu Thr Asn Pro Ala Pro Ser Lys Leu Pro Ile Asn Ser Thr Arg
        530                 535                 540

Ala Gly Met Val Pro Ser Lys Val Pro Thr Ser Met Val Leu Thr Lys
545                 550                 555                 560

Val Ser Ala Ser Thr Val Pro Thr Asp Gly Ser Ser Arg Asn Glu Glu
                565                 570                 575

Thr Pro Ala Ala Pro Thr Pro Ala Gly Ala Thr Gly Gly Ser Ser Ala
        580                 585                 590

Trp Leu Asp Ser Ser Ser Glu Asn Arg Gly Leu Gly Ser Glu Leu Ser
        595                 600                 605

Lys Pro Gly Val Leu Ala Ser Gln Val Asp Ser Pro Phe Ser Gly Cys
        610                 615                 620

Phe Glu Asp Leu Ala Ile Ser Ala Ser Thr Ser Leu Gly Met Gly Pro
625                 630                 635                 640

Cys His Gly Pro Glu Glu Asn Glu Tyr Lys Ser Glu Gly Thr Phe Gly
        645                 650                 655

Ile His Val Ala Glu Asn Pro Ser Ile Gln Leu Leu Glu Gly Asn Pro
        660                 665                 670

Gly Pro Pro Ala Asp Pro Asp Gly Gly Pro Arg Pro Gln Ala Asp Arg
        675                 680                 685

Lys Phe Gln Glu Arg Glu Val Pro Cys His Arg Pro Ser Pro His Ser
        690                 695                 700

Asp Glu His His His Asp Asp Ser Leu Pro His Pro Gln Gln Ala Thr
705                 710                 715                 720

Asp Asp Ser Ser Asn Gln Ser Asp Ser Asn Ser Asn Glu Gly Arg His
                725                 730                 735

Leu Leu Leu Val Ser Gly Ala Gly Asp Gly Pro Pro Leu Cys Ser Gln
        740                 745                 750

Asn Leu Gly Ala Pro Gly Gly Pro Asn Asn Gly Pro Gln Asp Pro
        755                 760                 765

Asp Asn Thr Asp Asp Asn Gly Pro Gln Asp Pro Asn Thr Asp Asp
        770                 775                 780

Asn Gly Pro His Asp Pro Leu Pro Gln Asp Pro Asp Asn Thr Asp Asp
785                 790                 795                 800
```

Asn Gly Pro Gln Asp Pro Asp Asn Thr Asp Asp Asn Gly Pro His Asp
            805                 810                 815

Pro Leu Pro His Asn Pro Ser Asp Ser Ala Gly Asn Asp Gly Gly Pro
        820                 825                 830

Pro Gln Leu Thr Glu Glu Val Glu Asn Lys Gly Gly Asp Gln Gly Pro
    835                 840                 845

Pro Leu Met Thr Asp Gly Gly Gly Gly His Ser His Asp Ser Gly His
850                 855                 860

Asp Gly Ile Asp Pro His Leu Pro Thr Leu Leu Leu Gly Thr Ser Gly
865                 870                 875                 880

Ser Gly Gly Asp Asp Asp Pro His Gly Pro Val Gln Leu Ser Tyr
                885                 890                 895

Tyr Asp

<210> SEQ ID NO 21
<211> LENGTH: 2541
<212> TYPE: DNA
<213> ORGANISM: Artificial sequence
<220> FEATURE:
<223> OTHER INFORMATION: Fusion of LMP1 of Epstein Barr virus and IPS1
      of Homo sapiens

<400> SEQUENCE: 21

| | |
|---|---|
| atggatctgg atctcgaaag aggacctcct ggacctagac ggcctcctag aggaccacct | 60 |
| ctgagcagct ctattggact ggccctgctg ctgcttctgc tggctctgct gttctggctg | 120 |
| tacatcatca tgagcaactg gaccggcgga gcactgctgg tgctgtatgc ctttgctctg | 180 |
| atgctggtca tcatcatcct gatcatcttc atcttccggc gggacctgct gtgtcctctg | 240 |
| ggagcacttt gtctgttgct gctgatgatc accctcctgc tgatcgccct gtggaacctg | 300 |
| catggacagg ccctgtatct gggcatcgtg ctgttcatct tcggctgcct gctggttctc | 360 |
| ggcctgtgga tctacctgct ggaaatcctt tggagactgg cgccaccat ctggcagctg | 420 |
| ctggcctttt tcctggcctt ctttctggat atcatcctcc tcatcattgc cctgtacctg | 480 |
| cagcagaact ggtggaccct gctggtggat ctgctttggc tgctgctctt tctggccatc | 540 |
| ctgatttgga tgtactacca cggccagcgg cctttcgccg aggacaagac ctacaagtac | 600 |
| atctgccgga cttcagcaa cttctgcaac gtggacgtgg tggaaattct gccctacctg | 660 |
| ccttgcctga ccgccagaga tcaggacaga ctgagagcca catgtaccct gagcggcaac | 720 |
| agagacacac tgtggcacct gttcaacacc ctgcagagaa ggcctggctg ggtcgagtac | 780 |
| tttatcgccg ctctgagagg ctgcgagctg gtcgatctgg ctgatgaagt ggccagcgtg | 840 |
| taccagagct accagcctag aaccagcgac cggggcgaga atagcgaaca ggctctgcag | 900 |
| acactgagcc ccagagccat tcctagaaac cctgatggcg cccctctgga aagctctagt | 960 |
| gatctggccg ctctgtcccc tctgacaagc tctggacacc aagagcagga taccgagctg | 1020 |
| ggcagcacac atacagccgg cgctacaagc agcctgacac cttctagagg ccccgtgtct | 1080 |
| cccagcgtgt catttcagcc tctggccagg tctaccccta gggcttctag actgcctgga | 1140 |
| ccaacaggca gcgtggtgtc taccggcaca agcttcagct ctagctctcc tggactggct | 1200 |
| agtgccggtg ccgctgaggg aaaacaaggc gccgaatctg atcaggccga gcctatcatc | 1260 |
| tgtagcagcg gagcagaagc ccctgccaat agcctgccta gcaaggtgcc aaccacactg | 1320 |
| atgcccgtga acagtggc cctgaaggtg ccagctaatc tgcctccgt gtccaccgtg | 1380 |
| ccttctaagc tgccaaccag ctctaagcca cctggcgccg tgccatctaa cgccctgaca | 1440 |

```
aatcctgctc caagcaagct gcccatcaac tccacaagag ccggcatggt gccctctaag    1500
gtgcccacat ctatggtgct gaccaaggtg tccgccagca ccgtgccaac agatggcagc    1560
tccagaaacg aggaaacccc tgccgctcct actcctgctg gcgctacagg cggatcttct    1620
gcttggctgg atagcagcag cgagaacaga ggcctgggca gcgagctttc taaacctggc    1680
gtgctggctt cccaggtgga cagcccattt tccggctgct ttgaggacct ggctatcagc    1740
gcctctacaa gcctcggcat gggaccttgt cacggcccg aggaaaacga gtacaagagc     1800
gagggcacct tcggcatcca cgtggccgag aatcctagca tccaactgct ggaaggcaac    1860 cccgacctc cagctgatcc agatggcgga ccaagacctc aggccgacag aaagttccaa     1920
gagcgcgagg tgccctgcca cagaccttct ccacacagcg acgaacacca ccatgatgac    1980
agcctgcctc atcctcagca ggccaccgac gatagcagca accagagcga cagcaacagc    2040
aacgagggca gacatctgct gctggtgtct ggtgctggcg acggacctcc tctgtgttct    2100
caaaatcttg gcgcccctgg cggcggacca aacaatggac tcaggaccc cgacaacacc     2160 gacgacaatg gcctcaagaa tcctgataat accgatgaca acggcccaca cgaccctctg    2220
cctcaagacc cagataacac agacgataac ggtccacaag atccggacaa tactgacgat    2280
aatggacccc acgatccact gcctcacaac cctagcgata gcgccggaaa tgatggcgga    2340
cctccacagc tgaccgagga gtggaaaac aaaggcggag atcagggccc tcctctgatg     2400
accgatggcg gaggtggaca ctctcacgat tctggccacg acggcatcga ccctcatctg    2460
cctacactgc tgctcggcac atctggctct ggcggcgacg atgatgatcc tcatggacct    2520
gtgcagctga gctactacga c                                              2541
```

<210> SEQ ID NO 22
<211> LENGTH: 847
<212> TYPE: PRT
<213> ORGANISM: Artificial sequence
<220> FEATURE:
<223> OTHER INFORMATION: Fusion of LMP1 of Epstein Barr virus and IPS1
      of Homo sapiens

<400> SEQUENCE: 22

```
Met Asp Leu Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
                20                  25                  30

Leu Leu Ala Leu Leu Phe Trp Leu Tyr Ile Ile Met Ser Asn Trp Thr
            35                  40                  45

Gly Gly Ala Leu Leu Val Leu Tyr Ala Phe Ala Leu Met Leu Val Ile
        50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
    130                 135                 140

Leu Ala Phe Phe Leu Asp Ile Ile Leu Leu Ile Ile Ala Leu Tyr Leu
145                 150                 155                 160
```

```
Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Pro Phe
            180                 185                 190

Ala Glu Asp Lys Thr Tyr Lys Tyr Ile Cys Arg Asn Phe Ser Asn Phe
        195                 200                 205

Cys Asn Val Asp Val Val Glu Ile Leu Pro Tyr Leu Pro Cys Leu Thr
    210                 215                 220

Ala Arg Asp Gln Asp Arg Leu Arg Ala Thr Cys Thr Leu Ser Gly Asn
225                 230                 235                 240

Arg Asp Thr Leu Trp His Leu Phe Asn Thr Leu Gln Arg Arg Pro Gly
                245                 250                 255

Trp Val Glu Tyr Phe Ile Ala Ala Leu Arg Gly Cys Glu Leu Val Asp
            260                 265                 270

Leu Ala Asp Glu Val Ala Ser Val Tyr Gln Ser Tyr Gln Pro Arg Thr
        275                 280                 285

Ser Asp Arg Gly Glu Asn Ser Glu Gln Ala Leu Gln Thr Leu Ser Pro
    290                 295                 300

Arg Ala Ile Pro Arg Asn Pro Asp Gly Gly Pro Leu Glu Ser Ser Ser
305                 310                 315                 320

Asp Leu Ala Ala Leu Ser Pro Leu Thr Ser Ser Gly His Gln Glu Gln
                325                 330                 335

Asp Thr Glu Leu Gly Ser Thr His Thr Ala Gly Ala Thr Ser Ser Leu
            340                 345                 350

Thr Pro Ser Arg Gly Pro Val Ser Pro Ser Val Ser Phe Gln Pro Leu
        355                 360                 365

Ala Arg Ser Thr Pro Arg Ala Ser Arg Leu Pro Gly Pro Thr Gly Ser
    370                 375                 380

Val Val Ser Thr Gly Thr Ser Phe Ser Ser Ser Pro Gly Leu Ala
385                 390                 395                 400

Ser Ala Gly Ala Ala Glu Gly Lys Gln Gly Ala Glu Ser Asp Gln Ala
                405                 410                 415

Glu Pro Ile Ile Cys Ser Ser Gly Ala Glu Ala Pro Ala Asn Ser Leu
            420                 425                 430

Pro Ser Lys Val Pro Thr Thr Leu Met Pro Val Asn Thr Val Ala Leu
        435                 440                 445

Lys Val Pro Ala Asn Pro Ala Ser Val Ser Thr Val Pro Ser Lys Leu
    450                 455                 460

Pro Thr Ser Ser Lys Pro Pro Gly Ala Val Pro Ser Asn Ala Leu Thr
465                 470                 475                 480

Asn Pro Ala Pro Ser Lys Leu Pro Ile Asn Ser Thr Arg Ala Gly Met
                485                 490                 495

Val Pro Ser Lys Val Pro Thr Ser Met Val Leu Thr Lys Val Ser Ala
            500                 505                 510

Ser Thr Val Pro Thr Asp Gly Ser Ser Arg Asn Glu Thr Pro Ala
        515                 520                 525

Ala Pro Thr Pro Ala Gly Ala Thr Gly Gly Ser Ala Trp Leu Asp
    530                 535                 540

Ser Ser Ser Glu Asn Arg Gly Leu Gly Ser Glu Leu Ser Lys Pro Gly
545                 550                 555                 560

Val Leu Ala Ser Gln Val Asp Ser Pro Phe Ser Gly Cys Phe Glu Asp
                565                 570                 575
```

```
Leu Ala Ile Ser Ala Ser Thr Ser Leu Gly Met Gly Pro Cys His Gly
            580                 585                 590

Pro Glu Glu Asn Glu Tyr Lys Ser Glu Gly Thr Phe Gly Ile His Val
        595                 600                 605

Ala Glu Asn Pro Ser Ile Gln Leu Leu Glu Gly Asn Pro Gly Pro Pro
    610                 615                 620

Ala Asp Pro Asp Gly Gly Pro Arg Pro Gln Ala Asp Arg Lys Phe Gln
625                 630                 635                 640

Glu Arg Glu Val Pro Cys His Arg Pro Ser Pro His Ser Asp Glu His
                645                 650                 655

His His Asp Asp Ser Leu Pro His Pro Gln Gln Ala Thr Asp Asp Ser
            660                 665                 670

Ser Asn Gln Ser Asp Ser Asn Ser Asn Glu Gly Arg His Leu Leu Leu
        675                 680                 685

Val Ser Gly Ala Gly Asp Gly Pro Pro Leu Cys Ser Gln Asn Leu Gly
    690                 695                 700

Ala Pro Gly Gly Gly Pro Asn Asn Gly Pro Gln Asp Pro Asp Asn Thr
705                 710                 715                 720

Asp Asp Asn Gly Pro Gln Asp Pro Asp Asn Thr Asp Asn Gly Pro
                725                 730                 735

His Asp Pro Leu Pro Gln Asp Pro Asp Asn Thr Asp Asn Gly Pro
            740                 745                 750

Gln Asp Pro Asp Asn Thr Asp Asn Gly Pro His Asp Pro Leu Pro
        755                 760                 765

His Asn Pro Ser Asp Ser Ala Gly Asn Asp Gly Pro Pro Gln Leu
    770                 775                 780

Thr Glu Glu Val Glu Asn Lys Gly Gly Asp Gln Gly Pro Pro Leu Met
785                 790                 795                 800

Thr Asp Gly Gly Gly His Ser His Asp Ser Gly His Asp Gly Ile
            805                 810                 815

Asp Pro His Leu Pro Thr Leu Leu Gly Thr Ser Gly Ser Gly Gly
        820                 825                 830

Asp Asp Asp Asp Pro His Gly Pro Val Gln Leu Ser Tyr Tyr Asp
835                 840                 845

<210> SEQ ID NO 23
<211> LENGTH: 2697
<212> TYPE: DNA
<213> ORGANISM: Artificial sequence
<220> FEATURE:
<223> OTHER INFORMATION: Fusion of LMP1 of Epstein Barr virus and IPS1
      of Homo sapiens

<400> SEQUENCE: 23
atggatctgg atctcgaaag aggacctcct ggacctagac ggcctcctag aggaccacct      60
ctgagcagct ctattggact ggccctgctg ctgcttctgc tggctctgct gttctggctg     120
tacatcatca tgagcaactg gaccggcgga gcactgctgg tgctgtatgc ctttgctctg     180
atgctggtca tcatcatcct gatcatcttc atcttccggc gggacctgct gtgtcctctg     240
ggagcacttt gtctgttgct gctgatgatc accctcctgc tgatcgccct gtggaacctg     300
catggacagg ccctgtatct gggcatcgtg ctgttcatct tcggctgcct gctggttctc     360
ggcctgtgga tctacctgct ggaaatcctt tggagactgg cgccaccat ctggcagctg     420 ctggcctttt tcctgccctt ctttctggat atcatcctcc tcatcattgc cctgtacctg     480
cagcagaact ggtggaccct gctggtggat ctgctttggc tgctgctctt tctggccatc     540
```

```
ctgatttgga tgtactacca cggccagcgg ccttctccaa gacactgccc agtggaaaga    600
gagcagttca agagggacgc ccagcctaga cctggcggag atcctgatgc tccacctgga    660
ccaaatggcg agctgctgca gatcagccct aatgaggccg tgcacatcgg cttcaccggc    720
gagtctaagt acgagaacga ggaacccggc cactgtcctg gcatgggcct ttctacatct    780
gcctctatcg ccctggacga gttctgcggc agctttccat ctgatgtgca gtctgccctc    840
gtgggcccta gtctctgga atctggcctg gcagaaacg agagcagctc cgatctgtgg    900
gctagctctg gtggaacagc tggcgctcct acaccagccg ctcctaccga agagaataga    960
agcagcggcg acacccctgt gacaagcgcc tctgtgaaaa ccctggtcat gagcacccca   1020
gtgaagtccc cagtgatggg cgccagaacc tccaacattc ccctgaagtc tcccgctcct   1080
aacacactgg ccaactctcc agtggctggc cctcctaagt ctagcacccc tctgaaaagc   1140
cccgtgacct ctgtgtctgc ccctaacgct cctgtgaaac tggccgtgac caacgtgccc   1200
atgctgacca cacctgtgaa atccccactg agcaatgccc ctgccgaggc cggaagctct   1260
tgtatcattc ccgaggctca ggatagcgag gctggccaaa aaggcgaagc tgcaggcgct   1320
tctgctctgg gccctagctc tagctctttt agcaccggca ccagcgtggt gtctggcaca   1380
ccaggacctc tgagaagcgc cagacctacc tctagagccc tgcctcagtt tagcgtgtcc   1440
cctagtgtgc ctggcagaag ccctacactg tctagtacag ccggcgctac acacaccagc   1500
ggactggaaa cagaccaaga acagcatggc agcagcaccc tgccttctct ggctgccctt   1560
gattctagca gcgaactgcc aggcggcgac cccaatagac ctatcgctag acctagcctg   1620
acacagctgg cccaagagag caatgagggc ccttctgagc ctgctcagac cgaacaggtg   1680
ccaatgccct acagccccga aaagagcggg tgcagcaact accctatcag ccatgccgct   1740
gctcccacac ctcctggtcc aagagaagct cctctgagcc ctcctgagct gcccgatcct   1800
ccaagagata gcaccagacc tcagtactcc cagtacgtgt ccgccgtgga agatgccctg   1860
gatgtgctgg aatgtggcag actggccgcc atcttctacg aagtgtgggg ccctagaagg   1920
cagctgacca actttctgca ctggctgacc gacagaaacg gcagcctgac atgtaccgcc   1980
agactgagag atcaggaccg ggccacactg tgccctctgt atcctctgat cgaggtggtg   2040
gacgtgaact gcttcaacag cttcaaccgg tgcatctaca gtacaccaa ggacgaggct   2100 ttccctatgc acagcgacga acaccaccat gatgacagcc tgcctcatcc tcagcaggcc   2160
accgacgata gcagcaacca gagcgacagc aacagcaacg agggcagaca tctgctgctg   2220
gtgtctggtc ctggcgacgg acctcctctg tgttctcaaa atcttggcgc ccctggcggc   2280
ggaccaaaca atggacctca ggaccccgac aacaccgacg acaatggccc tcaagatcct   2340
gataataccg atgacaacgg cccacacgac cctctgcctc aagacccaga taacacagac   2400
gataacggtc cacaagatcc ggacaatact gacgataatg accccacga tccactgcct   2460 cacaacccta gcgatagcgc cggaaatgat ggcggacctc cacagctgac cgaggaagtg   2520
gaaaacaaag gcggagatca gggccctcct ctgatgaccg atggcggagg tggacactct   2580
cacgattctg gccacgacgg catcgaccct catctgccta cactgctgct cggcacatct   2640
ggctctggcg gcgacgatga tgatcctcat ggacctgtgc agctgagcta ctacgac     2697

<210> SEQ ID NO 24
<211> LENGTH: 899
<212> TYPE: PRT
<213> ORGANISM: Artificial sequence
<220> FEATURE:
```

```
<223> OTHER INFORMATION: Fusion of LMP1 of Epstein Barr virus and IPS1
      of Homo sapiens

<400> SEQUENCE: 24

Met Asp Leu Asp Leu Glu Arg Gly Pro Pro Gly Pro Arg Arg Pro Pro
1               5                   10                  15

Arg Gly Pro Pro Leu Ser Ser Ser Ile Gly Leu Ala Leu Leu Leu Leu
            20                  25                  30

Leu Leu Ala Leu Leu Phe Trp Leu Tyr Ile Ile Met Ser Asn Trp Thr
        35                  40                  45

Gly Gly Ala Leu Leu Val Leu Tyr Ala Phe Ala Leu Met Leu Val Ile
    50                  55                  60

Ile Ile Leu Ile Ile Phe Ile Phe Arg Arg Asp Leu Leu Cys Pro Leu
65                  70                  75                  80

Gly Ala Leu Cys Leu Leu Leu Leu Met Ile Thr Leu Leu Leu Ile Ala
                85                  90                  95

Leu Trp Asn Leu His Gly Gln Ala Leu Tyr Leu Gly Ile Val Leu Phe
            100                 105                 110

Ile Phe Gly Cys Leu Leu Val Leu Gly Leu Trp Ile Tyr Leu Leu Glu
        115                 120                 125

Ile Leu Trp Arg Leu Gly Ala Thr Ile Trp Gln Leu Leu Ala Phe Phe
    130                 135                 140

Leu Ala Phe Phe Leu Asp Ile Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg Pro Ser
            180                 185                 190

Pro Arg His Cys Pro Val Glu Arg Glu Gln Phe Lys Arg Asp Ala Gln
        195                 200                 205

Pro Arg Pro Gly Gly Asp Pro Asp Ala Pro Pro Gly Pro Asn Gly Glu
    210                 215                 220

Leu Leu Gln Ile Ser Pro Asn Glu Ala Val His Ile Gly Phe Thr Gly
225                 230                 235                 240

Glu Ser Lys Tyr Glu Asn Glu Glu Pro Gly His Cys Pro Gly Met Gly
                245                 250                 255

Leu Ser Thr Ser Ala Ser Ile Ala Leu Asp Glu Phe Cys Gly Ser Phe
            260                 265                 270

Pro Ser Asp Val Gln Ser Ala Leu Val Gly Pro Lys Ser Leu Glu Ser
        275                 280                 285

Gly Leu Gly Arg Asn Glu Ser Ser Ser Asp Leu Trp Ala Ser Ser Gly
    290                 295                 300

Gly Thr Ala Gly Ala Pro Thr Pro Ala Ala Pro Thr Glu Glu Asn Arg
305                 310                 315                 320

Ser Ser Gly Asp Thr Pro Val Thr Ser Ala Ser Val Lys Thr Leu Val
                325                 330                 335

Met Ser Thr Pro Val Lys Ser Pro Val Met Gly Ala Arg Thr Ser Asn
            340                 345                 350

Ile Pro Leu Lys Ser Pro Ala Pro Asn Thr Leu Ala Asn Ser Pro Val
        355                 360                 365

Ala Gly Pro Pro Lys Ser Ser Thr Pro Leu Lys Ser Pro Val Thr Ser
    370                 375                 380

Val Ser Ala Pro Asn Ala Pro Val Lys Leu Ala Val Thr Asn Val Pro
385                 390                 395                 400
```

-continued

```
Met Leu Thr Thr Pro Val Lys Ser Pro Leu Ser Asn Ala Pro Ala Glu
            405                 410                 415

Ala Gly Ser Ser Cys Ile Ile Pro Glu Ala Gln Asp Ser Glu Ala Gly
        420                 425                 430

Gln Lys Gly Glu Ala Ala Gly Ala Ser Ala Leu Gly Pro Ser Ser Ser
            435                 440                 445

Ser Phe Ser Thr Gly Thr Ser Val Val Ser Gly Thr Pro Gly Pro Leu
    450                 455                 460

Arg Ser Ala Arg Pro Thr Ser Arg Ala Leu Pro Gln Phe Ser Val Ser
465                 470                 475                 480

Pro Ser Val Pro Gly Arg Ser Pro Thr Leu Ser Ser Thr Ala Gly Ala
                485                 490                 495

Thr His Thr Ser Gly Leu Glu Thr Asp Gln Glu Gln His Gly Ser Ser
            500                 505                 510

Thr Leu Pro Ser Leu Ala Ala Leu Asp Ser Ser Ser Glu Leu Pro Gly
        515                 520                 525

Gly Asp Pro Asn Arg Pro Ile Ala Arg Pro Ser Leu Thr Gln Leu Ala
    530                 535                 540

Gln Glu Ser Asn Glu Gly Pro Ser Glu Pro Ala Gln Thr Glu Gln Val
545                 550                 555                 560

Pro Met Pro Tyr Ser Pro Glu Lys Glu Arg Cys Ser Asn Tyr Pro Ile
                565                 570                 575

Ser His Ala Ala Ala Pro Thr Pro Gly Pro Arg Glu Ala Pro Leu
            580                 585                 590

Ser Pro Pro Glu Leu Pro Asp Pro Arg Asp Ser Thr Arg Pro Gln
        595                 600                 605

Tyr Ser Gln Tyr Val Ser Ala Val Glu Asp Ala Leu Asp Val Leu Glu
    610                 615                 620

Cys Gly Arg Leu Ala Ala Ile Phe Tyr Glu Val Trp Gly Pro Arg Arg
625                 630                 635                 640

Gln Leu Thr Asn Phe Leu His Trp Leu Thr Asp Arg Asn Gly Ser Leu
                645                 650                 655

Thr Cys Thr Ala Arg Leu Arg Asp Gln Asp Arg Ala Thr Leu Cys Pro
            660                 665                 670

Leu Tyr Pro Leu Ile Glu Val Val Asp Val Asn Cys Phe Asn Ser Phe
        675                 680                 685

Asn Arg Cys Ile Tyr Lys Tyr Thr Lys Asp Glu Ala Phe Pro Met His
    690                 695                 700

Ser Asp Glu His His His Asp Asp Ser Leu Pro His Pro Gln Gln Ala
705                 710                 715                 720

Thr Asp Asp Ser Ser Asn Gln Ser Asp Ser Asn Ser Asn Glu Gly Arg
                725                 730                 735

His Leu Leu Leu Val Ser Gly Ala Gly Asp Gly Pro Pro Leu Cys Ser
            740                 745                 750

Gln Asn Leu Gly Ala Pro Gly Gly Pro Asn Asn Gly Pro Gln Asp
        755                 760                 765

Pro Asp Asn Thr Asp Asp Asn Gly Pro Gln Asp Pro Asp Asn Thr Asp
    770                 775                 780

Asp Asn Gly Pro His Asp Pro Leu Pro Gln Asp Pro Asp Asn Thr Asp
785                 790                 795                 800

Asp Asn Gly Pro Gln Asp Pro Asp Asn Thr Asp Asp Asn Gly Pro His
                805                 810                 815
```

-continued

```
Asp Pro Leu Pro His Asn Pro Ser Asp Ser Ala Gly Asn Asp Gly Gly
            820             825             830

Pro Pro Gln Leu Thr Glu Glu Val Glu Asn Lys Gly Gly Asp Gln Gly
        835             840             845

Pro Pro Leu Met Thr Asp Gly Gly Gly His Ser His Asp Ser Gly
        850             855             860

His Asp Gly Ile Asp Pro His Leu Pro Thr Leu Leu Leu Gly Thr Ser
865             870             875             880

Gly Ser Gly Gly Asp Asp Asp Pro His Gly Pro Val Gln Leu Ser
                885             890             895

Tyr Tyr Asp
```

VIRAL VECTOR CONSTRUCTS FOR EXPRESSION OF GENETIC ADJUVANTS ACTIVATING THE CD40 AND STING PATHWAYS

BACKGROUND

Canonical vaccine strategies based on the induction of antibody-based immune response have resulted in the eradication or near eradication of a number of previously fatal infectious diseases, such as smallpox, poliomyelitis and tetanus. Yet, these classical human vaccines have either been ineffective or unsafe for use in other infectious diseases, such as HIV and hepatitis, and for non-infectious illnesses such as cancer.

A new generation of immunotherapeutic products, aimed at inducing cellular immune responses, may overcome the limitations of traditional vaccines by recognizing and killing cancer cells and infected cells instead of the pathogen itself. Nucleic acid vaccines, and particularly viral vectors, have shown great potential to translate to the clinics.

Cancer cells and many infectious agents have ways of eluding the immune system, which makes creating effective vaccines difficult. Classical vaccines often require an adjuvant, e.g., aluminum salts, for optimal effectiveness, but conventional adjuvants are typically poor enhancers of cellular immune responses. Some strategies have been proposed to improve the quality and magnitude of the cellular immune response elicited by viral vectors. A new class of genetic adjuvants has been developed to improve cellular immune responses induced by vector-based immunotherapy. Genetic adjuvants consist of DNA sequences that encode immune regulatory molecules.

The cluster of differentiation 40 (CD40) is a membrane protein present on a variety of cells, most notably antigen-presenting cells such as dendritic cells (DC). CD40 is essential for the initiation and progression of cellular and humoral adaptive immunity, being involved in DC maturation, cytokine production, antibody isotype switching, memory B cell development, and germinal center formation, among other processes. The activation of CD40 requires that it become clustered in the membrane so that its cytoplasmic signaling domain forms a supramolecular signaling complex that subsequently activates different pro-inflammatory signaling pathways. The clustering of CD40 is initiated by either a multimeric form of its ligand (CD40 ligand or CD40L) or by anti-CD40 antibodies that must be arrayed on a nearby cell via binding to Fc receptors. In its mRNA form, CD40 ligand has been used as an adjuvant in vaccines eliciting a cellular immune response (e.g., Argos Therapeutics AGS003, TriMix).

Stone et al. (WO 2013/0039942) discloses the use of a genetic adjuvant that induces a cellular immune response mimicking that of an activated CD40 receptor. In this approach a nucleic acid vaccine encodes latent membrane protein 1 (LMP1) of the Epstein Barr virus. Results have demonstrated that full length LMP1, when expressed in various forms (e.g., plasmids, mRNA, viruses, and vectors) spontaneously forms clusters, mimicking activated CD40L and its adjuvant effects. For example:

(i) macrophages infected by LMP1 expressing HIV-1 in vitro are stimulated to make immunostimulatory cytokines including IL-8, MIP-1beta, IL1-beta, IL-6, IL-12p70 and TNFalpha (without any production of IL-10, an immunosuppressive cytokine);

(ii) human dendritic cells are stimulated in vitro by infection with LMP1 expressing HIV-1 to produce stimulatory cytokines including IL-8, IL-1beta, TNF-alpha, IL-6, and IL-12p70;

(iii) human dendritic cells are stimulated by a single cycle SIV (scSIV) expressing LMP1 to produce stimulating cytokines including IL-8, IL1-beta, IL-6, IL-12p70 and TNFalpha;

(iv) in addition to being immunostimulatory, HIV-1-LMP1 and scSIV-LMP1 are also self-adjuvanting in vitro by enhancing the antigen presentation function of dendritic cells to induce the proliferation of HIV and SIV antigen-specific T-cells;

(v) HIV-LMP1 stimulates DCs and macrophages in vitro to upregulate immunologically important cell surface costimulatory molecules like CD40, CD80, and CD83, and migration signals like CCR-7; and (vi) mice intramuscularly injected three times every two weeks with a mix of plasmids encoding LMP1 and a melanoma specific antigen (gp100) are protected from tumor growth.

Stone et al. (WO 2014/039961) discloses the use of a genetic adjuvant that induces the secretion of interferon alpha and beta and thus induces the expression of interferon stimulated genes. In this approach, a nucleic acid vaccine encodes, optionally in addition to a transgene encoding a marker protein or antigen, a fusion protein including the transmembrane portion of the LMP1 protein in which the intra-cytoplasmic domain has been replaced by an immune effector or adaptor protein, such as the IPS1 protein. Activation of IFN-β promoter stimulator (IPS1, also referred to as MAVS, VISA, or Cardif) generates potent T cell responses via the STING (stimulator of interferon genes) pathway. When expressed in cells, the transmembrane domains of LMP1 spontaneously form clusters that allow the aggregation of the IPS1 into intracytoplasmic clusters, activating the STING pathway. The transmembrane domain of LMP1 fused with the full length murine IPS1 has been shown to induce the secretion of IFNalpha, IFNbeta, and IL-6, and also to induce the expression of maturation (CD40 and CCR7) and activation markers (CD80 and CD86) in mouse macrophages.

There is a need for self-adjuvanting vaccines that induce the intense cellular immune response required to break the immune tolerance observed in such indications as cancer, HIV, and other unmet medical needs.

SUMMARY

The present technology provides viral vectors encoding genetic adjuvants for improving immune responses, particularly cell-mediated immune responses, such as those directed against cancer or infections, and methods for using the viral vectors. The antigen and adjuvant constructs of the present technology enhance an immune response by an activation process that simultaneously mimics CD40 activation and activates the STING pathway. The construct sequences have been optimized for use in human subjects.

One aspect of the present technology is a viral vector including (i) one transgene encoding one or more marker proteins, antigens, epitopes, or combinations thereof, (ii) a full length latent membrane protein 1 (LMP1) of the Epstein Barr virus that has been codon optimized for human expression, and (iii) a transgene encoding a fusion protein including the transmembrane portion of the latent membrane protein 1 (LMP1) of Epstein Barr virus in which the intra-cytoplasmic domain has been replaced by human IPS1 or a variant thereof capable of activating the STING pathway. Optionally, the vector further includes (iv) a nucleic acid sequence encoding one or more soluble and secreted immune checkpoint inhibitor molecules or one or more soluble immune modulator molecules. In preferred embodiments, the viral vector is a lentiviral vector. In some embodiments, the vector includes a functional lentiviral integrase protein and can thereby integrate into the genome of the cells it is transducing.

Another aspect of the present technology is a viral vector including (i) one transgene encoding one or more marker proteins, antigens, epitopes, or combinations thereof, (ii) a fusion protein including the transmembrane domain of the latent membrane protein 1 (LMP1) of Epstein Barr virus fused to an intra-cytoplasmic domain which is either (a) a wild type LMP 1 intra-cytoplasmic domain in fusion with human IPS1 or a variant thereof (e.g., hIPS1 delta TM, or hIPS1 delta TM delta PR or hIPS1 reverse, or hIPS1 reverse delta TM) capable of activating the STING pathway or (b) a human IPS1 or a variant thereof (e.g., hIPS1 delta TM, or hIPS1 delta TM delta PR or hIPS1 reverse, or hIPS1 reverse delta TM) capable of activating the STING pathway in fusion with a wild type LMP1 intracytoplasmic domain. Optionally, the vector further includes (iii) a nucleic acid sequence encoding one or more soluble and secreted immune checkpoint inhibitor molecules or soluble immune modulator molecules. In preferred embodiments, the viral vector is a lentiviral vector. In some embodiments, the vector includes a functional lentiviral integrase protein and can thereby integrate into the genome of the cells it is transducing.

The antigen may be a tumor antigen, viral antigen, or microbial antigen. Multiple antigens or selected epitopes of one or more antigens can be encoded by the vector. In certain embodiments, at least one antigen is selected from the group consisting of NY-ESO-1, mesothelin, PSA, MART-1, MART-2, Gp100, tyrosinase, p53, ras, MUC1, SAP-1, survivin, CEA, Ep-CAM, Her2, BRCA1/2, gag, reverse transcriptase, tat, circumsporozoite protein, HCV nonstructural proteins, hemaglutinins, and combinations thereof. In certain embodiments, the vector further encodes at least one immune checkpoint inhibitor molecule or soluble immune modulator molecules, such as an anti-CTLA-4 molecule, a PD1 blocker, a PDL1 blocker, or a combination thereof.

In certain embodiments, the viral vector includes more than one nucleic acid sequence. In some of these embodiments, the first nucleic acid sequence encodes one or more marker proteins, antigens, epitopes, or combinations thereof; the second nucleic acid sequence encodes a full length latent membrane protein 1 (LMP1) of the Epstein Barr virus that has been codon optimized for human expression, the third nucleic acid sequence encodes a fusion protein including the transmembrane portion of the latent membrane protein 1 (LMP1) of Epstein Barr virus in which the intra-cytoplasmic domain has been replaced by human IPS1 or a variant thereof capable of activating the STING pathway; and optionally a fourth nucleic acid sequence encodes one or more immune checkpoint inhibitor molecules ("anti-checkpoints") or soluble immune modulator molecules. Preferably, the first and second, as well as the second and third and third and fourth, nucleic acid sequences are separated by a nucleic acid sequence encoding an internal ribosome entry site (IRES). The first and second, as well as the second and third nucleic acid sequences can be separated by a nucleic acid sequence encoding a self-cleaving peptide (for example, 2A peptide). The first and second, as well as the second and third nucleic acid sequences can be separated by a nucleic acid sequence encoding either a self-cleaving peptide (for example, 2A peptide) or an internal ribosome entry site (IRES).

In yet other embodiments, the viral vector includes more than one nucleic acid sequence. In some of these embodiments, the first nucleic acid sequence encodes one or more marker proteins, antigens, epitopes, or combinations thereof; the second nucleic acid sequence encodes a full length latent membrane protein 1 (LMP1) of the Epstein Barr virus in fusion with the intra-cytoplasmic domain of the human IPS1 or a variant thereof capable of activating the STING pathway (the resulting fusion protein has been codon optimized for human expression), the third nucleic acid sequence encodes a full length latent membrane protein 1 (LMP1) of the Epstein Barr virus that has been codon optimized for human expression; and optionally a fourth nucleic acid sequence encodes one or more immune checkpoint inhibitor molecules ("anti-checkpoints") or soluble immune modulator molecules. Preferably, the first and second, as well as the second and third nucleic acid sequences are separated by a nucleic acid sequence encoding an internal ribosome entry site (IRES). The first and second, as well as the second and third nucleic acid sequences can be separated by a nucleic acid sequence encoding a self-cleaving peptide (for example, 2A peptide). The first and second, as well as the second and third nucleic acid sequences can be separated by a nucleic acid sequence encoding either a self-cleaving peptide (for example, 2A peptide) or an internal ribosome entry site (IRES).

Another aspect of the present technology is an immunotherapeutic formulation for preventing or treating a disease or condition in a subject including the viral vector. In preferred embodiments, the disease or condition is cancer or infection.

Another aspect of the technology is method for inducing an immune response against cancer or infection in a subject, the method including administering the viral vector or the immunotherapeutic formulation to a subject in need thereof. In some embodiments, administering the viral vector to the subject vaccinates the subject against cancer or infection.

In some embodiments, the cancer is selected from the group consisting of: melanoma, glioma, prostate cancer, breast cancer, cervical cancer, colorectal cancer, kidney cancer, lung cancer, lymphoma, ovarian cancer, sarcomas, and pancreatic cancer. In some embodiments, the cancer harbors a tumor antigen listed above. In some embodiments, the cancer is sensitive to an anticheckpoint. In some embodiments, the infectious disease is selected from the group consisting of: HIV/AIDS, hepatitis C, HPV, pneumonia, influenza, malaria, leishmaniasis, tuberculosis, Hansen's disease, rabies, dengue, Zika virus infection, Ebola virus infection, and schistosomiasis. In some embodiments, the infectious agent harbors a viral or microbial antigen listed above. In some embodiments, the infectious disease is sensitive to an anticheckpoint.

The present technology also can be summarized with the following listing of embodiments.

1. A viral vector comprising a first nucleic acid sequence encoding an antigen or an antigenic epitope, a second nucleic acid encoding a full length latent membrane protein 1 (LMP1) of Epstein Barr virus, and a third nucleic acid sequence encoding a fusion protein including the transmembrane portion of LMP1 in which the intra-cytoplasmic domain has been replaced by human IPS1 or a variant thereof capable of activating the STING pathway, wherein the encoded sequences of the vector being codon are optimized for human expression, and wherein the second and third nucleic acid sequences follow the first nucleic acid sequence in any order.

2. A viral vector comprising a first nucleic acid sequence encoding an antigen or an antigenic epitope, a second nucleic acid sequence encoding a full length latent membrane protein 1 (LMP1) of the Epstein Barr virus in fusion with the intra-cytoplasmic domain of the human IPS1 or a variant thereof capable of activating the STING pathway (the resulting fusion protein has been codon optimized for human expression), or the second nucleic acid sequence encoding a fusion protein including the transmembrane portion of the latent membrane protein 1 (LMP1) of Epstein Barr virus in which the intra-cytoplasmic domain has been replaced by human IPS1, or a variant thereof capable of activating the STING pathway, in fusion with the intracytoplasmic domain of LMP1 (the resulting fusion protein has been codon optimized for human expression);

3. The viral vector of embodiment 1 or embodiment 2, wherein the vector is a lentiviral vector.

4. The viral vector of any of the preceding embodiments, wherein the first nucleic acid sequence encodes a fusion protein comprising two or more antigens or two or more antigenic epitopes.

5. The viral vector of any of the preceding embodiments, wherein the second nucleic acid sequence of embodiment 1 or 2, or the third nucleic acid sequence of embodiment 1, comprises a sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21 and SEQ ID NO:23.

6. The viral vector of any of the preceding embodiments, wherein the vector further comprises a nucleic acid sequence encoding a soluble and secreted immune checkpoint inhibitor molecule or a soluble immune modulator molecule.

7. The viral vector of embodiment 6, wherein the soluble immune checkpoint inhibitor molecule or a soluble immune modulator molecule is selected from the group consisting of CTLA-4, PD-1, PDL-1, LAG-3, TIM 3, B7-H3, ICOS, IDO, 4-1BB, CD47, B7-H4, OX-40, TIGIT, CD160, and combinations thereof.

8. The viral vector of any of the preceding embodiments, wherein the vector further comprises a functional lentiviral integrase protein, wherein the vector is self-inactivating.

9. The viral vector of any of the preceding embodiments, wherein the antigen is selected from the group consisting of NY-ESO-1, mesothelin, PSA, MART-1, MART-2, Gp100, tyrosinase, p53, ras, MUC1, SAP-1, survivin, CEA, Ep-CAM, Her2, BRCA1/2, gag, reverse transcriptase, tat, circumsporozoite protein, HCV nonstructural proteins, hemaglutinins, and combinations thereof.

10. An immunotherapeutic formulation for preventing or treating cancer or infection in a subject, the formulation comprising the viral vector of any of embodiments 1-9.

11. A method of inducing or enhancing an immune response against a cancer or an infectious disease in a subject, the method comprising administering the viral vector of any of embodiments 1-9 or the immunotherapeutic formulation of embodiment 10 to a subject in need thereof, whereby an immune response against said cancer or infectious disease is induced or enhanced in the subject.

12. The method of embodiment 11, whereby an immune response is induced or enhanced against a cancer, and the cancer is selected from the group consisting of: melanoma, glioma, prostate cancer, breast cancer, cervical cancer, colorectal cancer, kidney cancer, lung cancer, lymphoma and pancreatic cancer.

13. The method of embodiment 11, whereby an immune response is induced or enhanced against an infectious disease, and the infectious disease is selected from the group consisting of: HIV/AIDS, hepatitis C, HPV, pneumonia, influenza, malaria, leishmaniosis, tuberculosis, Hansen's disease, rabies, dengue, Zika, Ebola, and schistosomiasis.

BRIEF DESCRIPTION OF THE DRAWINGS

FIG. 6 shows a schematic representation of the secondary structure of an LPM1-IPS1 fusion protein with IPS1 transmembrane domain removed.

FIG. 7 shows the structure of LPM1-reversed IPS1 fusion protein, with IPS transmembrane domain removed, and the caspase recruitment domain (CARD) and proline-rich (PRO) domain in an inverted orientation.

FIG. 8A shows a construct containing (a) a promoter (human ubiquitin, Ubi); (b) a reporter gene (e.g., green fluorescent protein) or, alternatively, one or more antigen genes; (c) a gene for full-length LMP1; (d) a gene for the fusion protein LMP1-IPS1 (the fusion protein may contain human IPS1 or a functional variant thereof having a STING enhancing activity) and (e) a gene encoding a soluble and secreted immune checkpoint inhibitor or a soluble and secreted immune modulator molecule. FIG. 8B shows a construct containing (a) a promoter (human ubiquitin, Ubi); (b) a reporter gene (e.g., green fluorescent protein) or, alternatively, one or more antigen genes; (c) a gene for full-length LMP1; (d) a gene for the fusion protein LMP1-IPS1 (the fusion protein may contain human IPS1 or a functional variant thereof having a STING enhancing activity); and (e) a gene encoding a soluble and secreted immune checkpoint inhibitor or a soluble and secreted immune modulator molecule.

In FIG. 9A, the adjuvant is a fusion of LMP1 (deltaTM) with the cytoplasmic signaling domain of LMP1 which is in turn fused to hIPS1 cytoplasmic signaling domain (STING activator) or a functional equivalent thereof. FIG. 9B shows a fusion similar to that of FIG. 9A, but with the two cytoplasmic signaling domains presented in opposite order.

FIG. 11A shows GFP transgene expression in human dendritic cells 96 h post-transduction with the lentiviral constructs. FIG. 11B shows GFP transgene expression in human macrophages 96 h post-transduction with the lentiviral constructs.

FIG. 12A shows the panel of upregulated cytokines in human dendritic cells 96 h post-transduction with the lentiviral constructs. FIG. 12B shows the panel of upregulated markers in human GFP-positive dendritic cells 96 h post-transduction with the lentiviral constructs (expression normalized to GFP). FIG. 12C shows the panel of upregulated cytokines in human macrophages 96 h post-transduction with the lentiviral constructs. FIG. 12D shows the panel of upregulated markers in GFP-positive human macrophages 96 h post-transduction with the lentiviral constructs (expression normalized to GFP). (expression normalized to GFP).

DETAILED DESCRIPTION

Figure 1:
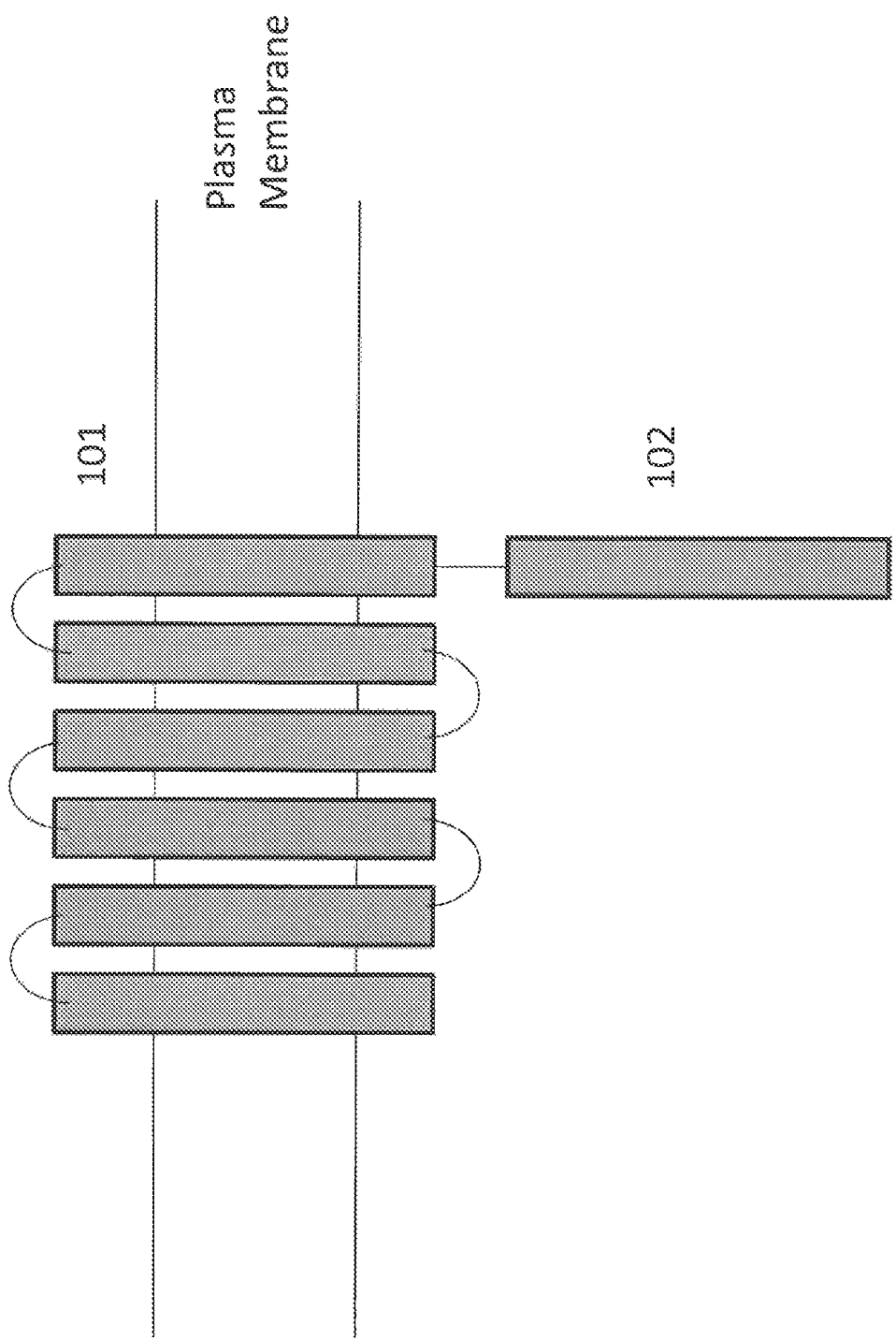
FIG. 1 shows a schematic representation of the secondary structure of full-length LMP1 protein.
Figure 2:
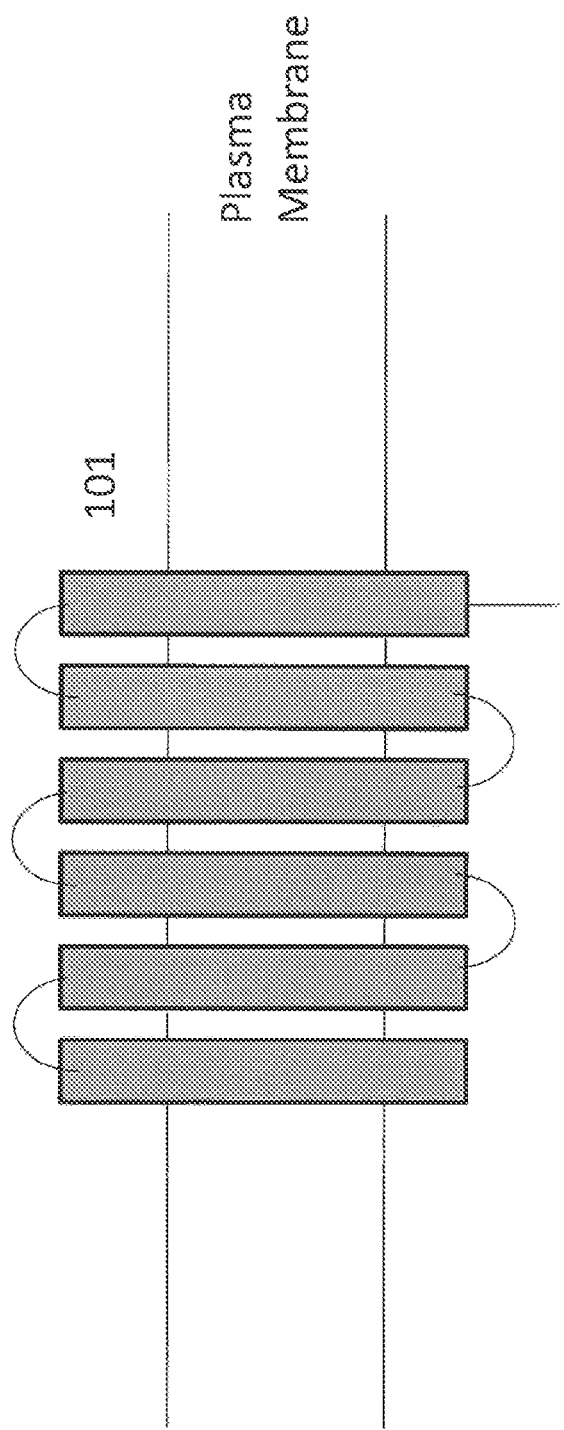
FIG. 2 shows a schematic representation of the secondary structure of a truncated LMP1 protein, with the intracytoplasmic signaling domain removed.
Figure 3A:
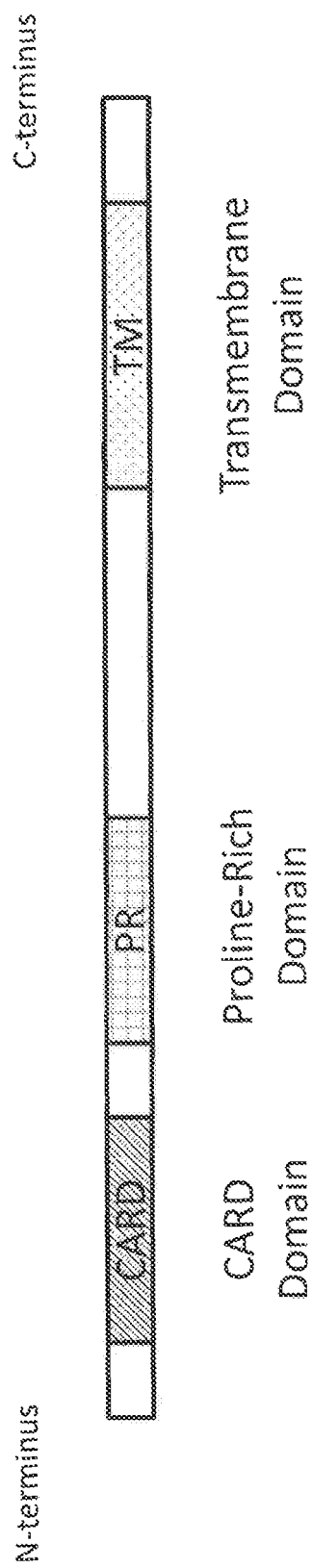
FIG. 3A shows a schematic representation of the IPS1 protein.
Figure 3B:
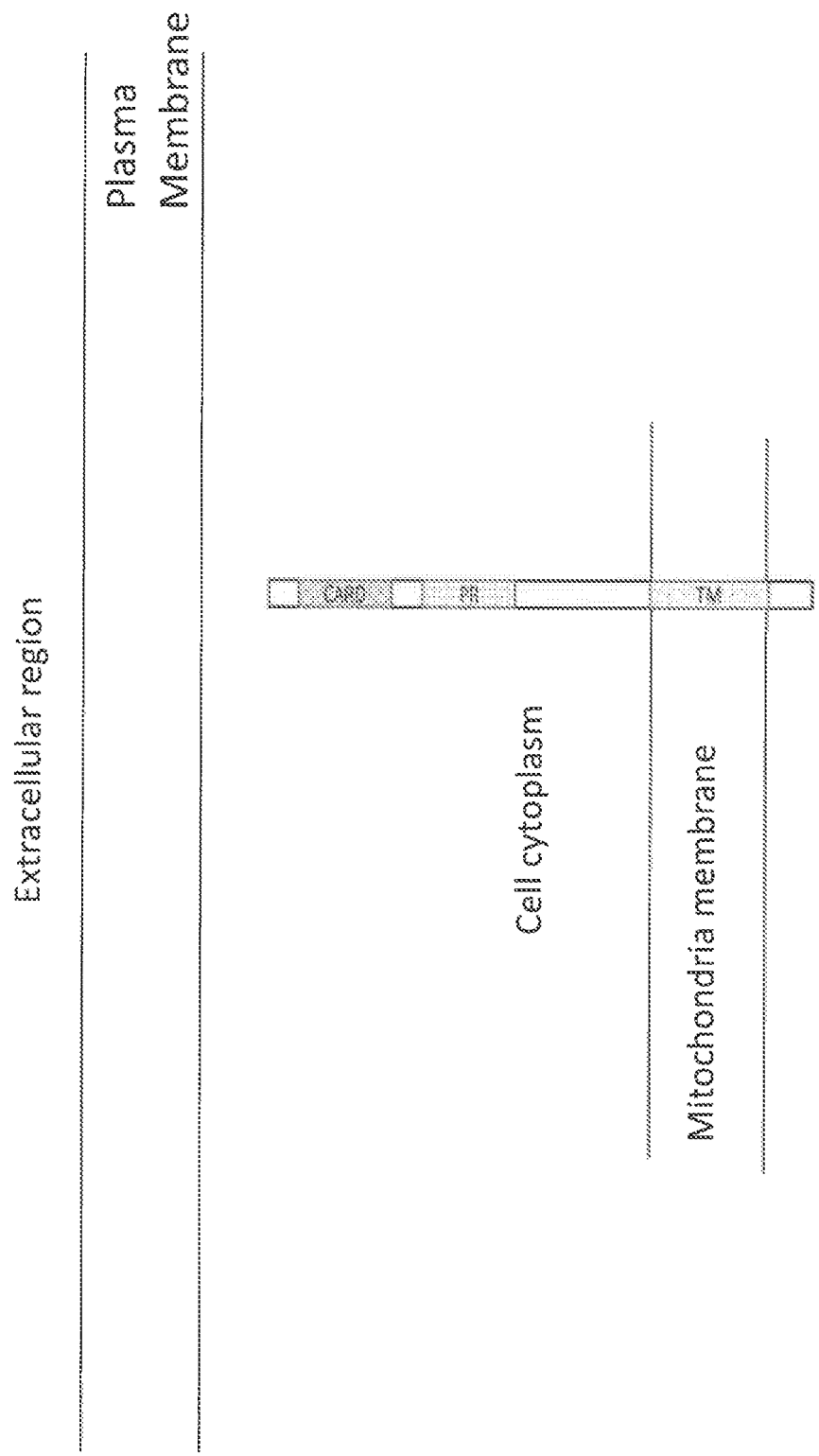
FIG. 3B shows its orientation in the mitochondrial membrane.
Figure 4:
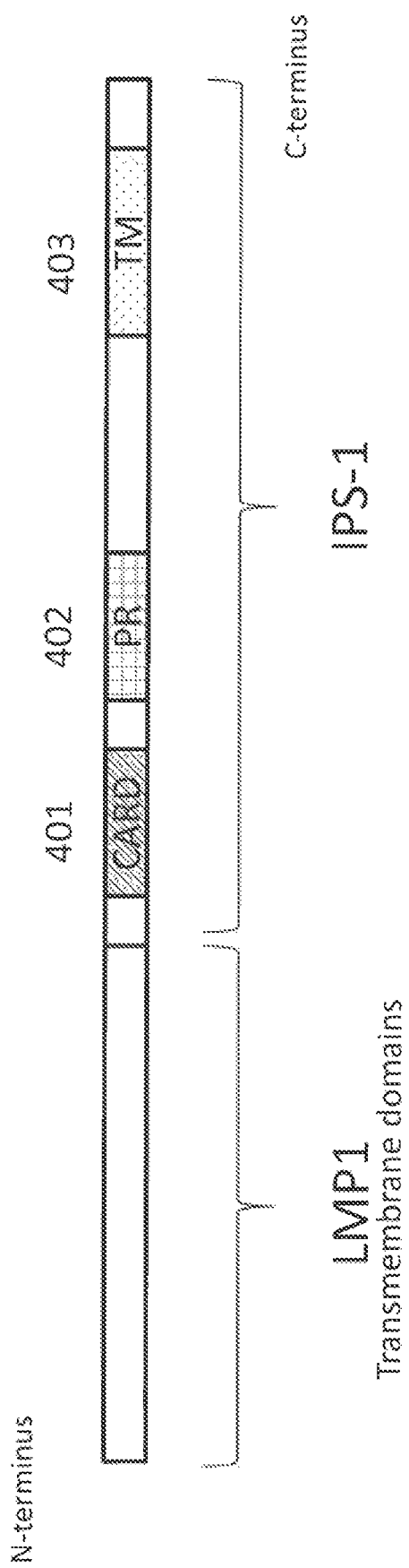
FIG. 4 shows a schematic representation of an LPM1-IPS1 fusion protein.
Figure 5:
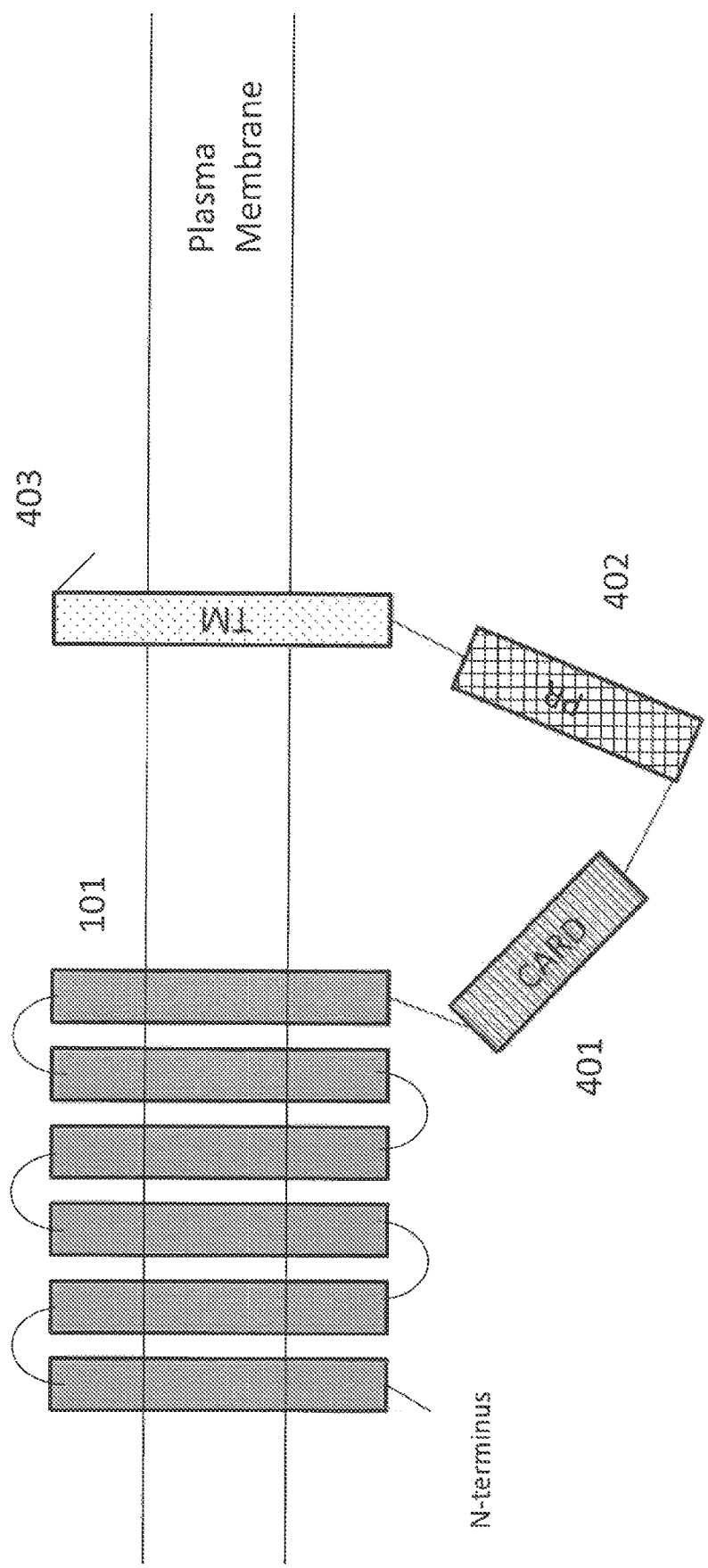
FIG. 5 shows a schematic representation of the secondary structure of an LPM1-IPS1 fusion protein as it should be produced when expressed in the order described in WO 2014/039961.

The present technology provides viral vector constructs for the expression of genetic adjuvants for use in immunotherapeutic products and methods of using the vectors. The vector constructs can improve the quality and intensity of an immune response, such as those directed against cancer or infections, being especially suited to induce and/or enhance cell-mediated immune responses. The vector constructs of the present technology are particularly effective at enhancing immune responses because the constructs lead to both an activation of specific cell-mediated immune responses mediated by activation of a CD40-like pathway, promoted by expression and activation of the intracytoplasmic signaling domain of LMP1 from EBV, and activation of innate immune responses through activation of the STING pathway, promoted by expression and activation of an LMP1-IPS1 fusion protein. Activation of either the CD-40-like pathway or the STING pathway can be mediated by clustering of LMP1 transmembrane domains which activates the intra-cytoplasmic signaling domains.

The present technology describes the use of a single vector construct encompassing an antigenic cassette and a genetic adjuvant. When compared to concomitant injections of two vectors (one coding for the antigen and one coding for the adjuvant), the use of a single product will simplify the development (including industrial, regulatory and clinical aspects) and enhance the efficacy and safety of the treatment. With this unique construct, the cells expressing the antigenic cassette will constitutively benefit from the expression of the adjuvant improving the intensity and the quality of the triggered immune response. The transduced cells will be rapidly eliminated by the immune response, which reduces the risk of any long term and undesired expression of the genetic sequences that could be a serious consideration for regulatory agencies. In addition, the production and injection of only one vector will be more cost efficient when compared to the injection of two distinct vectors.

Viral vector constructs of the present technology are organized according one of two different strategies. In the first strategy, the vector contains two separate adjuvant expression cassettes, one that encodes full length LMP1 protein and the other that encodes a fusion protein containing the LMP1 whose intra-cytoplasmic domain has been replaced with human IPS1 or a variant thereof that activates the STING pathway. Under this strategy, the vector contains one or more nucleic acid sequences that encode: (i) a full length EBV LMP 1 protein that has been codon optimized for human expression, (ii) an EBV LMP1 protein in which the intra-cytoplasmic domain has been replaced by human IPS1 or a variant thereof capable of activating the STING pathway, and (iii) one or more antigens.

In the second strategy, the vector contains a single adjuvant expression cassette that encodes either (i) a full length LMP1 in fusion with the intra-cytoplasmic domain of the human IPS1 or a variant thereof capable of activating the STING pathway, or (ii) a fusion protein including the transmembrane portion of LMP1 in which the intra-cytoplasmic domain has been replaced by human IPS1, or a variant thereof capable of activating the STING pathway, in fusion with the intracytoplasmic domain of LMP 1. In addition, the vector encodes one or more antigens.

In a typical embodiment, the technology provides activation of immune responses by an aggregation of two or more full-length LMP1 proteins in the cell membrane as well as aggregation of two or more truncated LMP1 proteins (lacking their original intra-cytoplasmic signaling domains) in the cell membrane, and/or aggregation of two or more IPS1 intra-cytoplasmic signaling domains fused to the truncated LMP1 proteins.

After direct injection, introduction of the nucleic acid sequences and consequent protein expression can occur in any type of cell, but preferably occur in skeletal muscle cells or immune cells. This technology can be used for traditional prophylactic or therapeutic vaccines against cancer and infectious diseases, as well as cell-based therapies such as dendritic cell therapy. In the experiments described herein, the viral vectors are expected to markedly enhance immune responses and protection from or treatment of infection and cancer.

"Vector" refers to a molecule containing a nucleic acid sequence coding for at least part of a gene product capable of being transcribed. In some cases, nucleic acid molecules are then translated into a protein, polypeptide, or peptide. In other cases, these sequences are not translated, such as in the production of antisense molecules, ribozymes or aptamers. Vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

A "construct" can be any type of engineered nucleic acid coding for gene products in which part or all of the nucleic acid encoding sequence is capable of being transcribed. The transcript generally is translated into a protein, but it need not be. In certain embodiments, expression includes both transcription of a gene and translation of mRNA into a gene product. In other embodiments, expression only includes transcription of the nucleic acid encoding genes of interest.

As used herein, "vaccine" includes all prophylactic and therapeutic vaccines. An "adjuvant" can be any molecule or composition that activates or enhances an immune response to an antigen. An adjuvant may enhance the efficacy of a vaccine by helping to modify the immune response to particular types of immune system cells. An adjuvant may be an immunostimulant that triggers activation of antigen-presenting cells such as dendritic cells, macrophages, and B cells. Adjuvants are also understood to provide a "danger" signal indicating that the immune system should go into a state of alert. Adjuvants may act by facilitating antigen presentation by antigen-presenting cells, by activating macrophages and lymphocytes and/or by supporting the production of cytokines. Without an adjuvant, immune responses may either fail to progress or may be diverted into ineffective immunity or tolerance. Adjuvants are often needed for effective preventative or therapeutic vaccines, or for inducing an anti-tumor immune response. A "genetic adjuvant" is an adjuvant that is provided in the form of a nucleic acid, which is expressed by target cells to produce a molecule that functions as an adjuvant.

An antigen-presenting cell (APC) is any of a variety of cells capable of displaying, acquiring, or presenting at least one antigen or antigenic fragment on (or at) its cell surface. In general, the term "antigen-presenting cell" can refer to any cell that accomplishes the goal of the technology by aiding the enhancement of an immune response (i.e., from the T-cell or B-cell arms of the immune system) against an antigen or antigenic composition. Such cells can be defined by those of skill in the art, using methods disclosed herein and in the art. As is understood by one of ordinary skill in the art, and used herein certain embodiments, a cell that displays or presents an antigen normally or preferentially with a class II major histocompatibility molecule or complex to an immune cell is an "antigen presenting cell." In certain aspects, a cell (e.g., an APC) may be fused with another cell, such as a recombinant cell or a tumor cell that expresses the desired antigen. Methods for preparing a fission of two or more cells are well known in the art. In some cases, the immune cell to which an antigen-presenting cell displays or presents an antigen is a CD4+ T or a CD8+ T cell. Additional molecules expressed on the APC or other immune cells may aid or improve the enhancement of an immune response. Secreted or soluble molecules, such as for example, cytokines and adjuvants, may also aid or enhance the immune response against an antigen. A dendritic cell (DC) is an antigen-presenting cell existing in vivo, in vitro, ex vivo, or in a host or subject, or which can be derived from a hematopoietic stem cell or a monocyte. Dendritic cells and their precursors can be isolated from a variety of lymphoid organs, e.g., spleen, lymph nodes, as well as from bone marrow and peripheral blood. The DC has a characteristic morphology with thin sheets (*Lamellipodia*) extending in multiple directions away from the dendritic cell body. Typically, dendritic cells express high levels of major histocompatibility complex (MHC) and costimulatory (e.g., B7-1 and B7-2) molecules. Dendritic cells can induce antigen specific differentiation of T cells in vitro, and are able to initiate primary T cell responses in vitro and in vivo.

By the phrase "immune response" is meant induction of antibody and/or immune cell-mediated responses specific against an antigen or antigens or allergen(s) or drug or biologic. The induction of an immune response depends on many factors, including the immunogenic constitution of the challenged organism, the chemical composition and configuration of the antigen or allergen or drug or biologic, and the manner and period of administration of the antigen or allergen or drug or biologic. An immune response has many facets, some of which are exhibited by the cells of the immune system (e.g., B-lymphocytes, T-lymphocytes, macrophages, and plasma cells). Immune system cells may participate in the immune response through interaction with an antigen or allergen or other cells of the immune system, the release of cytokines and reactivity to those cytokines. Immune responses are generally divided into two main categories—humoral and cell-mediated. The humoral component of the immune response includes production of antibodies specific for an antigen or allergen or drug or biologic. The cell-mediated component includes the generation of delayed-type hypersensitivity and cytotoxic effector cells against the antigen or allergen.

Activation or stimulation of the immune system may be mediated by the activation of immune effector cells, such as lymphocytes, macrophages, dendritic cells, natural killer cells (NK cells) and cytotoxic T lymphocytes (CTL). It can be mediated by activation and maturation of antigen presenting cells, such as dendritic cells. It can be mediated by the blockade of inhibitory pathways, such as by inhibiting immune checkpoint molecules.

By the term "LMP1 gene," is meant a native Epstein Barr virus LMP-encoding nucleic acid sequence, e.g., the native Epstein Barr virus LMP1 gene; a nucleic acid having sequences from which a LMP1 cDNA can be transcribed; and/or allelic variants and homologs of the foregoing. An exemplary nucleic acid sequence of LMP1 is GenBank Accession No. M58153.1. The term encompasses double-stranded DNA, single-stranded DNA, and RNA.

By the term "LMP1 protein," is meant an expression product of a LMP1 gene or a protein that shares at least 65% (but preferably 75, 80, 85, 90, 95, 96, 97, 98, or 99%) amino acid sequence identity with the foregoing and displays a functional activity of a native LMP1 protein. A "functional activity" of a protein is any activity associated with the physiological function of the protein. LMP1 consists of an N-terminal transmembrane region linked to a C-terminal cell signaling region that is analogous to the CD40 receptor on immune cells. In addition to anchoring LMP1 into the membrane, the N-terminus of LMP1 self-aggregates and leads to clustering of LMP1 or any protein linked to the LMP1 N-terminal domain. The transmembrane (aggregation) domain of LMP1 protein is amino acids 1-190 of the amino acid sequence set forth in GenBank Accession No. AAA66330.1.

Latent membrane protein-1 (LMP1) is a gene in the Epstein-Barr Virus (EBV). Its N-terminus is composed of 6 contiguous transmembrane domains that anchor the protein into the membrane. FIG. 1 shows the structure of LMP1 protein showing a transmembrane domain 101 and an intracytoplasmic signaling domain 102. LMP1 needs no ligand or antibody to initiate signaling through its cytoplasmic domain since its N-terminal transmembrane domain spontaneously forms clusters in the cell membrane and thereby clusters the intracytoplasmic domain(s) that are connected to it via peptide bonds as a single polypeptide chain. In this sense, LMP1 is said to be "constitutively activated." Likewise, fusion proteins that link the N-terminal transmembrane domain to signaling domain(s) that require clustering in order to function can also be said to be "constitutively activated" and no longer need the ligand from the receptor from which they are taken.

Interferon Promoter Stimulator-1 (IPS1, also called MAVS, VISA, or Cardif) is a transmembrane mitochondrial protein related to the STING pathway ("stimulator of interferon genes"; also known as TMEM173, MPYS, MITA and ERIS), which is important for the innate response to pathogen-derived nucleic acids in the cytosol. IPS1 contains a C-terminal transmembrane domain that anchors the protein to the outer membrane of mitochondria where it forms aggregates (i.e., multimers) once activated. IPS1 also is present in peroxisomes and mitochondrial-associated membranes. IPS1 also contains a caspase recruitment domain (CARD), indispensable for downstream protein-protein interactions, and three TRAF-interacting motifs (TIM), two included in the N-terminal proline-rich region and the third located in the C-terminal region. Membrane localization of IPS1 may be important for its activity, since removal of the transmembrane domain inhibits the IPS1-mediated antiviral response. IPS1 functions as an adaptor protein for pathogen recognition receptors, such as retinoic-acid-inducible gene-I (RIG-I)-like receptors (RLR), which patrol the cytoplasm for the presence of viral RNA. When double stranded RNA binds to an RLR, they form a complex with IPS1 via their CARD domains, leading to IPS1 multimerization and activation. Activated IPS1 complexes then recruit the IKK and TBK1/IKKi complexes, thereby triggering a signaling cascade that results in the activation of transcription factors NF-kappaB and IRF3. NF-kappaB and IRF3 bind to and activate the interferon promoter, resulting in a potent cell-mediated immune response via production of type 1 interferons. RIG-1 activation also activates the STING pathway, further enhancing cell-mediated immune responses against viruses. In the technology, fusion of IPS1 with the LMP1 N-terminal domain promotes LMP1-IPS1 clustering and activation that mimics activation by dsRNA.

Viral vectors of the present technology encode one or more nucleic acids sequences capable of activating or enhancing an immune response in a subject. The nucleic acids encode a latent membrane protein 1 (LMP1) of the Epstein Barr virus in which the intra-cytoplasmic domain has been replaced by human IPS1 or a variant thereof capable of activating the STING pathway. The LMP1 DNA sequence has been codon optimized for human expression. Expression of the LMP1-IPS1 fusion protein provides activation of immune responses by aggregation (i.e., multimerization) of two or more LMP1 proteins.

The viral vector can be any type of suitable vector, such as an expression vector or a plasmid. In preferred embodiments, the vector is a lentiviral vector. Lentiviral vectors are modified lentiviruses, derived, for example, from human immunodeficiency virus (HIV-1 or HIV-2), simian immunodeficiency virus (SIV), equine infectious encephalitis virus (EIAV), caprine arthritis encephalitis virus (CAEV), bovine immunodeficiency virus (BIV) and feline immunodeficiency virus (FIV). The modified lentiviral vectors have reduced pathogenicity. The vectors may also be modified to introduce beneficial therapeutic effects. Lentiviral vectors themselves are not toxic and, unlike other retroviruses, lentiviruses are capable of transducing non-dividing cells, in particular dendritic cells, allowing antigen presentation through the endogenous pathway.

Lentiviral vectors can include an RNA or DNA molecule. In some embodiments, the lentiviral vector is a recombinant DNA molecule, such as a plasmid. In some embodiments, the lentiviral vector includes a recombinant DNA molecule as well as associated viral proteins to form a particle. Lentiviral vector particles may contain single or double stranded nucleic acid molecules.

In preferred embodiments, the lentiviral vectors have the capacity for integration into the genome of the cells being transduced. In preferred embodiments, they contain a functional integrase protein. Non-integrating vector particles display genetic mutations that hinder the lentiviral vector particles capacity for integrating into the host genome. The term "transfection" and "transduction" refer to the process by which an exogenous DNA sequence is introduced into a eukaryotic host cell. Transfection is the non-viral delivery of nucleic acids (either DNA or RNA) and can be achieved by any one of a number of means including electroporation, microinjection, gene gun delivery, retroviral infection, lipofection, polymer-mediated delivery, and the like. Transduction refers to the delivery of nucleic acids by a virus or viral vector where the nucleic acids are typical DNA for a DNA virus and RNA for an RNA virus.

In some embodiments, the lentiviral vector is self-inactivating and does not contain an enhancer. Self-inactivating lentiviral vectors have modifications in the U3 (ΔU3) region of the 3' LTR that render the vectors unable to replicate in the host cell. The U3 region encodes binding sites that are essential for basal promoter activity and viral replication, and elimination of these binding sites results in virtually complete inactivation of viral replication.

Myriad factors can influence the efficacy of viral vectors, even after successful transduction and, optionally, integration into the host genome: gene expression and translation; protein folding, transport and turnover; and cell-to-cell interactions, to name a few. These factors depend, among other things, on the nucleic acid sequences encoded by the vector. Preferred DNA sequences for conducting the present technology include modifications of native sequences aimed at increasing viral vector efficacy and efficiency. These modifications include: codon optimization for human use; removal of the first methionine of IPS1 sequence in the fusion protein; removal of IPS1 transmembrane and proline-rich domains, as well as use of a reversed IPS1 sequence. These modifications may impact the rates of transcription and/or translation, as well as impact protein location in the cell and protein activity.

The viral vectors of the present technology encode one or more antigens. The term "antigen" as used herein refers to a molecule that provokes an immune response. This immune response may involve either antibody production, or the activation of specific immunologically-competent cells, or both. An antigen can be derived from organisms, subunits of proteins/antigens, killed or inactivated whole cells or lysates. Therefore, a skilled artisan realizes that any macromolecule, including virtually all proteins or peptides, can serve as antigens. Furthermore, antigens can be derived from recombinant or genomic DNA. A skilled artisan realizes that any DNA, which contains nucleotide sequences or partial nucleotide sequences of a pathogenic genome or a gene or a fragment of a gene for a protein that elicits an immune response results in synthesis of an antigen. Furthermore, one skilled in the art realizes that the present technology is not limited to the use of the entire nucleic acid sequence of a gene or genome. The present technology includes, but is not limited to, the use of partial nucleic acid sequences of more than one gene or genome whose nucleic acid sequences are arranged in various combinations to elicit the desired immune response.

The antigen may be any antigen for which an enhanced immune response is desirable. Such antigens include, but are not limited to, antigens from pathogens that cause infectious disease for which a protective immune response may be elicited. For example, antigens from HIV include the proteins gag, env, pol, tat, rev, nef, reverse transcriptase, and other HIV components. The E6 and E7 proteins from human papilloma virus are also suitable antigens. Furthermore, the EBNA1 antigen from herpes simplex virus is suitable. Other viral antigens for use in the technology are hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin, neuraminidase, nucleoprotein, M2, and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS 1, NS 1-NS2A, 80% E, and other Japanese encephalitis viral antigen components; rabies viral antigens such as rabies glycoprotein, rabies nucleoprotein and other rabies viral antigen components; West Nile virus prM and E proteins; and Ebola envelope protein. See Fundamental Virology, Second Edition, eds. Knipe, D. M. and, Howley P. M. (Lippincott Williams & Wilkins, New York, 2001) for additional examples of viral antigens. In addition, bacterial antigens are also disclosed. Bacterial antigens which can be used in the compositions and methods of the technology include, but are not limited to, pertussis bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; Staphylococcal bacterial antigens such as IsdA, IsdB, SdrD, and SdrE; gram-negative bacilli bacterial antigens such as lipopolysaccharides, flagellin, and other gram-negative bacterial antigen components; *Mycobacterium tuberculosis* bacterial antigens such as mycolic acid, heat shock protein 65 (HSP65), the 30 kDa major secreted protein, antigen 85A, ESAT-6, and other mycobacterial antigen components; Helicobacter pylori bacterial antigen components; pneumococcal bacterial antigens such as pneumolysin, pneumococcal capsular polysaccharides and other pneumococcal bacterial antigen components; haemophilus influenza bacterial antigens such as capsular polysaccharides and other haemophilus influenza bacterial antigen components; anthrax bacterial antigens such as anthrax protective antigen, anthrax lethal factor, and other anthrax bacterial antigen components; the F1 and V proteins from Yersinia pestis; rickettsiae bacterial antigens such as romps and other rickettsiae bacterial antigen components. Also included with the bacterial antigens described herein are any other bacterial, mycobacterial, mycoplasmal, rickettsial, or chlamydial antigens. Examples of protozoa and other parasitic antigens include, but are not limited to, *Plasmodium falciparum* antigens such as merozoite surface antigens, sporozoite surface antigens, circumsporozoite antigens, gametocyte/gamete surface antigens, blood-stage antigen pf 1 55/RESA and other plasmodial antigen components; toxoplasma antigens such as SAG-1, p30 and other toxoplasma antigen components; schistosomae antigens such as glutathione-S-transferase, paramyosin, and other schistosomal antigen components; *Leishmania major* and other leishmaniae antigens such as gp63, lipophosphoglycan and its associated protein and other leishmanial antigen components; and *Trypanosoma cruzi* antigens such as the 75-77 kDa antigen, the 56 kDa antigen and other trypanosomal antigen components. Examples of fungal antigens include, but are not limited to, antigens from *Candida* species, *Aspergillus* species, *Blastomyces* species, *Histoplasma* species, *Coccidiodomycosis* species, *Malassezia furfur* and other species, *Exophiala werneckii* and other species, *Piedraia hortai* and other species, *Trichosporum beigelii* and other species, *Microsporum* species, *Trichophyton* species, *Epidermophyton* species, *Sporothrix schenckii* and other species, *Fonsecaea pedrosoi* and other species, *Wangiella dermatitidis* and other species, *Pseudallescheria boydii* and other species, *Madurella grisea* and other species, *Rhizopus* species, *Absidia* species, and *Mucor* species. Examples of prion disease antigens include PrP, beta-amyloid, and other prion-associated proteins.

In addition to the infectious and parasitic agents mentioned above, another area for desirable enhanced immunogenicity to a non-infectious agent is inflammatory and autoimmune diseases, neurodegenerative diseases, and in the area of proliferative diseases, including but not limited to cancer, in which cells expressing cancer antigens are desirably eliminated from the body. Tumor antigens which can be used in the compositions and methods of the technology include, but are not limited to, prostate specific antigen (PSA), breast, ovarian, testicular, melanoma, telomerase; multidrug resistance proteins such as P-glycoprotein; MAGE-1, alpha fetoprotein, carcinoembryonic antigen, mutant p53, papillomavirus antigens, gangliosides or other carbohydrate-containing components of melanoma or other tumor cells. It is contemplated by the technology that antigens from any type of tumor cell can be used in the compositions and methods described herein. The antigen may be a cancer cell, or immunogenic materials isolated from a cancer cell, such as membrane proteins. Included are survivin and telomerase universal antigens and the MAGE family of cancer testis antigens. Antigens which have been shown to be involved in autoimmunity and could be used in the methods of the present technology to induce tolerance include, but are not limited to, myelin basic protein, myelin oligodendrocyte glycoprotein and proteolipid protein of multiple sclerosis and CII collagen protein of rheumatoid arthritis.

The antigen may be a portion of an infectious agent such as HIV-1, EBV, HBV, influenza virus, SARS virus, poxviruses, malaria, or HSV, by way of non-limiting examples, for which vaccines that mobilize strong T-cell mediated immunity (via dendritic cells) are needed.

The term "cancer" as used herein is defined as a hyperproliferation of cells whose unique trait—loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The term "tumor" denotes at least one cell or cell mass in the form of a tissue neoformation, in particular in the form of a spontaneous, autonomous and irreversible excess growth, which is more or less disinhibited, of endogenous tissue, which growth is as a rule associated with the more or less pronounced loss of specific cell and tissue functions. This cell or cell mass is not effectively inhibited, in regard to its growth, by itself or by the regulatory mechanisms of the host organism, e.g. melanoma or carcinoma. Tumor antigens not only include antigens present in or on the malignant cells themselves, but also include antigens present on the stromal supporting tissue of tumors including endothelial cells and other blood vessel components. In a related aspect, "neoplastic" refers to abnormal new growth and thus means the same as tumor, which may be benign or malignant. Further, such neoplasia would include cell proliferation disorders.

A lentiviral vector of the technology further comprises a nucleic acid sequence that encodes one or more adjuvants. In one embodiment, the DNA sequence encoding the full-length LMP1 with codon optimization for human use (LMP1 CO) includes SEQ ID NO. 1 (below). The encoded amino acid sequence of full length LMP1 is shown below as SEQ ID NO: 2.

(SEQ ID NO: 1)
ATGGATCTGGACCTGGAAAGAGGACCTCCTGGACCTAGACGGCCTCCTAG

AGGACCACCTCTGAGCAGCTCTATTGGACTGGCCCTGCTGCTGCTTCTGC

TGGCTCTGCTGTTCTGGCTGTACATCATCATGAGCAACTGGACCGGCGGA

GCACTGCTGGTGCTGTATGCCTTTGCTCTGATGCTGGTCATCATCATCCT

GATCATCTTCATCTTCCGGCGGGACCTGCTGTGTCCTCTGGGAGCACTTT

GTCTGTTGCTGCTGATGATCACCCTCCTGCTGATCGCCCTGTGGAACCTG

CATGGACAGGCCCTGTATCTGGGAATCGTGCTGTTCATCTTCGGCTGCCT

GCTGGTTCTCGGCCTGTGGATCTACCTGCTGGAAATCCTTTGGAGACTGG

GCGCCACCATCTGGCAGCTGCTGGCCTTTTTCCTGGCCTTCTTTCTGGAT

ATCATCCTCCTCATCATTGCCCTGTACCTGCAGCAGAACTGGTGGACCCT

GCTGGTGGATCTGCTTTGGCTGCTGCTCTTTCTGGCCACCTGATTTGGAT

GTACTACCACGGCCAGCGGCACAGCAGACGAACACCACCATGATGACAGC

CTGCCTCATCCTCAGCAGGCCACCGACGATAGCAGCAACCAGAGCGACAG

CAACAGCAACGAGGGCAGACATCTGCTGCTGGTGTCTGGTGCTGGCGACG

GACCTCCTCTGTGTTCTCAAAATCTTGGCGCCCCTGGCGGCGGACCAAAC

AATGGACCTCAGGACCCCGACAACACCGACGACAATGGCCCTCAAGATCC

TGATAATACCGATGACAACGGCCCACACGACCCTCTGCCTCAAGACCCAG

ATAACACAGACGATAACGGTCCACAAGATCCGGACAATACTGACGATAAT

GGACCCCACGATCCACTGCCTCACAACCCTAGCGATAGCGCCGGAAATGA

TGGCGGACCTCCACAGCTGACCGAGGAAGTGGAAAACAAAGGCGGAGATC

AGGGCCCTCCTCTGATGACCGATGGCGGAGGTGGACACTCTCACGATTCT

GGCCACGACGGCATCGACCCTCATCTGCCTACACTGCTGCTCGGCACATC

TGGCTCTGGCGGCGACGATGATGATCCTCATGGACCTGTGCAGCTGAGCT

ACTACGAC (SEQ ID NO: 2)
MDLDLERGPPGPRRPPRGPPLSSSIGLALLLLLLALLFWLYIIMSNWTGG

ALLVLYAFALMLVIILIIFIFRRDLLCPLGALCLLLLMITLLLIALWNL

HGQALYLGIVLFIFGCLLVLGLWIYLLEILWRLGATIWQLLAFFLAFFLD

IILLIIALYLQQNWWTLLVDLLWLLLFLAILIWMYYHGQRHSDEHHHDDS

LPHPQQATDDSSNQSDSNSNEGRHLLLVSGAGDGPPLCSQNLGAPGGGPN

NGPQDPDNTDDNGPQDPDNTDDNGPHDPLPQDPDNTDDNGPQDPDNTDDN

GPHDPLPHNPSDSAGNDGGPPQLTEEVENKGGDQGPPLMTDGGGGHSHDS

GHDGIDPHLPTLLLGTSGSGGDDDDPHGPVQLSYYD

A useful control genetic adjuvant is provided by a truncated form of LMP1 (LMP 1_CO delta IC) which has the intra-cytoplasmic signaling domain deleted. The DNA sequence of this form (codon optimized for expression in human cells) is shown below as SEQ ID NO:3, and the encoded amino acid sequence is shown as SEQ ID NO:4. The function of the signaling domain can be revealed by comparing the response to expression of SEQ ID NO:1 (including the signaling domain) to the response to expression of SEQ ID NO:3 (lacking the signaling domain).

(SEQ ID NO: 3)
ATGGATCTGGATCTCGAAAGAGGACCTCCTGGACCTAGACGGCCTCCTAG

AGGACCACCTCTGAGCAGCTCTATTGGACTGGCCCTGCTGCTGCTTCTGC

TGGCTCTGCTGTTCTGGCTGTACATCATCATGAGCAACTGGACCGGCGGA

GCACTGCTGGTGCTGTATGCCTTTGCTCTGATGCTGGTCATCATCATCCT

GATCATCTTCATCTTCCGGCGGGACCTGCTGTGTCCTCTGGGAGCACTTT

GTCTGTTGCTGCTGATGATCACCCTCCTGCTGATCGCCCTGTGGAACCTG

CATGGACAGGCCCTGTATCTGGGCATCGTGCTGTTCATCTTCGGCTGCCT

GCTGGTTCTCGGCCTGTGGATCTACCTGCTGGAAATCCTTTGGAGACTGG

GCGCCACCATCTGGCAGCTGCTGGCCTTTTTCCTGGCCTTCTTTCTGGAT

ATCATCCTCCTCATCATTGCCCTGTACCTGCAGCAGAACTGGTGGACCCT

GCTGGTGGATCTGCTTTGGCTGCTGCTCTTTCTGGCCATCCTGATTTGGA

TGTACTACCACGGCCAGCGG (SEQ ID NO: 4)
MDLDLERGPPGPRRPPRGPPLSSSIGLALLLLLLALLFWLYIIMSNWTGG

ALLVLYAFALMLVIIILIIFIFRRDLLCPLGALCLLLLMITLLLIALWNL

HGQALYLGIVLFIFGCLLVLGLWIYLLEILWRLGATIWQLLAFFLAFFLD

IILLIIALYLQQWWWTLLVDLLWLLLFLAILIWMYYHGQR

A preferred adjuvant is the fusion protein LMP1 (delta IC) hIPS1, which contains LMP1 from Epstein Barr virus, without the intracytoplasmic region, in fusion with the full length human IPS1. In the fusion protein, the first amino acid (methionine) of human IPS1 was removed. The fusion protein is codon optimized for human use. The DNA and encoded amino acid sequences of this fusion protein are shown below:
DNA sequence (SEQ ID NO: 5)
ATGGATCTGGATCTCGAAAGAGGACCTCCTGGACCTAGACGGCCTCCTAG

AGGACCACCTCTGAGCAGCTCTATTGGACTGGCCCTGCTGCTGCTTCTGC

TGGCTCTGCTGTTCTGGCTGTACATCATCATGAGCAACTGGACCGGCGGA

GCACTGCTGGTGCTGTATGCCTTTGCTCTGATGCTGGTCATCATCATCCT

GATCATCTTCATCTTCCGGCGGGACCTGCTGTGTCCTCTGGGAGCACTTT

GTCTGTTGCTGCTGATGATCACCCTCCTGCTGATCGCCCTGTGGAACCTG

CATGGACAGGCCCTGTATCTGGGCATCGTGCTGTTCATCTTCGGCTGCCT

GCTGGTTCTCGGCCTGTGGATCTACCTGCTGGAAATCCTTTGGAGACTGG

GCGCCACCATCTGGCAGCTGCTGGCCTTTTTCCTGGCCTTCTTTCTGGAT

ATCATCCTCCTCATCATTGCCCTGTACCTGCAGCAGAACTGGTGGACCCT

GCTGGTGGATCTGCTTTGGCTGCTGCTCTTTCTGGCCATCCTGATTTGGA

TGTACTACCACGGCCAGCGGCTTTCGCCGAGGACAAGACCTACAAGTAC

ATCTGCCGGAACTTCAGCAACTTCTGCAACGTGGACGTGGTGGAAATTCT

GCCCTACCTGCCTTGCCTGACCGCCAGAGATCAGGACAGACTGAGAGCCA

CATGTACCCTGAGCGGCAACAGAGACACACTGTGGCACCTGTTCAACACC

CTGCAGAGAAGGCCTGGCTGGGTCGAGTACTTTATCGCCGCTCTGAGAGG

CTGCCGAGCTGGTCGATCTGGCTGATGAAGTGGCCAGCGTGTACCAGAGCT

```
ACCAGCCTAGAACCAGCGACCGGCCTCCTGATCCTCTCGAACCTCCATCT
CTGCCCGCCGAAAGACCTGGACCTCCTACACCAGCTGCCGCTCACAGCAT
CCCTTACAACAGCTGCAGAGAGAAAGAACCTAGCTACCCCATGCCTGTGC
AAGAGACACAGGCCCCAGAAAGCCCTGGCGAGAATAGCGAACAGGCTCTG
CAGACACTGAGCCCCAGAGCCATTCCTAGAAACCCTGATGGCGGCCCTCT
GGAAAGCTCTAGTGATCTGGCCGCTCTGTCCCCTCTGACAAGCTCTGGAC
ACCAAGAGCAGGATACCGAGCTGGGCAGCACACATACAGCCGGCGCTACA
AGCAGCCTGACACCTTCTAGAGGCCCCGTGTCTCCCAGCGTGTCATTTCA
GCCTCTGGCCAGGTCTACCCCTAGGGCTTCTAGACTGCCTGGACCAACAG
GCAGCGTGGTGTCTACCGGCACAAGCTTCAGCTCTAGCTCTCCTGGACTG
GCTAGTGCCGGTGCCGCTGAGGGAAAACAAGGCGCCGAATCTGATCAGGC
CGAGCCTATCATCTGTAGCAGCGGAGCAGAAGCCCCTGCCAATAGCCTGC
CTAGCAAGGTGCCAACCACACTGATGCCCGTGAACACAGTGGCCCTGAAG
GTGCCAGCTAATCCTGCCTCCGTGTCCACCGTGCCTTCTAAGCTGCCAAC
CAGCTCTAAGCCACCTGGCGCCGTGCCATCTAACGCCCTGACAAATCCTG
CTCCAAGCAAGCTGCCCATCAACTCCACAAGAGCCGGCATGGTGCCCTCT
AAGGTGCCCACATCTATGGTGCTGACCAAGGTGTCCGCCAGCACCGTGCC
AACAGATGGCAGCTCCAGAAACGAGGAAACCCCTGCCGCTCCTACTCCTG
CTGGCGCTACAGGCGGATCTTCTGCTTGGCTGGATAGCAGCAGCGAGAAC
AGAGGCCTGGGCAGCGAGCTTTCTAAACCTGGCGTGCTGGCTTCCCAGGT
GGACAGCCCATTTTCCGGCTGCTTTGAGGACCTGGCTATCAGCGCCTCTA
CAAGCCTCGGCATGGGACCTTGTCACGGCCCCGAGGAAAACGAGTACAAG
AGCGAGGGCACCTTCGGCATCCACGTGGCCGAGAATCCTAGCATCCAACT
GCTGGAAGGCAACCCCGGACCTCCAGCTGATCCAGATGGCGGACCAAGAC
CTCAGGCCGACAGAAAGTTCCAAGAGCGCGAGGTGCCCTGCCACAGACCT
TCTCCAGGTGCTCTGTGGCTGCAGGTTGCAGTGACAGGCGTCCTGGTGGT
TACACTGCTCGTGGTCCTGTATAGACGGCGGCTGCAC
```

Protein sequence

```
                                           (SEQ ID NO: 6)
MDLDLERGPPGPRRPPRGPPLSSSIGLALLLLLLALLFWLYIIMSNWTGG

ALLVLYAFALMLVIIILIIFIFRRDLLCPLGALCLLLLMITLLLIALWNL

HGQALYLGIVLFIFGCLLVLGLWIYLLEILWRLGATIWQLLAFFLAFFLD

IILLIIALYLQQNWWTLLVDLLWLLLFLAILIWMYYHGQRPFAEDKTYKY

ICRNFSNFCNVDVVEILPYLPCLTARDQDRLRATCTLSGNRDTLWHLFNT

LQRRPGWVEYFIAALRGCELVDLADEVASVYQSYQPRTSDRPPDPLEPPS

LPAERPGPPTPAAAHSIPYNSCREKEPSYPMPVQETQAPESPGENSEQAL

QTLSPRAIPRNPDGGPLESSSDLAALSPLTSSGHQEQDTELGSTHTAGAT

SSLTPSRGPVSPSVSFQPLARSTPRASRLPGPTGSVVSTGTSFSSSSPGL

ASAGAAEGKQGAESDQAEPIICSSGAEAPANSLPSKVPTTLMPVNTVALK

VPANPASVSTVPSKLPTSSKPPGAVPSNALTNPAPSKLPINSTRAGMVPS
```

```
KVPTSMVLTKVSASTVPTDGSSRNEETPAAPTPAGATGGSSAWLDSSSEN

RGLGSELSKPGVLASQVDSPFSGCFEDLAISASTSLGMGPCHGPEENEYK

SEGTFGIHVAENPSIQLLEGNPGPPADPDGGPRPQADRKFQEREVPCHRP

SPGALWLQVAVTGVLVVTLLVVLYRRRLH
```

Another preferred adjuvant is the fusion protein LMP1 (delta IC) hIPS1 (deltaTM), which contains LMP1 from Epstein Barr virus, without the intracytoplasmic region, in fusion with amino acids 2-439 of human IPS1, without its transmembrane region. In the fusion protein, the first amino acid (methionine) of human IPS1 was removed. The fusion protein is codon optimized for human use. The DNA and encoded amino acid sequences of this fusion protein are shown below:

DNA sequence

```
                                           (SEQ ID NO: 7)
ATGGATCTGGATCTCGAAAGAGGACCTCCTGGACCTAGACGGCCTCCTAG

AGGACCACCTCTGAGCAGCTCTATTGGACTGGCCCTGCTGCTGCTTCTGC

TGGCTCTGCTGTTCTGGCTGTACATCATCATGAGCAACTGGACCGGCGGA

GCACTGCTGGTGCTGTATGCCTTTGCTCTGATGCTGGTCATCATCATCCT

GATCATCTTCATCTTCCGGCGGGACCTGCTGTGTCCTCTGGGAGCACTTT

GTCTGTTGCTGCTGATGATCACCCTCCTGCTGATCGCCCTGTGGAACCTG

CATGGACAGGCCCTGTATCTGGGCATCGTGCTGTTCATCTTCGGCTGCCT

GCTGGTTCTCGGCCTGTGGATCTACCTGCTGGAAATCCTTTGGAGACTGG

GCGCCACCATCTGGCAGCTGCTGGCCTTTTTCCTGGCCTTCTTTCTGGAT

ATCATCCTCCTCATCATTGCCCTGTACCTGCAGCAGAACTGGTGGACCCT

GCTGGTGGATCTGCTTTGGCTGCTGCTCTTTCTGGCCATCCTGATTTGGA

TGTACTACCACGGCCAGCGGCCTTTCGCCGAGGACAAGACCTACAAGTAC

ATCTGCCGGAACTTCAGCAACTTCTGCAACGTGGACGTGGTGGAAATTCT

GCCCTACCTGCCTTGCCTGACCGCCAGAGATCAGGACAGACTGAGAGCCA

CATGTACCCTGAGCGGCAACAGAGACACACTGTGGCACCTGTTCAACACC

CTGCAGAGAAGGCCTGGCTGGGTCGAGTACTTTATCGCCGCTCTGAGAGG

CTGCGAGCTGGTCGATCTGGCTGATGAAGTGGCCAGCGTGTACCAGAGCT

ACCAGCCTAGAACCAGCGACCGGCTCCTGATCCTCTCGAACCTCCATCT

CTGCCCGCCGAAAGACCTGGACCTCCTACACCAGCTGCCGCTCACAGCAT

CCCTTACAACAGCTGCAGAGAGAAAGAACCTAGCTACCCCATGCCTGTGC

AAGAGACACAGGCCCCAGAAAGCCCTGGCGAGAATAGCGAACAGGCTCTG

CAGACACTGAGCCCCAGAGCCATTCCTAGAAACCCTGATGGCGGCCCTCT

GGAAAGCTCTAGTGATCTGGCCGCTCTGTCCCCTCTGACAAGCTCTGGAC

ACCAAGAGCAGGATACCGAGCTGGGCAGCACACATACAGCCGGCGCTACA

AGCAGCCTGACACCTTCTAGAGGCCCCGTGTCTCCCAGCGTGTCATTTCA

GCCTCTGGCCAGGTCTACCCCTAGGGCTTCTAGACTGCCTGGACCAACAG

GCAGCGTGGTGTCTACCGGCACAAGCTTCAGCTCTAGCTCTCCTGGACTG

GCTAGTGCCGGTGCCGCTGAGGGAAAACAAGGCGCCGAATCTGATCAGGC
```

-continued

CGAGCCTATCATCTGTAGCAGCGGAGCAGAAGCCCCTGCCAATAGCCTGC

CTAGCAAGGTGCCAACCACACTGATGCCCGTGAACACAGTGGCCCTGAAG

GTGCCAGCTAATCCTGCCTCCGTGTCCACCGTGCCTTCTAAGCTGCCAAC

CAGCTCTAAGCCACCTGGCGCCGTGCCATCTAACGCCCTGACAAATCCTG

CTCCAAGCAAGCTGCCCATCAACTCCACAAGAGCCGGCATGGTGCCCTCT

AAGGTGCCCACATCTATGGTGCTGACCAAGGTGTCCGCCAGCACCGTGCC

AACAGATGGCAGCTCCAGAAACGAGGAAACCCCTGCCGCTCCTACTCCTG

CTGGCGCTACAGGCGGATCTTCTGCTTGGCTGGATAGCAGCAGCGAGAAC

AGAGGCCTGGGCAGCGAGCTTTCTAAACCTGGCGTGCTGGCTTCCCAGGT

GGACAGCCCATTTTCCGGCTGCTTTGAGGACCTGGCTATCAGCGCCTCTA

CAAGCCTCGGCATGGGACCTTGTCACGGCCCCGAGGAAAACGAGTACAAG

AGCGAGGGCACCTTCGGCATCCACGTGGCCGAGAATCCTAGCATCCAACT

GCTGGAAGGCAACCCCGGACCTCCAGCTGATCCAGATGGCGGACCAAGAC

CTCAGGCCGACAGAAAGTTCCAAGAGCGCGAGGTGCCCTGCCACAGACCT

TCTCCA

Protein sequence (SEQ ID NO: 8)
MDLDLERGPPGPRRPPRGPPLSSSIGLALLLLLLALLFWLYIIMSNWTGG

ALLVLYAFALMLVIIILIIFIFRRDLLCPLGALCLLLLMITLLLIALWNL

HGQALYLGIVLFIFGCLLVLGLWIYLLEILWRLGATIWQLLAFFLAFFLD

IILLIIALYLQQNWWTLLVDLLWLLLFLAILIWMYYHGQRPFAEDKTYKY

ICRNFSNFCNVDVVEILPYLPCLTARDQDRLRATCTLSGNRDTLWHLFNT

LQRRPGWVEYFIAALRGCELVDLADEVASVYQSYQPRTSDRPPDPLEPPS

LPAERPGPPTPAAAHSIPYNSCREKEPSYPMPVQETQAPESPGENSEQAL

QTLSPRAIPRNPDGGPLESSSDLAALSPLTSSGHQEQDTELGSTHTAGAT

SSLTPSRGPVSPSVSFQPLARSTPRASRLPGPTGSVVSTGTSFSSSSPGL

ASAGAAEGKQGAESDQAEPIICSSGAEAPANSLPSKVPTTLMPVNTVALK

VPANPASVSTVPSKLPTSSKPPGAVPSNALTNPAPSKLPINSTRAGMVPS

KVPTSMVLTKVSASTVPTDGSSRNEETPAAPTPAGATGGSSAWLDSSSEN

RGLGSELSKPGVLASQVDSPFSGCFEDLAISASTSLGMGPCHGPEENEYK

SEGTFGIHVAENPSIQLLEGNPGPPADPDGGPRPQADRKFQEREVPCHRP

SP

Another preferred adjuvant is the fusion protein LMP1 (delta IC) hIPS1 (delta TM delta Pro), which contains LMP1 from Epstein Barr virus, without the intracytoplasmic region, in fusion with amino acids 2-93 of human IPS1 (a truncated IP S1 with the C terminal proline-rich and transmembrane domains removed). In the fusion protein, the first amino acid (methionine) of human IPS1 was removed. The fusion protein is codon optimized for human use. The DNA and encoded amino acid sequences of this fusion protein are shown below:

DNA sequence (SEQ ID NO: 9)
ATGGATCTGGATCTCGAAAGAGGACCTCCTGGACCTAGACGGCCTCCTAG

AGGACCACCTCTGAGCAGCTCTATTGGACTGGCCCTGCTGCTGCTTCTGC

TGGCTCTGCTGTTCTGGCTGTACATCATCATGAGCAACTGGACCGGCGGA

GCACTGCTGGTGCTGTATGCCTTTGCTCTGATGCTGGTCATCATCATCCT

GATCATCTTCATCTTCCGGCGGGACCTGCTGTGTCCTCTGGGAGCACTTT

GTCTGTTGCTGCTGATGATCACCCTCCTGCTGATCGCCCTGTGGAACCTG

CATGGACAGGCCCTGTATCTGGGCATCGTGCTGTTCATCTTCGGCTGCCT

GCTGGTTCTCGGCCTGTGGATCTACCTGCTGGAAATCCTTTGGAGACTGG

GCGCCACCATCTGGCAGCTGCTGGCCTTTTTCCTGGCCTTCTTTCTGGAT

ATCATCCTCCTCATCATTGCCCTGTACCTGCAGCAGAACTGGTGGACCCT

GCTGGTGGATCTGCTTTGGCTGCTGCTCTTTCTGGCCATCCTGATTTGGA

TGTACTACCACGGCCAGCGGCCTTTCGCCGAGGACAAGACCTACAAGTAC

ATCTGCCGGAACTTCAGCAACTTCTGCAACGTGGACGTGGTGGAAATTCT

GCCCTACCTGCCTTGCCTGACCGCCAGAGATCAGGACGACTGAGAGCCA

CATGTACCCTGAGCGGCAACAGAGACACACTGTGGCACCTGTTCAACACC

CTGCAGAGAAGGCCTGGCTGGGTCGAGTACTTTATCGCCGCTCTGAGAGG

CTGCGAGCTGGTCGATCTGGCTGATGAAGTGGCCAGCGTGTACCAGAGCT

ACCAGCCTAGAACCAGCGACCGGGGCGAGAATAGCGAACAGGCTCTGCAG

ACACTGAGCCCCAGAGCCATTCCTAGAAACCCTGATGGCGGCCCTCTGGA

AAGCTCTAGTGATCTGGCCGCTCTGTCCCCTCTGACAAGCTCTGGACACC

AAGAGCAGGATACCGAGCTGGGCAGCACACATACAGCCGGCGCTACAAGC

AGCCTGACACCTTCTAGAGGCCCCGTGTCTCCCAGCGTGTCATTTCAGCC

TCTGGCCAGGTCTACCCCTAGGGCTTCTAGACTGCCTGGACCAACAGGCA

GCGTGGTGTCTACCGGCACAAGCTTCAGCTCTAGCTCTCCTGGACTGGCT

AGTGCCGGTGCCGCTGAGGGAAAACAAGGCGCCGAATCTGATCAGGCCGA

GCCTATCATCTGTAGCAGCGGAGCAGAAGCCCCTGCCAATAGCCTGCCTA

GCAAGGTGCCAACCACACTGATGCCCGTGAACACAGTGGCCCTGAAGGTG

CCAGCTAATCCTGCCTCCGTGTCCACCGTGCCTTCTAAGCTGCCAACCAG

CTCTAAGCCACCTGGCGCCGTGCCATCTAACGCCCTGACAAATCCTGCTC

CAAGCAAGCTGCCCATCAACTCCACAAGAGCCGGCATGGTGCCCTCTAAG

GTGCCCACATCTATGGTGCTGACCAAGGTGTCCGCCAGCACCGTGCCAAC

AGATGGCAGCTCCAGAAACGAGGAAACCCCTGCCGCTCCTACTCCTGCTG

GCGCTACAGGCGGATCTTCTGCTTGGCTGGATAGCAGCAGCGAGAACAGA

GGCCTGGGCAGCGAGCTTTCTAAACCTGGCGTGCTGGCTTCCCAGGTGGA

CAGCCCATTTTCCGGCTGCTTTGAGGACCTGGCTATCAGCGCCTCTACAA

GCCTCGGCATGGGACCTTGTCACGGCCCCGAGGAAAACGAGTACAAGAGC

GAGGGCACCTTCGGCATCCACGTGGCCGAGAATCCTAGCATCCAACTGCT

-continued

GGAAGGCAACCCCGGACCTCCAGCTGATCCAGATGGCGGACCAAGACCTC

AGGCCGACAGAAAGTTCCAAGAGCGCGAGGTGCCCTGCCACAGACCTTCT

CCA

Protein sequence (SEQ ID NO: 10)
MDLDLERGPPGPRRPPRGPPLSSSIGLALLLLLLALLFWLYIIMSNWTGG

ALLVLYAFALMLVIILIIFIFRRDLLCPLGALCLLLLMITLLLIALWNL

HGQALYLGIVLFIFGCLLVLGLWIYLLEILWRLGATIWQLLAFFLAFFLD

IILLIIALYLQQNWWTLLVDLLWLLLFLAILIWMYYHGQRPFAEDKTYKY

ICRNFSNFCNVDVVEILPYLPCLTARDQDRLRATCTLSGNRDTLWHLFNT

LQRRPGWVEYFIAALRGCELVDLADEVASVYQSYQPRTSDRGENSEQALQ

TLSPRAIPRNPDGGPLESSSDLAALSPLTSSGHQEQDTELGSTHTAGATS

SLTPSRGPVSPSVSFQPLARSTPRASRLPGPTGSVVSTGTSFSSSSPGLA

SAGAAEGKQGAESDQAEPIICSSGAEAPANSLPSKVPTTLMPVNTVALKV

PANPASVSTVPSKLPTSSKPPGAVPSNALTNPAPSKLPINSTRAGMVPSK

VPTSMVLTKVSASTVPTDGSSRNEETPAAPTPAGATGGSSAWLDSSSENR

GLGSELSKPGVLASQVDSPFSGCFEDLAISASTSLGMGPCHGPEENEYKS

EGTFGIHVAENPSIQLLEGNPGPPADPDGGPRPQADRKFQEREVPCHRPS

P

Another preferred adjuvant is the fusion protein LMP1 (delta IC) hIPS1 reversed (delta TM), which contains LMP1 from Epstein Barr virus, without the intracytoplasmic region. in fusion with amino acids 2-439 of human IPS1 (a truncated IPS1 with the transmembrane domain removed and presented in reverse amino acid order, i.e., 439 to 2, C-terminal to N-terminal direction of native IPS1). In the fusion protein, the first amino acid (methionine) of human IPS1 (as encoded by the natural direct DNA) was removed. The fusion protein is codon optimized for human use. The DNA and encoded amino acid sequences of this fusion protein are shown below:

DNA sequence:

(SEQ ID NO: 11)
ATGGATCTGGATCTCGAAAGAGGACCTCCTGGACCTAGACGGCCTCCTAG

AGGACCACCTCTGAGCAGCTCTATTGGACTGGCCCTGCTGCTGCTTCTGC

TGGCTCTGCTGTTCTGGCTGTACATCATCATGAGCAACTGGACCGGCGGA

GCACTGCTGGTGCTGTATGCCTTTGCTCTGATGCTGGTCATCATCATCCT

GATCATCTTCATCTTCCGGCGGGACCTGCTGTGTCCTCTGGGAGCACTTT

GTCTGTTGCTGCTGATGATCACCCTCCTGCTGATCGCCCTGTGGAACCTG

CATGGACAGGCCCTGTATCTGGGCATCGTGCTGTTCATCTTCGGCTGCCT

GCTGGTTCTCGGCCTGTGGATCTACCTGCTGGAAATCCTTTGGAGACTGG

GCGCCACCATCTGGCAGCTGCTGGCCTTTTTCCTGGCCTTCTTTCTGGAT

ATCATCCTCCTCATCATTGCCCTGTACCTGCAGCAGAACTGGTGGACCCT

GCTGGTGGATCTGCTTTGGCTGCTGCTCTTTCTGGCCATCCTGATTTGGA

TGTACTACCACGGCCAGCGGCCCAGCCCCAGACACTGCCCCGTGGAGAGA

GAGCAGTTCAAGAGAGACGCCCAGCCCAGACCCGGCGGCGACCCCGACGC

CCCCCCCGGCCCCAACGGCGAGCTGCTGCAGATCAGCCCCAACGAGGCCG

TGCACATCGGCTTCACCGGCGAGAGCAAGTACGAGAACGAGGAGCCCGGC

CACTGCCCCGGCATGGGCCTGAGCACCAGCGCCAGCATCGCCCTGGACGA

GTTCTGCGGCAGCTTCCCCAGCGACGTGCAGAGCGCCCTGGTGGGCCCCA

AGAGCCTGGAGAGCGGCCTGGGCAGAAACGAGAGCAGCAGCGACCTGTGG

GCCAGCAGCGGCGGCACCGCCGGCGCCCCCACCCCCGCCGCCCCCACCGA

GGAGAACAGAAGCAGCGGCGACACCCCCGTGACCAGCGCCAGCGTGAAGA

CCCTGGTGATGAGCACCCCCGTGAAGAGCCCCGTGATGGGCGCCAGAACC

AGCAACATCCCCCTGAAGAGCCCCGCCCCAACACCCTGGCCAACAGCCC

CGTGGCCGGCCCCCCCAAGAGCAGCACCCCCCTGAAGAGCCCCGTGACCA

GCGTGAGCGCCCCCAACGCCCCCGTGAAGCTGGCCGTGACCAACGTGCCC

ATGCTGACCACCCCCGTGAAGAGCCCCCTGAGCAACGCCCCCGCCGAGGC

CGGCAGCAGCTGCATCATCCCCGAGGCCCAGGACAGCGAGGCCGGCCAGA

AGGGCGAGGCCGCCGGCGCCAGCGCCCTGGGCCCCAGCAGCAGCAGCTTC

AGCACCGGCACCAGCGTGGTGAGCGGCACCCCCGGCCCCCTGAGAAGCGC

CAGACCCACCAGCAGAGCCCTGCCCCAGTTCAGCGTGAGCCCCAGCGTGC

CCGGCAGAAGCCCCACCCTGAGCAGCACCGCCGGCGCCACCCACACCAGC

GGCCTGGAGACCGACCAGGAGCAGCACGGCAGCAGCACCCTGCCCAGCCT

GGCCGCCCTGGACAGCAGCAGCGAGCTGCCCGGCGGCGACCCCAACAGAC

CCATCGCCAGACCCAGCCTGACCCAGCTGGCCCAGGAGAGCAACGAGGGC

CCCAGCGAGCCCGCCCAGACCGAGCAGGTGCCCATGCCCTACAGCCCCGA

GAAGGAGAGATGCAGCAACTACCCCATCAGCCACGCCGCCGCCCCCACCC

CCCCCGGCCCCAGAGAGGCCCCCCTGAGCCCCCCCGAGCTGCCCGACCCC

CCCAGAGACAGCACCAGACCCCAGTACAGCCAGTACGTGAGCGCCGTGGA

GGACGCCCTGGACGTGCTGGAGTGCGGCAGACTGGCCGCCATCTTCTACG

AGGTGTGGGCCCCAGAAGACAGCTGACCAACTTCCTGCACTGGCTGACC

GACAGAAACGGCAGCCTGACCTGCACCGCCAGACTGAGAGACCAGGACAG

AGCCACCCTGTGCCCCCTGTACCCCCTGATCGAGGTGGTGGACGTGAACT

GCTTCAACAGCTTCAACAGATGCATCTACAAGTACACCAAGGACGAGGCC

TTCCCCATG

Protein sequence (SEQ ID NO: 12)
MDLDLERGPPGPRRPPRGPPLSSSIGLALLLLLLALLFWLYIIMSNWTGG

ALLVLYAFALMLVIILIIFIFRRDLLCPLGALCLLLLMITLLLIALWNL

HGQALYLGIVLFIFGCLLVLGLWIYLLEILWRLGATIWQLLAFFLAFFLD

IILLIIALYLQQNWWTLLVDLLWLLLFLAILIWMYYHGQRPSPRHCPVER

EQFKRDAQPRPGGDPDAPPGPNGELLQISPNEAVHIGFTGESKYENEEPG

HCPGMGLSTSASIALDEFCGSFPSDVQSALVGPKSLESGLGRNESSSDLW

-continued
ASSGGTAGAPTPAAPTEENRSSGDTPVTSASVKTLVMSTPVKSPVMGART

SNIPLKSPAPNTLANSPVAGPPKSSTPLKSPVTSVSAPNAPVKLAVTNVP

MLTTPVKSPLSNAPAEAGSSCIIPEAQDSEAGQKGEAAGASALGPSSSSF

STGTSVVSGTPGPLRSARPTSRALPQFSVSPSVPGRSPTLSSTAGATHTS

GLETDQEQHGSSTLPSLAALDSSSELPGGDPNRPIARPSLTQLAQESNEG

PSEPAQTEQVPMPYSPEKERCSNYPISHAAAPTPPGPREAPLSPPELPDP

PRDSTRPQYSQYVSAVEDALDVLECGRLAAIFYEVWGPRRQLTNFLHWLT

DRNGSLTCTARLRDQDRATLCPLYPLIEVVDVNCFNSFNRCIYKYTKDEA

FPM

Another preferred adjuvant is the fusion protein LMP1 hIPS1 (delta TM), which contains full length LMP1 from Epstein Barr virus in fusion with amino acids 2-513 of human IPS1 (a truncated hIPS1 with the C terminal transmembrane domain removed. In the fusion protein, the first amino acid (methionine) of human IPS1 was removed. The fusion protein is codon optimized for human use. The DNA and encoded amino acid sequences of this fusion protein are shown below:

DNA Sequence (SEQ ID NO: 13)
ATGGATCTGGACCTGGAAAGAGGACCTCCTGGACCTAGACGGCCTCCTAG

AGGACCACCTCTGAGCAGCTCTATTGGACTGGCCCTGCTGCTGCTTCTGC

TGGCTCTGCTGTTCTGGCTGTACATCATCATGAGCAACTGGACCGGCGGA

GCACTGCTGGTGCTGTATGCCTTTGCTCTGATGCTGGTCATCATCATCCT

GATCATCTTCATCTTCCGGCGGGACCTGCTGTGTCCTCTGGGAGCACTTT

GTCTGTTGCTGCTGATGATCACCCTCCTGCTGATCGCCCTGTGGAACCTG

CATGGACAGGCCCTGTATCTGGGAATCGTGCTGTTCATCTTCGGCTGCCT

GCTGGTTCTCGGCCTGTGGATCTACCTGCTGGAAATCCTTTGGAGACTGG

GCGCCACCATCTGGCAGCTGCTGGCCTTTTTCCTGGCCTTCTTTCTGGAT

ATCATCCTCCTCATCATTGCCCTGTACCTGCAGCAGAACTGGTGGACCCT

GCTGGTGGATCTGCTTTGGCTGCTGCTCTTTCTGGCCATCCTGATTTGGA

TGTACTACCACGGCCAGCGGCACAGCGACGAACACCACCATGATGACAGC

CTGCCTCATCCTCAGCAGGCCACCGACGATAGCAGCAACCAGAGCGACAG

CAACAGCAACGAGGGCAGACATCTGCTGCTGGTGTCTGGTGCTGGCGACG

GACCTCCTCTGTGTTCTCAAAATCTTGGCGCCCCTGGCGGCGGACCAAAC

AATGGACCTCAGGACCCCGACAACACCGACGACAATGGCCCTCAAGATCC

TGATAATACCGATGACAACGGCCCACACGACCCTCTGCCTCAAGACCCAG

ATAACACAGACGATAACGGTCCACAAGATCCGGACAATACTGACGATAAT

GGACCCCACGATCCACTGCCTCACAACCCTAGCGATAGCGCCGGAAATGA

TGGCGGACCTCCACAGCTGACCGAGGAAGTGGAAAACAAAGGCGGAGATC

AGGGCCCTCCTCTGATGACCGATGGCGGAGGTGGACACTCTCACGATTCT

GGCCACGACGGCATCGACCCTCATCTGCCTACACTGCTGCTCGGCACATC

TGGCTCTGGCGGCGACGATGATGATCCTCATGGACCTGTGCAGCTGAGCT

ACTACGACCCTTTCGCCGAGGACAAGACCTACAAGTACATCTGCCGGAAC

-continued
TTCAGCAACTTCTGCAACGTGGACGTGGTGGAAATTCTGCCCTACCTGCC

TTGCCTGACCGCCAGAGATCAGGACAGACTGAGAGCCACATGTACCCTGA

GCGGCAACAGAGACACACTGTGGCACCTGTTCAACACCCTGCAGAGAAGG

CCTGGCTGGGTCGAGTACTTTATCGCCGCTCTGAGAGGCTGCGAGCTGGT

CGATCTGGCTGATGAAGTGGCCAGCGTGTACCAGAGCTACCAGCCTAGAA

CCAGCGACCGGCCTCCTGATCCTCTCGAACCTCCATCTCTGCCCGCCGAA

AGACCTGGACCTCCTACACCAGCTGCCGCTCACAGCATCCCTTACAACAG

CTGCAGAGAGAAAGAACCTAGCTACCCCATGCCTGTGCAAGAGACACAGG

CCCCAGAAAGCCCTGGCGAGAATAGCGAACAGGCTCTGCAGACACTGAGC

CCCAGAGCCATTCCTAGAAACCCTGATGGCGGCCCTCTGGAAAGCTCTAG

TGATCTGGCCGCTCTGTCCCCTCTGACAAGCTCTGGACACCAAGAGCAGG

ATACCGAGCTGGGCAGCACACATACAGCCGGCGCTACAAGCAGCCTGACA

CCTTCTAGAGGCCCCGTGTCTCCCAGCGTGTCATTTCAGCCTCTGGCCAG

GTCTACCCCTAGGGCTTCTAGACTGCCTGGACCAACAGGCAGCGTGGTGT

CTACCGGCACAAGCTTCAGCTCTAGCTCTCCTGGACTGGCTAGTGCCGGT

GCCGCTGAGGGAAAACAAGGCGCCGAATCTGATCAGGCCGAGCCTATCAT

CTGTAGCAGCGGAGCAGAAGCCCCTGCCAATAGCCTGCCTAGCAAGGTGC

CAACCACACTGATGCCCGTGAACACAGTGGCCCTGAAGGTGCCAGCTAAT

CCTGCCTCCGTGTCCACCGTGCCTTCTAAGCTGCCAACCAGCTCTAAGCC

ACCTGGCGCCGTGCCATCTAACGCCCTGACAAATCCTGCTCCAAGCAAGC

TGCCCATCAACTCCACAAGAGCCGGCATGGTGCCCTCTAAGGTGCCCACA

TCTATGGTGCTGACCAAGGTGTCCGCCAGCACCGTGCCAACAGATGGCAG

CTCCAGAAACGAGGAAACCCCTGCCGCTCCTACTCCTGCTGGCGCTACAG

GCGGATCTTCTGCTTGGCTGGATAGCAGCAGCGAGAACAGAGGCCTGGGC

AGCGAGCTTTCTAAACCTGGCGTGCTGGCTTCCCAGGTGGACAGCCCATT

TTCCGGCTGCTTTGAGGACCTGGCTATCAGCGCCTCTACAAGCCTCGGCA

TGGGACCTTGTCACGGCCCCGAGGAAAACGAGTACAAGAGCGAGGGCACC

TTCGGCATCCACGTGGCCGAGAATCCTAGCATCCAACTGCTGGAAGGCAA

CCCCGGACCTCCAGCTGATCCAGATGGCGGACCAAGACCTCAGGCCGACA

GAAAGTTCCAAGAGCGCGAGGTGCCCTGCCACAGACCTTCTCCA

Protein Sequence (SEQ ID NO: 14)
MDLDLERGPPGPRRPPRGPPLSSSIGLALLLLLLALLFWLYIIMSNWTGG

ALLVLYAFALMLVIILIIFIFRRDLLCPLGALCLLLLMITLLLIALWNL

HGQALYLGIVLFIFGCLLVLGLWIYLLEILWRLGATIWQLLAFFLAFFLD

IILLIIALYLQQNWWTLLVDLLWLLLFLAILIWMYYHGQRHSDEHHHDDS

LPHPQQATDDSSNQSDSNSNEGRHLLLVSGAGDGPPLCSQNLGAPGGGPN

NGPQDPDNTDDNGPQDPDNTDDNGPHDPLPQDPDNTDDNGPQDPDNTDDN

GPHDPLPHNPSDSAGNDGGPPQLTEEVENKGGDQGPPLMTDGGGGHSHDS

GHDGIDPHLPTLLLGTSGSGGDDDDPHGPVQLSYYDPFAEDKTYKYICRN

FSNFCNVDVVEILPYLPCLTARDQDRLRATCTLSGNRDTLWHLFNTLQRR

PGWVEYFIAALRGCELVDLADEVASVYQSYQPRTSDRPPDPLEPPSLPAE

RPGPPTPAAAHSIPYNSCREKEPSYPMPVQETQAPESPGENSEQALQTLS

PRAIPRNPDGGPLESSSDLAALSPLTSSGHQEQDTELGSTHTAGATSSLT

PSRGPVSPSVSFQPLARSTPRASRLPGPTGSVVSTGTSFSSSSPGLASAG

AAEGKQGAESDQAEPIICSSGAEAPANSLPSKVPTTLMPVNTVALKVPAN

PASVSTVPSKLPTSSKPPGAVPSNALTNPAPSKLPINSTRAGMVPSKVPT

SMVLTKVSASTVPTDGSSRNEETPAAPTPAGATGGSSAWLDSSSENRGLG

SELSKPGVLASQVDSPFSGCFEDLAISASTSLGMGPCHGPEENEYKSEGT

FGIHVAENPSIQLLEGNPGPPADPDGGPRPQADRKFQEREVPCHRPSP

The bolded portion of SEQ ID NOS:13 & 14 represents the proline-rich domain.

Another preferred adjuvant is the fusion protein LMP1 hIPS1 (delta Pro Delta TM), which contains full length LMP1 from Epstein Barr virus in fusion with amino acids 2-462 human IPS1 modified from which the proline-rich domain and the transmembrane domain are removed. In the fusion protein, the first amino acid (methionine) of human IPS1 was removed. The fusion protein is codon optimized for human use. The DNA and encoded amino acid sequences of this fusion protein are shown below:

DNA Sequence (SEQ ID NO: 15)
ATGGATCTGGACCTGGAAAGAGGACCTCCTGGACCTAGACGGCCTCCTAG

AGGACCACCTCTGAGCAGCTCTATTGGACTGGCCCTGCTGCTGCTTCTGC

TGGCTCTGCTGTTCTGGCTGTACATCATCATGAGCAACTGGACCGGCGGA

GCACTGCTGGTGCTGTATGCCTTTGCTCTGATGCTGGTCATCATCATCCT

GATCATCTTCATCTTCCGGCGGGACCTGCTGTGTCCTCTGGGAGCACTTT

GTCTGTTGCTGCTGATGATCACCCTCCTGCTGATCGCCCTGTGGAACCTG

CATGGACAGGCCCTGTATCTGGGAATCGTGCTGTTCATCTTCGGCTGCCT

GCTGGTTCTCGGCCTGTGGATCTACCTGCTGGAAATCCTTTGGAGACTGG

GCGCCACCATCTGGCAGCTGCTGGCCTTTTTCCTGGCCTTCTTTCTGGAT

ATCATCCTCCTCATCATTGCCCTGTACCTGCAGCAGAACTGGTGGACCCT

GCTGGTGGATCTGCTTTGGCTGCTGCTCTTTCTGGCCATCCTGATTTGGA

TGTACTACCACGGCCAGCGGCACAGCGACGAACACCACCATGATGACAGC

CTGCCTCATCCTCAGCAGGCCACCGACGATAGCAGCAACCAGAGCGACAG

CAACAGCAACGAGGGCAGACATCTGCTGCTGGTGTCTGGTGCTGGCGACG

GACCTCCTCTGTGTTCTCAAAATCTTGGCGCCCCTGGCGGCGGACCAAAC

AATGGACCTCAGGACCCCGACAACACCGACGACAATGGCCCTCAAGATCC

TGATAATACCGATGACAACGGCCCACACGACCCTCTGCCTCAAGACCCAG

ATAACACAGACGATAACGGTCCACAAGATCCGGACAATACTGACGATAAT

GGACCCCACGATCCACTGCCTCACAACCCTAGCGATAGCGCCGGAAATGA

TGGCGGACCTCCACAGCTGACCGAGGAAGTGGAAAACAAAGGCGGAGATC

AGGGCCCTCCTCTGATGACCGATGGCGGAGGTGGACACTCTCACGATTCT

GGCCACGACGGCATCGACCCTCATCTGCCTACACTGCTGCTCGGCACATC

TGGCTCTGGCGGCGACGATGATGATCCTCATGGACCTGTGCAGCTGAGCT

ACTACGACCCTTTCGCCGAGGACAAGACCTACAAGTACATCTGCCGGAAC

TTCAGCAACTTCTGCAACGTGGACGTGGTGGAAATTCTGCCCTACCTGCC

TTGCCTGACCGCCAGAGATCAGGACAGACTGAGAGCCACATGTACCCTGA

GCGGCAACAGAGACACACTGTGGCACCTGTTCAACACCCTGCAGAGAAGG

CCTGGCTGGGTCGAGTACTTTATCGCCGCTCTGAGAGGCTGCGAGCTGGT

CGATCTGGCTGATGAAGTGGCCAGCGTGTACCAGAGCTACCAGCCTAGAA

CCAGCGACCGGGGCGAGAATAGCGAACAGGCTCTGCAGACACTGAGCCCC

AGAGCCATTCCTAGAAACCCTGATGGCGGCCCTCTGGAAAGCTCTAGTGA

TCTGGCCGCTCTGTCCCCTCTGACAAGCTCTGGACACCAAGAGCAGGATA

CCGAGCTGGGCAGCACACATACAGCCGGCGCTACAAGCAGCCTGACACCT

TCTAGAGGCCCCGTGTCTCCCAGCGTGTCATTTCAGCCTCTGGCCAGGTC

TACCCCTAGGGCTTCTAGACTGCCTGGACCAACAGGCAGCGTGGTGTCTA

CCGGCACAAGCTTCAGCTCTAGCTCTCCTGGACTGGCTAGTGCCGGTGCC

GCTGAGGGAAAACAAGGCGCCGAATCTGATCAGGCCGAGCCTATCATCTG

TAGCAGCGGAGCAGAAGCCCCTGCCAATAGCCTGCCTAGCAAGGTGCCAA

CCACACTGATGCCCGTGAACACAGTGGCCCTGAAGGTGCCAGCTAATCCT

GCCTCCGTGTCCACCGTGCCTTCTAAGCTGCCAACCAGCTCTAAGCCACC

TGGCGCCGTGCCATCTAACGCCCTGACAAATCCTGCTCCAAGCAAGCTGC

CCATCAACTCCACAAGAGCCGGCATGGTGCCCTCTAAGGTGCCCACATCT

ATGGTGCTGACCAAGGTGTCCGCCAGCACCGTGCCAACAGATGGCAGCTC

CAGAAACGAGGAAACCCCTGCCGCTCCTACTCCTGCTGGCGCTACAGGCG

GATCTTCTGCTTGGCTGGATAGCAGCAGCGAGAACAGAGGCCTGGGCAGC

GAGCTTTCTAAACCTGGCGTGCTGGCTTCCCAGGTGGACAGCCCATTTTC

CGGCTGCTTTGAGGACCTGGCTATCAGCGCCTCTACAAGCCTCGGCATGG

GACCTTGTCACGGCCCCGAGGAAAACGAGTACAAGAGCGAGGGCACCTTC

GGCATCCACGTGGCCGAGAATCCTAGCATCCAACTGCTGGAAGGCAACCC

CGGACCTCCAGCTGATCCAGATGGCGGACCAAGACCTCAGGCCGACAGAA

AGTTCCAAGAGCGCGAGGTGCCCTGCCACAGACCTTCTCCA

Protein Sequence (SEQ ID NO: 16)
MDLDLERGPPGPRRPPRGPPLSSSIGLALLLLLLALLFWLYIIMSNWTGG

ALLVLYAFALMLVIILIIFIFRRDLLCPLGALCLLLLMITLLLIALWNL

HGQALYLGIVLFIFGCLLVLGLWIYLLEILWRLGATIWQLLAFFLAFFLD

IILLIIALYLQQNWWTLLVDLLWLLLFLAILIWMYYHGQRHSDEHHHDDS

LPHPQQATDDSSNQSDSNSNEGRHLLLVSGAGDGPPLCSQNLGAPGGGPN

NGPQDPDNTDDNGPQDPDNTDDNGPHDPLPQDPDNTDDNGPQDPDNTDDN

GPHDPLPHNPSDSAGNDGPPQLTEEVENKGGDQGPPLMTDGGGGHSHDS

GHDGIDPHLPTLLLGTSGSGGDDDDPHGPVQLSYYDPFAEDKTYKYICRN

FSNFCNVDVVEILPYLPCLTARDQDRLRATCTLSGNRDTLWHLFNTLQRR

PGWVEYFIAALRGCELVDLADEVASVYQSYQPRTSDRGENSEQALQTLSP

RAIPRNPDGGPLESSSDLAALSPLTSSGHQEQDTELGSTHTAGATSSLTP

SRGPVSPSVSFQPLARSTPRASRLPGPTGSVVSTGTSFSSSSPGLASAGA

AEGKQGAESDQAEPIICSSGAEAPANSLPSKVPTTLMPVNTVALKVPANP

ASVSTVPSKLPTSSKPPGAVPSNALTNPAPSKLPINSTRAGMVPSKVPTS

MVLTKVSASTVPTDGSSRNEETPAAPTPAGATGGSSAWLDSSSENRGLGS

ELSKPGVLASQVDSPFSGCFEDLAISASTSLGMGPCHGPEENEYKSEGTF

GIHVAENPSIQLLEGNPGPPADPDGGPRPQADRKFQEREVPCHRPSP

Another preferred adjuvant is the fusion protein LMP1 hIPS1 delta TM (Rev), which contains full length LMP1 from Epstein Barr virus in fusion with amino acids 2-514 human IPS1 sequence (in which the transmembrane domain has been removed) presented in reverse order, i.e., from C terminal to N terminal of the natural sequence. In the fusion protein, the first amino acid (methionine, as encoded by the original direct human DNA) and the TM domain of human IPS1 was removed. The fusion protein is codon optimized for human use. The DNA and encoded amino acid sequences of this fusion protein are shown below:
DNA Sequence (SEQ ID NO: 17)
ATGGATCTGGACCTGGAAAGAGGACCTCCTGGACCTAGACGGCCTCCTAG

AGGACCACCTCTGAGCAGCTCTATTGGACTGGCCCTGCTGCTGCTTCTGC

TGGCTCTGCTGTTCTGGCTGTACATCATCATGAGCAACTGGACCGGCGGA

GCACTGCTGGTGCTGTATGCCTTTGCTCTGATGCTGGTCATCATCATCCT

GATCATCTTCATCTTCCGCGGGACCTGCTGTGTCCTCTGGGAGCACTTTT

GTCTGTTGCTGCTGATGATCACCCTCCTGCTGATCGCCCTGTGGAACCTG

CATGGACAGGCCCTGTATCTGGGAATCGTGCTGTTCATCTTCGGCTGCCT

GCTGGTTCTCGGCCTGTGGATCTACCTGCTGGAAATCCTTTGGAGACTGG

GCGCCACCATCTGGCAGCTGCTGGCCTTTTTCCTGGCCTTCTTTCTGGAT

ATCATCCTCCTCATCATTGCCCTGTACCTGCAGCAGAACTGGTGGACCCT

GCTGGTGGATCTGCTTTGGCTGCTGCTCTTTCTGGCCATCCTGATTTGGA

TGTACTACCACGGCCAGCGGCACAGCGACGAACACCACCATGATGACAGC

CTGCCTCATCCTCAGCAGGCCACCGACGATAGCAGCAACCAGAGCGACAG

CAACAGCAACGAGGGCAGACATCTGCTGCTGGTGTCTGGTGCTGGCGACG

GACCTCCTCTGTGTTCTCAAAATCTTGGCGCCCCTGGCGGCGGACCAAAC

AATGGACCTCAGGACCCCGACAACACCGACGACAATGGCCCTCAAGATCC

TGATAATACCGATGACAACGGCCCACACGACCCTCTGCCTCAAGACCCAG

ATAACACAGACGATAACGGTCCACAAGATCCGGACAATACTGACGATAAT

GGACCCCACGATCCACTGCCTCACAACCCTAGCGATAGCGCCGGAAATGA

TGGCGGACCTCCACAGCTGACCGAGGAAGTGGAAAACAAAGGCGGAGATC

AGGGCCCTCCTCTGATGACCGATGGCGGAGGTGGACACTCTCACGATTCT

GGCCACGACGGCATCGACCCTCATCTGCCTACACTGCTGCTCGGCACATC

TGGCTCTGGCGGCGACGATGATGATCCTCATGGACCTGTGCAGCTGAGCT

ACTACGACCCTTCTCCAAGACACTGCCCAGTGGAAAGAGAGCAGTTCAAG

AGGGACGCCCAGCCTAGACCTGGCGGAGATCCTGATGCTCCACCTGGACC

AAATGGCGAGCTGCTGCAGATCAGCCCTAATGAGGCCGTGCACATCGGCT

TCACCGGCGAGTCTAAGTACGAGAACGAGGAACCCGGCCACTGTCCTGGC

ATGGGCCTTTCTACATCTGCCTCTATCGCCCTGGACGAGTTCTGCGGCAG

CTTTCCATCTGATGTGCAGTCTGCCCTCGTGGGCCCTAAGTCTCTGGAAT

CTGGCCTGGGCAGAAACGAGAGCAGCTCCGATCTGTGGGCTAGCTCTGGT

GGAACAGCTGGCGCTCCTACACCAGCCGCTCCTACCGAAGAGAATAGAAG

CAGCGGCGACACCCCTGTGACAAGCGCCTCTGTGAAAACCCTGGTCATGA

GCACCCCAGTGAAGTCCCCAGTGATGGGCGCCAGAACCTCCAACATTCCC

CTGAAGTCTCCCGCTCCTAACACACTGGCCAACTCTCCAGTGGCTGGCCC

TCCTAAGTCTAGCACCCCTCTGAAAAGCCCCGTGACCTCTGTGTCTGCCC

CTAACGCTCCTGTGAAACTGGCCGTGACCAACGTGCCCATGCTGACCACA

CCTGTGAAATCCCCACTGAGCAATGCCCCTGCCGAGGCCGGAAGCTCTTG

TATCATTCCCGAGGCTCAGGATAGCGAGGCTGGCCAAAAAGGCGAAGCTG

CAGGCGCTTCTGCTCTGGGCCCTAGCTCTAGCTCTTTTAGCACCGGCACC

AGCGTGGTGTCTGGCACACCAGGACCTCTGAGAAGCGCCAGACCTACCTC

TAGAGCCCTGCCTCAGTTTAGCGTGTCCCCTAGTGTGCCTGGCAGAAGCC

CTACACTGTCTAGTACAGCCGGCGCTACACACACCAGCGGACTGGAAACA

GACCAAGAACAGCATGGCAGCAGCACCCTGCCTTCTCTGGCTGCCCTTGA

TTCTAGCAGCGAACTGCCAGGCGGCGACCCCAATAGACCTATCGCTAGAC

CTAGCCTGACACAGCTGGCCCAAGAGAGCAATGAGGGCCCTTCTGAGCCT

GCTCAGACCGAACAGGTGCCAATGCCTTACAGCCCCGAGAAAGAGCGGTG

CAGCAACTACCCTATCAGCCATGCCGCTGCTCCCACACCTCCTGGTCCAA

GAGAAGCTCCTCTGAGCCCTCCTGAGCTGCCCGATCCTCCAAGAGATAGC

ACCAGACCTCAGTACTCCCAGTACGTGTCCGCCGTGGAAGATGCCCTGGA

TGTGCTGGAATGTGGCAGACTGGCCGCCATCTTCTACGAAGTGTGGGGCC

CTAGAAGGCAGCTGACCAACTTTCTGCACTGGCTGACCGACAGAAACGGC

AGCCTGACATGTACCGCCAGACTGAGAGATCAGGACCGGGCCACACTGTG

CCCTCTGTATCCTCTGATCGAGGTGGTGGACGTGAACTGCTTCAACAGCT

TCAACCGGTGCATCTACAAGTACACCAAGGACGAGGCTTTCCCTATG

Protein Sequence (SEQ ID NO: 18)
MDLDLERGPPGPRRPPRGPPLSSSIGLALLLLLLALLFWLYIIMSNWTGG

ALLVLYAFALMLVIIILIIFIFRRDLLCPLGALCLLLLMITLLLIALWNL

HGQALYLGIVLFIFGCLLVLGLWIYLLEILWRLGATIWQLLAFFLAFFLD

IILLIIALYLQQNWWTLLVDLLWLLLFLAILIWMYYHGQRHSDEHHHDDS

LPHPQQATDDSSNQSDSNSNEGRHLLLVSGAGDGPPLCSQNLGAPGGGPN

NGPQDPDNTDDNGPQDPDNTDDNGPHDPLPQDPDNTDDNGPQDPDNTDDN

GPHDPLPHNPSDSAGNDGGPPQLTEEVENKGGDQGPPLMTDGGGGHSHDS

GHDGIDPHLPTLLLGTSGSGGDDDDPHGPVQLSYYDPSPRHCPVEREQFK
RDAQPRPGGDPDAPPGPNGELLQISPNEAVHIGFTGESKYENEEPGHCPG
MGLSTSASIALDEFCGSFPSDVQSALVGPKSLESGLGRNESSSDLWASSG
GTAGAPTPAAPTEENRSSGDTPVTSASVKTLVMSTPVKSPVMGARTSNIP
LKSPAPNTLANSPVAGPPKSSTPLKSPVTSVSAPNAPVKLAVTNVPMLTT
PVKSPLSNAPAEAGSSCIIPEAQDSEAGQKGEAAGASALGPSSSSFSTGT
SVVSGTPGPLRSARPTSRALPQFSVSPSVPGRSPTLSSTAGATHTSGLET
DQEQHGSSTLPSLAALDSSSELPGGDPNRPIARPSLTQLAQESNEG**PSEP
AQTEQVPMPYSPEKERCSNYPISHAAAPTPPGPREAPLSPPELPDPP**RDS
TRPQYSQYVSAVEDALDVLECGRLAAIFYEVWGPRRQLTNFLHWLTDRNG
SLTCTARLRDQDRATLCPLYPLIEVVDVNCFNSFNRCIYKYTKDEAFPM

The bolded portion of SEQ ID NOS:17 & 18 represents the proline-rich domain.

Another preferred adjuvant is the fusion protein LMP1 (delta IC) hIPS1 (delta TM) LMP1 (cyt), which contains a truncated LMP1 sequence (lacking the intra-cytoplasmic domain) in fusion with human IPS1 lacking the transmembrane domain, in turn fused to the LMP1 intra-cytoplasmic domain. In the fusion protein, the first amino acid (methionine) of human IPS1 was removed. The fusion protein is codon optimized for human use. The DNA and encoded amino acid sequences of this fusion protein are shown below:

DNA Sequence (SEQ ID NO: 19)
ATGGATCTGGATCTCGAAAGAGGACCTCCTGGACCTAGACGGCCTCCTAG
AGGACCACCTCTGAGCAGCTCTATTGGACTGGCCCTGCTGCTGCTTCTGC
TGGCTCTGCTGTTCTGGCTGTACATCATCATGAGCAACTGGACCGGCGGA
GCACTGCTGGTGCTGTATGCCTTTGCTCTGATGCTGGTCATCATCATCCT
GATCATCTTCATCTTCCGGCGGGACCTGCTGTGTCCTCTGGGAGCACTTT
GTCTGTTGCTGCTGATGATCACCCTCCTGCTGATCGCCCTGTGGAACCTG
CATGGACAGGCCCTGTATCTGGGCATCGTGCTGTTCATCTTCGGCTGCCT
GCTGGTTCTCGGCCTGTGGATCTACCTGCTGGAAATCCTTTGGAGACTGG
GCGCCACCATCTGGCAGCTGCTGGCCTTTTTCCTGGCCTTCTTTCTGGAT
ATCATCCTCCTCATCATTGCCCTGTACCTGCAGCAGAACTGGTGGACCCT
GCTGGTGGATCTGCTTTGGCTGCTGCTCTTTCTGGCCATCCTGATTTGGA
TGTACTACCACGGCCAGCGGCCTTTCGCCGAGGACAAGACCTACAAGTAC
ATCTGCCGGAACTTCAGCAACTTCTGCAACGTGGACGTGGTGGAAATTCT
GCCCTACCTGCCTTGCCTGACCGCCAGAGATCAGGACAGACTGAGAGCCA
CATGTACCCTGAGCGGCAACAGAGACACACTGTGGCACCTGTTCAACACC
CTGCAGAGAAGGCCTGGCTGGGTCGAGTACTTTATCGCCGCTCTGAGAGG
CTGCGAGCTGGTCGATCTGGCTGATGAAGTGGCCAGCGTGTACCAGAGCT
ACCAGCCTAGAACCAGCGACCGGC**TCCTGATCCTCTCGAACCTCCATCT
CTGCCCGCCGAAAGACCTGGACCTCCTACACCAGCTGCCGCTCACAGCAT
CCCTTACAACAGCTGCAGAGAGAAAGAACCTAGCTACCCCATGCCTGTGC
AAGAGACACAGGCCCCAGAAAGCCCT**GGCGAGAATAGCGAACAGGCTCTG
CAGACACTGAGCCCCAGAGCCATTCCTAGAAACCCTGATGGCGGCCCTCT
GGAAAGCTCTAGTGATCTGGCCGCTCTGTCCCCTCTGACAAGCTCTGGAC
ACCAAGAGCAGGATACCGAGCTGGGCAGCACACATACAGCCGGCGCTACA
AGCAGCCTGACACCTTCTAGAGGCCCCGTGTCTCCCAGCGTGTCATTTCA
GCCTCTGGCCAGGTCTACCCCTAGGGCTTCTAGACTGCCTGGACCAACAG
GCAGCGTGGTGTCTACCGGCACAAGCTTCAGCTCTAGCTCTCCTGGACTG
GCTAGTGCCGGTGCCGCTGAGGGAAAACAAGGCGCCGAATCTGATCAGGC
CGAGCCTATCATCTGTAGCAGCGGAGCAGAAGCCCCTGCCAATAGCCTGC
CTAGCAAGGTGCCAACCACACTGATGCCCGTGAACACAGTGGCCCTGAAG
GTGCCAGCTAATCCTGCCTCCGTGTCCACCGTGCCTTCTAAGCTGCCAAC
CAGCTCTAAGCCACCTGGCGCCGTGCCATCTAACGCCCTGACAAATCCTG
CTCCAAGCAAGCTGCCCATCAACTCCACAAGAGCCGGCATGGTGCCCTCT
AAGGTGCCCACATCTATGGTGCTGACCAAGGTGTCCGCCAGCACCGTGCC
AACAGATGGCAGCTCCAGAAACGAGGAAACCCCTGCCGCTCCTACTCCTG
CTGGCGCTACAGGCGGATCTTCTGCTTGGCTGGATAGCAGCAGCGAGAAC
AGAGGCCTGGGCAGCGAGCTTTCTAAACCTGGCGTGCTGGCTTCCCAGGT
GGACAGCCCATTTTCCGGCTGCTTTGAGGACCTGGCTATCAGCGCCTCTA
CAAGCCTCGGCATGGGACCTTGTCACGGCCCCGAGGAAAACGAGTACAAG
AGCGAGGGCACCTTCGGCATCCACGTGGCCGAGAATCCTAGCATCCAACT
GCTGGAAGGCAACCCCGGACCTCCAGCTGATCCAGATGGCGGACCAAGAC
CTCAGGCCGACAGAAAGTTCCAAGAGCGCGAGGTGCCCTGCCACAGACCT
TCTCCACACAGCGACGAACACCACCATGATGACAGCCTGCCTCATCCTCA
GCAGGCCACCGACGATAGCAGCAACCAGAGCGACAGCAACAGCAACGAGG
GCAGACATCTGCTGCTGGTGTCTGGTGCTGGCGACGGACCTCCTCTGTGT
TCTCAAAATCTTGGCGCCCCTGGCGGCGGACCAAACAATGGACCTCAGGA
CCCCGACAACACCGACGACAATGGCCCTCAAGATCCTGATAATACCGATG
ACAACGGCCCACACGACCCTCTGCCTCAAGACCCAGATAACACAGACGAT
AACGGTCCACAAGATCCGGACAATACTGACGATAATGGACCCCACGATCC
ACTGCCTCACAACCCTAGCGATAGCGCCGGAAATGATGGCGGACCTCCAC
AGCTGACCGAGGAAGTGGAAAACAAAGGCGGAGATCAGGGCCCTCCTCTG
ATGACCGATGGCGGAGGTGGACACTCTCACGATTCTGGCCACGACGGCAT
CGACCCTCATCTGCCTACACTGCTGCTCGGCACATCTGGCTCTGGCGGCG
ACGATGATGATCCTCATGGACCTGTGCAGCTGAGCTACTACGAC Protein Sequence (SEQ ID NO: 20)
MDLDLERGPPGPRRPPRGPPLSSSIGLALLLLLLALLFWLYIIMSNWTGG
ALLVLYAFALMLVIILIIFIFRRDLLCPLGALCLLLLMITLLLIALWNL
HGQALYLGIVLFIFGCLLVLGLWIYLLEILWRLGATIWQLLAFFLAFFLD -continued
IILLIIALYLQQNWWTLLVDLLWLLLFLAILIWMYYHGQRPFAEDKTYKY

ICRNFSNFCNVDVVEILPYLPCLTARDQDRLRATCTLSGNRDTLWHLFNT

LQRRPGWVEYFIAALRGCELVDLADEVASVYQSYQPRTSDRPPDPLEPPS

LPAERPGPPTPAAAHSIPYNSCREKEPSYPMPVQETQAPESPGENSEQAL

QTLSPRAIPRNPDGGPLESSSDLAALSPLTSSGHQEQDTELGSTHTAGAT

SSLTPSRGPVSPSVSFQPLARSTPRASRLPGPTGSVVSTGTSFSSSSPGL

ASAGAAEGKQGAESDQAEPTICSSGAEAPANSLPSKVPTTLMPVNTVALK

VPANPASVSTVPSKLPTSSKPPGAVPSNALTNPAPSKLPINSTRAGMVPS

KVPTSMVLTKVSASTVPTDGSSRNEETPAAPTPAGATGGSSAWLDSSSEN

RGLGSELSKPGVLASQVDSPFSGCFEDLAISASTSLGMGPCHGPEENEYK

SEGTFGIHVAENPSIQLLEGNPGPPADPDGGPRPQADRKFQEREVPCHRP

SPHSDEHHHDDSLPHPQQATDDSSNQSDSNSNEGRHLLLVSGAGDGPPLC

SQNLGAPGGGPNNGPQDPDNTDDNGPQDPDNTDDNGPHDPLPQDPDNTDD

NGPQDPDNTDDNGPHDPLPHNPSDSAGNDGGPPQLTEEVENKGGDQGPPL

MTDGGGGHSHDSGHDGIDPHLPTLLLGTSGSGGDDDDPHGPVQLSYYD

The bolded portion of SEQ ID NOS:19 & 20 represents the proline-rich domain.

Another preferred adjuvant is the fusion protein LMP1 (delta IC) hIPS1 (delta TM Pro) LMP1 (cyt), which contains a truncated LMP1 sequence (lacking the intra-cytoplasmic domain) in fusion with human IPS1 lacking the transmembrane domain and proline-rich domain, in turn fused to the LMP1 intra-cytoplasmic domain. In the fusion protein, the first amino acid (methionine) of human IPS1 was removed. The fusion protein is codon optimized for human use. The DNA and encoded amino acid sequences of this fusion protein are shown below:

DNA Sequence (SEQ ID NO: 21)
ATGGATCTGGATCTCGAAAGAGGACCTCCTGGACCTAGACGGCCTCCTAG

AGGACCACCTCTGAGCAGCTCTATTGGACTGGCCCTGCTGCTGCTTCTGC

TGGCTCTGCTGTTCTGGCTGTACATCATCATGAGCAACTGGACCGGCGGA

GCACTGCTGGTGCTGTATGCCTTTGCTCTGATGCTGGTCATCATCATCCT

GATCATCTTCATCTTCCGGCGGGACCTGCTGTGTCCTCTGGGAGCACTTT

GTCTGTTGCTGCTGATGATCACCCTCCTGCTGATCGCCCTGTGGAACCTG

CATGGACAGGCCCTGTATCTGGGCATCGTGCTGTTCATCTTCGGCTGCCT

GCTGGTTCTCGGCCTGTGGATCTACCTGCTGGAAATCCTTTGGAGACTGG

GCGCCACCATCTGGCAGCTGCTGGCCTTTTTCCTGGCCTTCTTTCTGGAT

ATCATCCTCCTCATCATTGCCCTGTACCTGCAGCAGAACTGGTGGACCCT

GCTGGTGGATCTGCTTTGGCTGCTGCTCTTTCTGGCCATCCTGATTTGGA

TGTACTACCACGGCCAGCGGCCTTTCGCCGAGGACAAGACCTACAAGTAC

ATCTGCCGGAACTTCAGCAACTTCTGCAACGTGGACGTGGTGGAAATTCT

GCCCTACCTGCCTTGCCTGACCGCCAGAGATCAGGACAGACTGAGAGCCA

CATGTACCCTGAGCGGCAACAGAGACACACTGTGGCACCTGTTCAACACC

CTGCAGAGAAGGCCTGGCTGGGTCGAGTACTTTATCGCCGCTCTGAGAGG

-continued
CTGCGAGCTGGTCGATCTGGCTGATGAAGTGGCCAGCGTGTACCAGAGCT

ACCAGCCTAGAACCAGCGACCGGGGCGAGAATAGCGAACAGGCTCTGCAG

ACACTGAGCCCCAGAGCCATTCCTAGAAACCCTGATGGCGGCCCTCTGGA

AAGCTCTAGTGATCTGGCCGCTCTGTCCCTCTGACAAGCTCTGGACACC

AAGAGCAGGATACCGAGCTGGGCAGCACACATACAGCCGGCGCTACAAGC

AGCCTGACACCTTCTAGAGGCCCCGTGTCTCCCAGCGTGTCATTTCAGCC

TCTGGCCAGGTCTACCCCTAGGGCTTCTAGACTGCCTGGACCAACAGGCA

GCGTGGTGTCTACCGGCACAAGCTTCAGCTCTAGCTCTCCTGGACTGGCT

AGTGCCGGTGCCGCTGAGGGAAAACAAGGCGCCGAATCTGATCAGGCCGA

GCCTATCATCTGTAGCAGCGGAGCAGAAGCCCCTGCCAATAGCCTGCCTA

GCAAGGTGCCAACCACACTGATGCCCGTGAACACAGTGGCCCTGAAGGTG

CCAGCTAATCCTGCCTCCGTGTCCACCGTGCCTTCTAAGCTGCCAACCAG

CTCTAAGCCACCTGGCGCCGTGCCATCTAACGCCCTGACAAATCCTGCTC

CAAGCAAGCTGCCCATCAACTCCACAAGAGCCGGCATGGTGCCCTCTAAG

GTGCCCACATCTATGGTGCTGACCAAGGTGTCCGCCAGCACCGTGCCAAC

AGATGGCAGCTCCAGAAACGAGGAAACCCCTGCCGCTCCTACTCCTGCTG

GCGCTACAGGCGGATCTTCTGCTTGGCTGGATAGCAGCAGCGAGAACAGA

GGCCTGGGCAGCGAGCTTTCTAAACCTGGCGTGCTGGCTTCCCAGGTGGA

CAGCCCATTTTCCGGCTGCTTTGAGGACCTGGCTATCAGCGCCTCTACAA

GCCTCGGCATGGGACCTTGTCACGGCCCCGAGGAAAACGAGTACAAGAGC

GAGGGCACCTTCGGCATCCACGTGGCCGAGAATCCTAGCATCCAACTGCT

GGAAGGCAACCCCGGACCTCCAGCTGATCCAGATGGCGGACCAAGACCTC

AGGCCGACAGAAAGTTCCAAGAGCGCGAGGTGCCCTGCCACAGACCTTCT

CCACACAGCGACGAACACCACCATGATGACAGCCTGCCTCATCCTCAGCA

GGCCACCGACGATAGCAGCAACCAGAGCGACAGCAACAGCAACGAGGGCA

GACATCTGCTGCTGGTGTCTGGTGCTGGCGACGGACCTCCTCTGTGTTCT

CAAAATCTTGGCGCCCCTGGCGGCGGACCAAACAATGGACCTCAGGACCC

CGACAACACCGACGACAATGGCCCTCAAGATCCTGATAATACCGATGACA

ACGGCCCACACGACCCTCTGCCTCAAGACCCAGATAACACAGACGATAAC

GGTCCACAAGATCCGGACAATACTGACGATAATGGACCCCACGATCCACT

GCCTCACAACCCTAGCGATAGCGCCGGAAATGATGGCGGACCTCCACAGC

TGACCGAGGAAGTGGAAAACAAAGGCGGAGATCAGGGCCCTCCTCTGATG

ACCGATGGCGGAGGTGGACACTCTCACGATTCTGGCCACGACGGCATCGA

CCCTCATCTGCCTACACTGCTGCTCGGCACATCTGGCTCTGGCGGCGACG

ATGATGATCCTCATGGACCTGTGCAGCTGAGCTACTACGAC

Protein Sequence (SEQ ID NO: 22)
MDLDLERGPPGPRRPPRGPPLSSSIGLALLLLLLALLFWLYIIMSNWTGG

ALLVLYAFALMLVIIILIIFIFRRDLLCPLGALCLLLLMITLLLIALWNL

HGQALYLGIVLFIFGCLLVLGLWIYLLEILWRLGATIWQLLAFFLAFFLD

-continued

IILLIIALYLQQNWWTLLVDLLWLLLFLAILIWMYYHGQRPFAEDKTYKY

ICRNFSNFCNVDVVEILPYLPCLTARDQDRLRATCTLSGNRDTLWHLFNT

LQRRPGWVEYFIAALRGCELVDLADEVASVYQSYQPRTSDRGENSEQALQ

TLSPRAIPRNPDGGPLESSSDLAALSPLTSSGHQEQDTELGSTHTAGATS

SLTPSRGPVSPSVSFQPLARSTPRASRLPGPTGSVVSTGTSFSSSSPGLA

SAGAAEGKQGAESDQAEPIICSSGAEAPANSLPSKVPTTLMPVNTVALKV

PANPASVSTVPSKLPTSSKPPGAVPSNALTNPAPSKLPINSTRAGMVPSK

VPTSMVLTKVSASTVPTDGSSRNEETPAAPTPAGATGGSSAWLDSSSENR

GLGSELSKPGVLASQVDSPFSGCFEDLAISASTSLGMGPCHGPEENEYKS

EGTFGIHVAENPSIQLLEGNPGPPADPDGGPRPQADRKFQEREVPCHRPS

PHSDEHHHDDSLPHPQQATDDSSNQSDSNSNEGRHLLLVSGAGDGPPLCS

QNLGAPGGGPNNGPQDPDNTDDNGPQDPDNTDDNGPHDPLPQDPDNTDDN

GPQDPDNTDDNGPHDPLPHNPSDSAGNDGGPPQLTEEVENKGGDQGPPLM

TDGGGGHSHDSGHDGIDPHLPTLLLGTSGSGGDDDDPHGPVQLSYYD

Another preferred adjuvant is the fusion protein LMP1 (delta IC) hIPS1 (delta TM Rev) LMP1 (cyt), which contains a truncated LMP1 sequence (lacking the intra-cytoplasmic domain) in fusion with human IPS1 sequence presented in reverse order, i.e., from C terminal to N terminal of the natural sequence, without the TM domain) in turn fused to the LMP1 intra-cytoplasmic domain. In the fusion protein, the first amino acid (methionine) of human IPS1 was removed. The fusion protein is codon optimized for human use. The DNA and encoded amino acid sequences of this fusion protein are shown below:

DNA Sequence (SEQ ID NO: 23)
ATGGATCTGGATCTCGAAAGAGGACCTCCTGGACCTAGACGGCCTCCTAG

AGGACCACCTCTGAGCAGCTCTATTGGACTGGCCCTGCTGCTGCTTCTGC

TGGCTCTGCTGTTCTGGCTGTACATCATCATGAGCAACTGGACCGGCGGA

GCACTGCTGGTGCTGTATGCCTTTGCTCTGATGCTGGTCATCATCATCCT

GATCATCTTCATCTTCCGGCGGGACCTGCTGTGTCCTCTGGGAGCACTTT

GTCTGTTGCTGCTGATGATCACCCTCCTGCTGATCGCCCTGTGGAACCTG

CATGGACAGGCCCTGTATCTGGGCATCGTGCTGTTCATCTTCGGCTGCCT

GCTGGTTCTCGGCCTGTGGATCTACCTGCTGGAAATCCTTTGGAGACTGG

GCGCCACCATCTGGCAGCTGCTGGCCTTTTTCCTGGCCTTCTTTCTGGAT

ATCATCCTCCTCATCATTGCCCTGTACCTGCAGCAGAACTGGTGGACCCT

GCTGGTGGATCTGCTTTGGCTGCTGCTCTTTCTGGCCATCCTGATTTGGA

TGTACTACCACGGCCAGCGGCCTTCTCCAAGACACTGCCCAGTGGAAAGA

GAGCAGTTCAAGAGGGACGCCCAGCCTAGACCTGGCGGAGATCCTGATGC

TCCACCTGGACCAAATGGCGAGCTGCTGCAGATCAGCCCTAATGAGGCCG

TGCACATCGGCTTCACCGGCGAGTCTAAGTACGAGAACGAGGAACCCGGC

CACTGTCCTGGCATGGGCCTTTCTACATCTGCCTCTATCGCCCTGGACGA

GTTCTGCGGCAGCTTTCCATCTGATGTGCAGTCTGCCCTCGTGGGCCCTA

AGTCTCTGGAATCTGGCCTGGGCAGAAACGAGAGCAGCTCCGATCTGTGG

GCTAGCTCTGGTGGAACAGCTGGCGCTCCTACACCAGCCGCTCCTACCGA

AGAGAATAGAAGCAGCGGCGACACCCCTGTGACAAGCGCCTCTGTGAAAA

CCCTGGTCATGAGCACCCCAGTGAAGTCCCCAGTGATGGGCGCCAGAACC

TCCAACATTCCCCTGAAGTCTCCCGCTCCTAACACACTGGCCAACTCTCC

AGTGGCTGGCCCTCCTAAGTCTAGCACCCCTCTGAAAAGCCCCGTGACCT

CTGTGTCTGCCCCTAACGCTCCTGTGAAACTGGCCGTGACCAACGTGCCC

ATGCTGACCACACCTGTGAAATCCCCACTGAGCAATGCCCCTGCCGAGGC

CGGAAGCTCTTGTATCATTCCCGAGGCTCAGGATAGCGAGGCTGGCCAAA

AAGGCGAAGCTGCAGGCGCTTCTGCTCTGGGCCCTAGCTCTAGCTCTTTT

AGCACCGGCACCAGCGTGGTGTCTGGCACACCAGGACCTCTGAGAAGCGC

CAGACCTACCTCTAGAGCCCTGCCTCAGTTTAGCGTGTCCCCTAGTGTGC

CTGGCAGAAGCCCTACACTGTCTAGTACAGCCGGCGCTACACACACCAGC

GGACTGGAAACAGACCAAGAACAGCATGGCAGCAGCACCCTGCCTTCTCT

GGCTGCCCTTGATTCTAGCAGCGAACTGCCAGGCGGCGACCCCAATAGAC

CTATCGCTAGACCTAGCCTGACACAGCTGGCCCAAGAGAGCAATGAGGGC

CCTTCTGAGCCTGCTCAGACCGAACAGGTGCCAATGCCTTACAGCCCCGA

GAAAGAGCGGTGCAGCAACTACCCTATCAGCCATGCCGCTGCTCCCACAC

CTCCTGGTCCAAGAGAAGCTCCTCTGAGCCCTCCTGAGCTGCCCGATCCT

CCAAGAGATAGCACCAGACCTCAGTACTCCCAGTACGTGTCCGCCGTGGA

AGATGCCCTGGATGTGCTGGAATGTGGCAGACTGGCCGCCATCTTCTACG

AAGTGTGGGGCCCTAGAAGGCAGCTGACCAACTTTCTGCACTGGCTGACC

GACAGAAACGGCAGCCTGACATGTACCGCCAGACTGAGAGATCAGGACCG

GGCCACACTGTGCCCTCTGTATCCTCTGATCGAGGTGGTGGACGTGAACT

GCTTCAACAGCTTCAACCGGTGCATCTACAAGTACACCAAGGACGAGGCT

TTCCCTATGCACAGCGACGAACACCACCATGATGACAGCCTGCCTCATCC

TCAGCAGGCCACCGACGATAGCAGCAACCAGAGCGACAGCAACAGCAACG

AGGGCAGACATCTGCTGCTGGTGTCTGGTGCTGGCGACGGACCTCCTCTG

TGTTCTCAAAATCTTGGCGCCCCTGGCGGCGGACCAAACAATGGACCTCA

GGACCCCGACAACACCGACGACAATGGCCCTCAAGATCCTGATAATACCG

ATGACAACGGCCCACACGACCCTCTGCCTCAAGACCCAGATAACACAGAC

GATAACGGTCCACAAGATCCGGACAATACTGACGATAATGGACCCCACGA

TCCACTGCCTCACAACCCTAGCGATAGCGCCGGAAATGATGGCGGACCTC

CACAGCTGACCGAGGAAGTGGAAAACAAAGGCGGAGATCAGGGCCCTCCT

CTGATGACCGATGGCGGAGGTGGACACTCTCACGATTCTGGCCACGACGG

CATCGACCCTCATCTGCCTACACTGCTGCTCGGCACATCTGGCTCTGGCG

GCGACGATGATGATCCTCATGGACCTGTGCAGCTGAGCTACTACGAC

Protein Sequence (SEQ ID NO: 24)
MDLDLERGPPGPRRPPRGPPLSSSIGLALLLLLLALLFWLYIIMSNWTGG

ALLVLYAFALMLVIIILIIFIFRRDLLCPLGALCLLLLMITLLLIALWNL

HGQALYLGIVLFIFGCLLVLGLWIYLLEILWRLGATIWQLLAFFLAFFLD

IILLIIALYLQQNWWTLLVDLLWLLLFLAILIWMYYHGQRPSPRHCPVER

EQFKRDAQPRPGGDPDAPPGPNGELLQISPNEAVHIGFTGESKYENEEPG

HCPGMGLSTSASIALDEFCGSFPSDVQSALVGPKSLESGLGRNESSSDLW

ASSGGTAGAPTPAAPTEENRSSGDTPVTSASVKTLVMSTPVKSPVMGART

SNIPLKSPAPNTLANSPVAGPPKSSTPLKSPVTSVSAPNAPVKLAVTNVP

MLTTPVKSPLSNAPAEAGSSCIIPEAQDSEAGQKGEAAGASALGPSSSSF

STGTSVVSGTPGPLRSARPTSRALPQFSVSPSVPGRSPTLSSTAGATHTS

GLETDQEQHGSSTLPSLAALDSSSELPGGDPNRPIARPSLTQLAQESNEG

PSEPAQTEQVPMPYSPEKERCSNYPISHAAAPTPPGPREAPLSPPELPDP

PRDSTRPQYSQYVSAVEDALDVLECGRLAAIFYEVWGPRRQLTNFLHWLT

DRNGSLTCTARLRDQDRATLCPLYPLIEVVDVNCFNSFNRCIYKYTKDEA

FPMHSDEHHHDDSLPHPQQATDDSSNQSDSNSNEGRHLLLVSGAGDGPPL

CSQNLGAPGGGPNNGPQDPDNTDDNGPQDPDNTDDNGPHDPLPQDPDNTD

DNGPQDPDNTDDNGPHDPLPHNPSDSAGNDGGPPQLTEEVENKGGDQGPP

LMTDGGGGHSHDSGHDGIDPHLPTLLLGTSGSGGDDDDPHGPVQLSYYD

The bolded portion of SEQ ID NOS:23 & 24 represents the proline-rich domain.

In preferred embodiments, an immune checkpoint inhibitor molecule or a soluble immune modulator molecule will be encoded within the viral vector, enhancing the immune response against a tumor. The immune checkpoint inhibitor molecule can be, but is not limited to, an anti-CTLA-4 molecule, a PD1 blocker, and a PDL1 blocker. The immune checkpoint inhibitor molecule can be a protein, such as an antibody, or a soluble form of an anticheckpoint.

In certain embodiments, the viral vector may include more than one expression cassette. In some embodiments, the viral vector particles may include more than one nucleic acid molecule, such as two or three nucleic acid molecules, which may be delivered separately or operatively linked. In some embodiments, the second nucleic acid encodes an antigen and/or soluble immune checkpoint inhibitor molecule or a soluble immune modulator molecule. In some embodiments, the third nucleic acid encodes an antigen and/or immune checkpoint inhibitor molecule different from that encoded by the second nucleic acid molecule.

In one aspect, the technology is an immunotherapeutic formulation for preventing or treating a disease or condition in a subject. The vaccine includes a therapeutically effective amount of the viral vector. The disease may be any disease in which vaccination against an agent is desirable, such as cancer or an infection.

In another aspect, the present technology is a method for inducing or enhancing an immune response against cancer or infection in a subject. The method includes administering a therapeutically effective amount of the viral vector or immunotherapeutic formulation to a subject in need thereof.

EXAMPLES

Example 1. Molecular Constructs

According to the bimolecular adjuvant strategy, vectors were constructed containing the following elements: (a) a promoter, preferably a human ubiquitin promoter; (b) a reporter gene (e.g., green fluorescent protein) or, alternatively, one or more antigens in fusion in a single transgene; (c) an IRES followed by a first adjuvant gene (i.e., LMP1 or LMP1 CO); (d) an IRES followed by the second adjuvant gene (i.e., LMP1-IPS1 fusion protein); and (e) optionally, an IRES followed by one or more genes encoding a soluble and secreted immune checkpoint inhibitor or a soluble immune modulator molecule (see, e.g., FIGS. 8A-8C). In general, the sequences are preferably in the aforementioned order (in particular, the order of (c) and (d) can be reversed), but the genes can be situated in the vector in any other suitable order. Control vectors were also constructed that had some, but not all the above mentioned regions.

According to the single molecular adjuvant strategy, vectors were constructed containing the following elements: (a) a promoter, preferably a human ubiquitin promoter; (b) a reporter gene (e.g., green fluorescent protein) or, alternatively, one or more antigens in fusion in a single transgene; (c) an IRES followed by an adjuvant fusion protein gene (i.e., LMP1 devoid of its intra-cytoplasmic signaling domain fused to the LMP1 intra-cytoplasmic signaling domain fused to hIPS1 or a functional equivalent thereof (e.g. hIPS1 delta TM), or LMP1 lacking its intra-cytoplasmic domain fused to hIPS1 or a functional equivalent thereof that is in turn fused to the intra-cytoplasmic signaling domain of LMP1; and (d) optionally, an IRES followed by one or more genes encoding a soluble and secreted immune checkpoint inhibitor or a soluble immune modulator molecule (see, e/g/, FIGS. 8A-8C). Generally, the sequences are preferably in the aforementioned order, but the genes can be situated in the vector in any other suitable order. Control vectors are also constructed that have some, but not all the above mentioned regions.

Example 2. Production of Viral Vectors

Lentiviral vectors were produced by transient calcium-phosphate transfection of HEK 293T cells Line as described in Nasri et al. (2014). HEK 293T cells were seeded at $1.6 \times 10^8$ cells in a two chambers Cell Stack (Corning) in 250 mL of complete culture medium and maintained 24 h in an incubator with humidified atmosphere of 5% $CO_2$ at 37° C. to adhere. For each vector produced, one cell stack was transfected as follows. The lentiviral backbone plasmid (235 µg), the envelope coding plasmid (47 µg), and the packaging plasmid (235 µg) were mixed with 8.6 mL of sterile distilled water and 3.0 mL of $CaCl_2$. The DNA mix was then added drop by drop to 12.1 mL of 37° C. pre-warmed HBS 2×, pH=7.1, and the 24.2 mL of precipitate obtained were added to the culture medium of the cells after 30 minutes of incubation at room temperature. The transfected cells were incubated at 37° C., 5% $CO_2$. The medium was replaced 24 h after transfection by 210 mL of harvest medium without serum and phenol red, and the viral supernatant was harvested after an additional 24 h, clarified by centrifugation for 5 min at 2500 rpm. The harvest clarified bulk (210 mL) was treated 30 min with DNase I in the presence of $MgCl_2$ to cleave any residual DNA, and concentrated by centrifugation 1 h at 22000 rpm, 4° C. Vector pellets were resuspended in 70 μl of Tris-Trehalose (50 mM), pooled in a 1.5 mL microtube and divided into 50 μL aliquots, frozen and stored at ≤−70° C.

Production yields were a bit less effective with adjuvanted vectors compared to GFP vector, certainly due to the presence of longer DNA cassette. However, for all adjuvanted constructions titers were at least in the $10^9$ TU/mL range and were consistently found among different production campaigns. No issue that would impact industrial bioproduction was observed.

Example 3. In Vitro Effects of Double Adjuvanted Lentiviral Vectors Activating Both CD40L and STING Pathways Fresh human dendritic cells and macrophages were obtained from healthy human donors (leukocyte cones) over a density gradient. CD14-positive monocytes were purified from PBMC using a magnetic isolation kit (positive selection) and were plated in 6-well plates in complete RPMI. Monocytes were differentiated into DCs with GM-CSF and IL-4 using published methods. A 10% media change was made after 3 days to replenish cytokines and cells were harvested after a total of 6 days of culture using non-enzymatic cell dissociation solution. DCs were then re-plated in complete RPMI+4 μg/ml of polybrene+lentiviral construct (at an MOI of 15)+GM-CSF and IL-4. After 2 hours, 700 μl of complete RPMI+GM-CSF/IL-4 was added, and cells were cultured for 96 hours in total. Additional control wells were stimulated with IFN-γ and LPS for 96 hours, to act as a positive control for activation marker expression.

CD14+ monocytes were differentiated into M1 or M2 macrophages with GM-CSF (M1) or M-CSF (M2). A 10% media change was made after 3 days to replenish cytokines and cells were harvested after a total of 6 days of culture using non-enzymatic cell dissociation solution, and macrophages were pooled at a 1:1 ratio. M1/M2 macrophages were then re-plated in 300 μl of complete RPMI+4 μg/ml of polybrene+lentiviral construct (at an MOI of 15)+M-CSF). After 2 hours, 700 μl of complete RPMI+M-CSF was added, and cells were cultured for 96 hours in total. Additional control wells were stimulated with IFN-gamma and LPS (M1) or IL-13 and IL-4 (M2) for 96 hours in total, to act as a positive control for activation marker expression.

Human DCs and macrophages were transduced with a MOI of 15 with lentiviral vectors containing expression cassettes as described below:

Construct 1: GFP-IRES-LMP1(dIC)-IPS1(dTM)-LMP1(IC)
Construct 2: GFP-IRES-LMP1(dIC)-IPS1(dTMdPro)-LMP1(IC)
Construct 3: GFP-IRES-LMP1(dIC)-IPS1(dTMRev)-LMP1(IC)
Construct 4: GFP-IRES-LMP1-IPS1(dTM)
Construct 5: GFP-IRES-LMP1-IPS1(dTMdPro)
Construct 6: GFP-IRES-LMP1-IPS1(dTMRev)
Control Construct 1: GFP
Control Construct 2: GFP-IRES-LMP1(dIC)

Figure 8A:
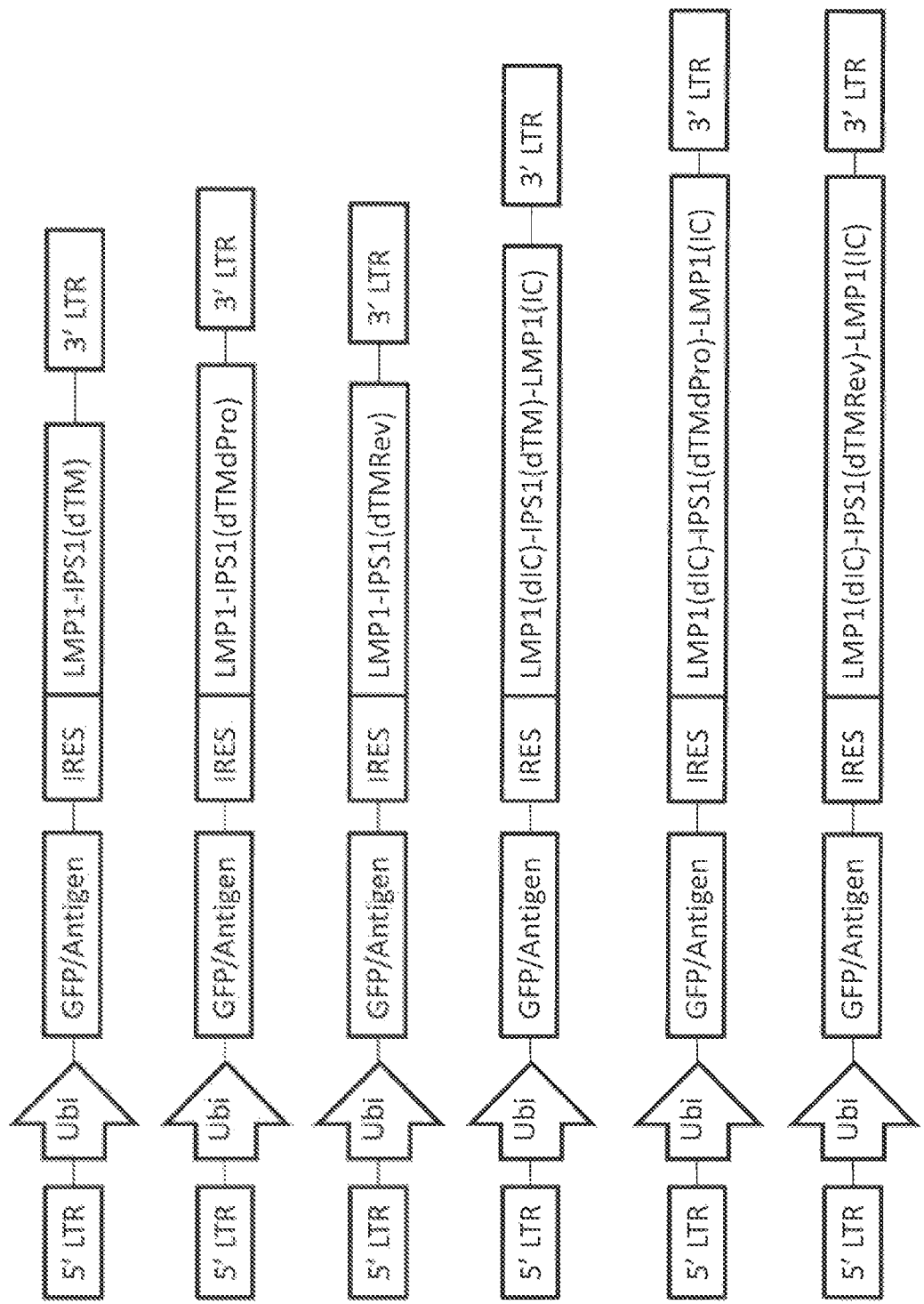
FIGS. 8A-8B show schematic representations of several molecular constructs.
Figure 8B:
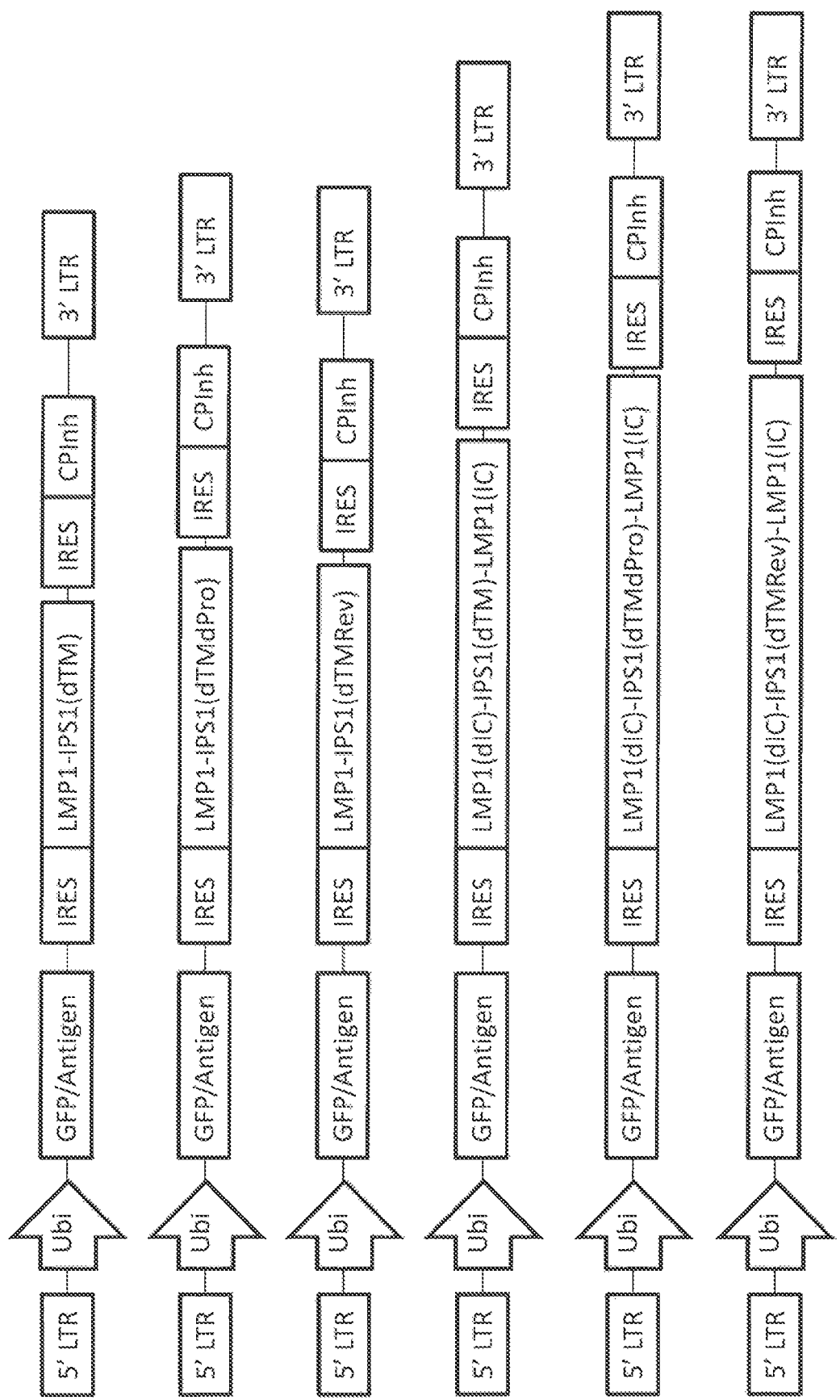
Figure 9B:
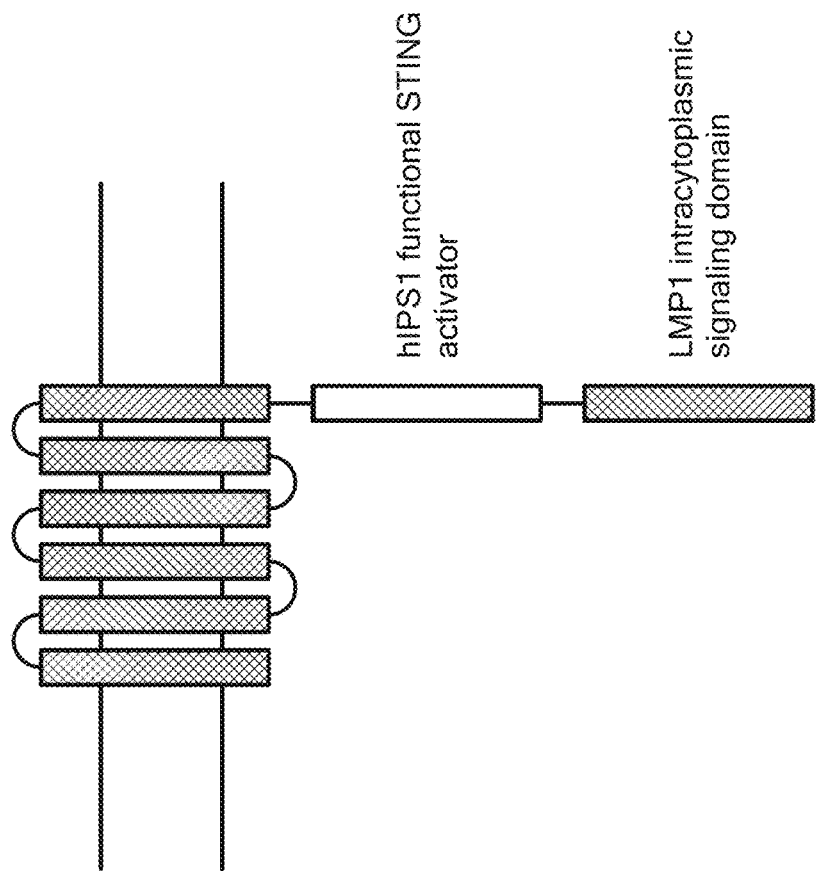
FIGS. 9A and 9B show single molecule adjuvant embodiments of the technology.
Figure 9A:
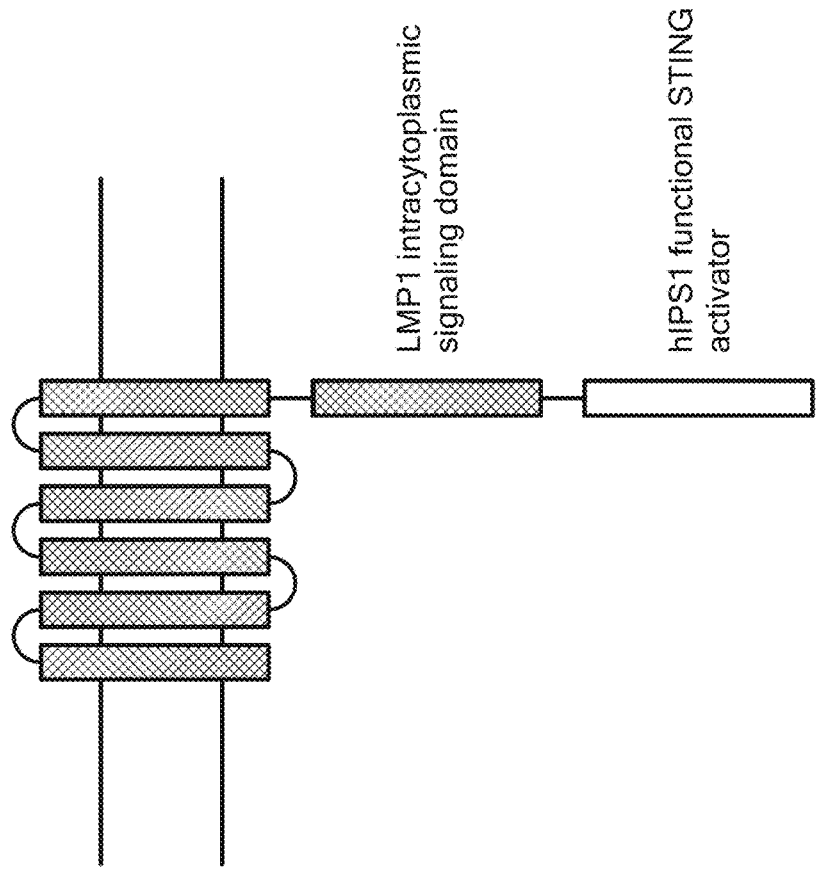
Figure 10:
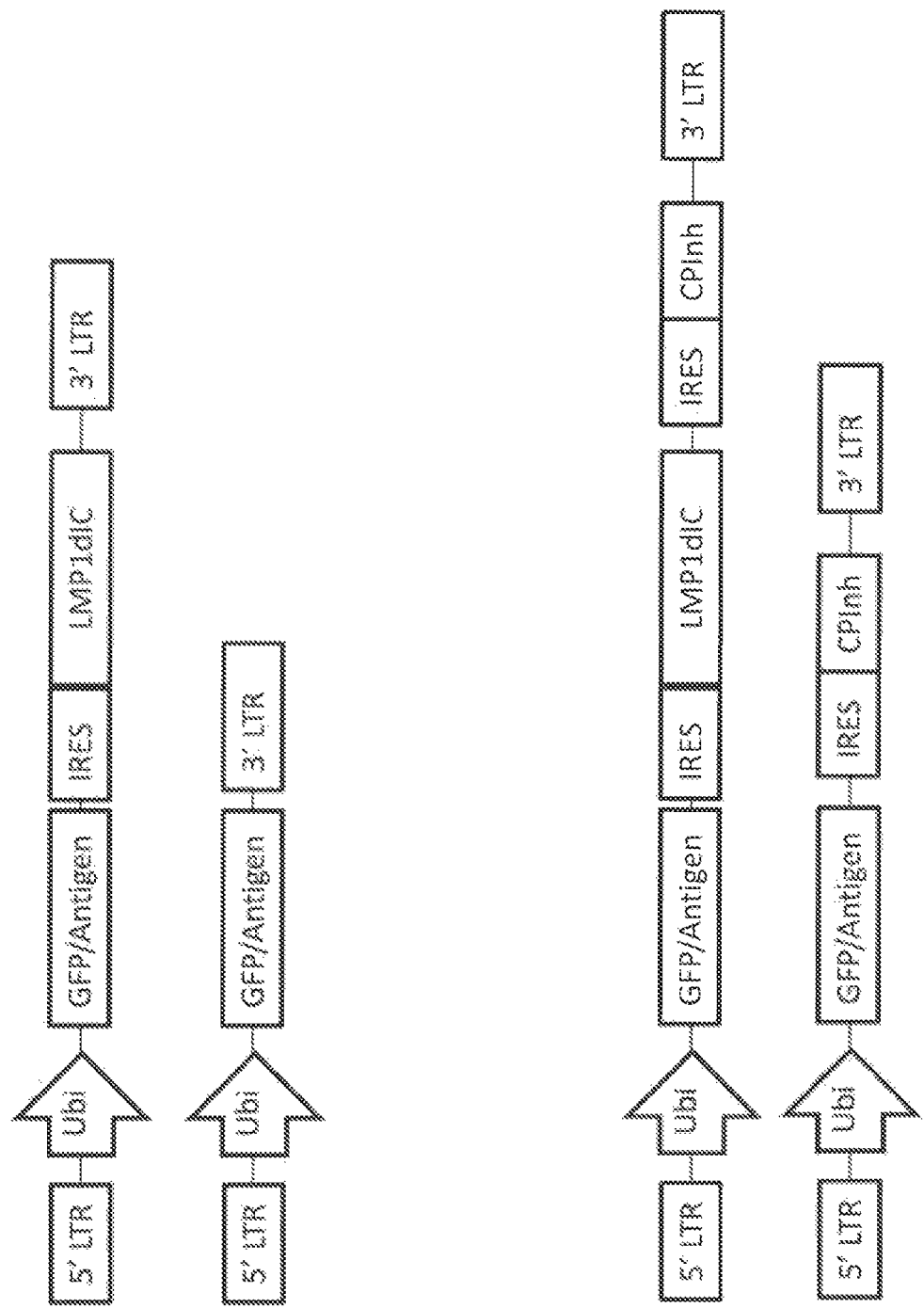
FIG. 10 shows viral vector constructs featuring a single molecule adjuvant.

See FIGS. 8A-8B for illustrations of the adjuvant constructs and FIG. 10 for the control constructs.

Dendritic cell and macrophage proliferation was quantified after 24 h of culture. Triplicate samples were pulsed with $^3$H-TdR and cultured overnight before being harvested and the incorporation of radioactive thymidine determined by standard scintillation counting. Proliferation was slightly reduced with adjuvanted vectors compared to GFP vector, most likely due to the presence of a longer DNA cassette. As already mentioned, viability of the transduced cells was determined by staining with a fixable viability dye before analysis using a BD FACS Canto System flow cytometer. While slight differences were observed between the adjuvanted vectors, no significant toxicity was found.

Figure 11A:
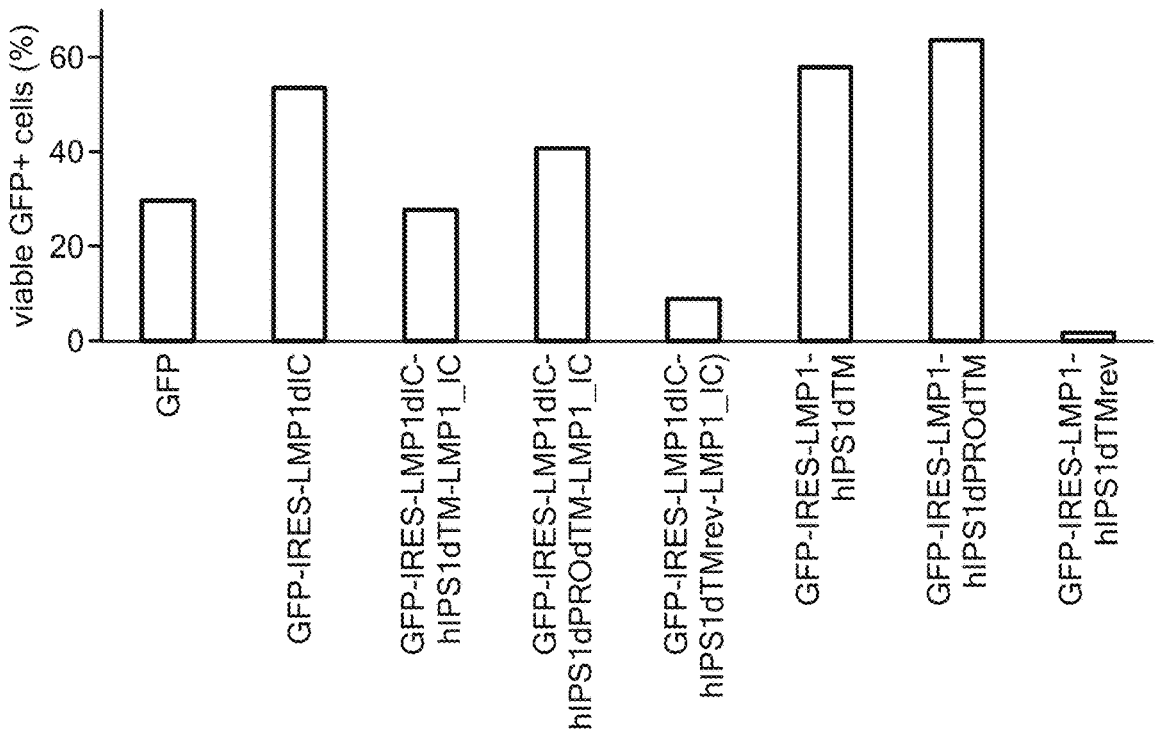
FIG. 11A-11B show the expression levels of GFP transgene in human dendritic cells and macrophages transduced by the lentiviral vectors.
Figure 11B:
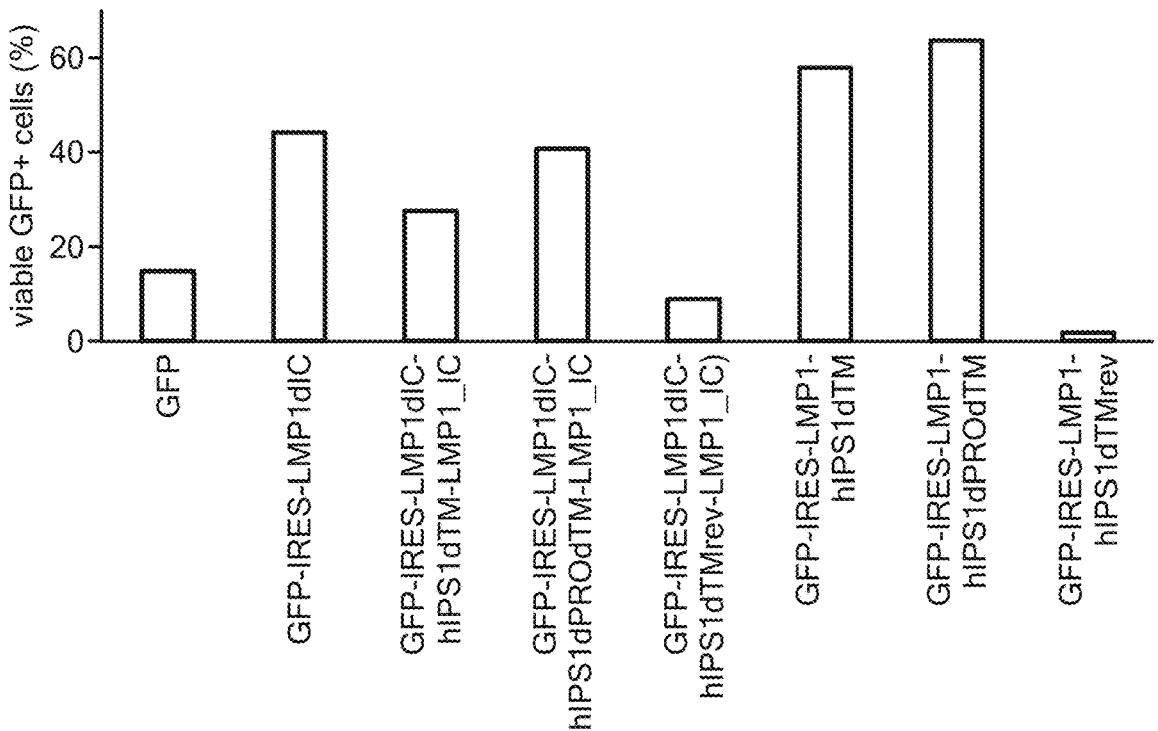

Expression of GFP was determined for cells transduced with each construct by measuring the fluorescence with Attune NxT flow cytometer after 96 h of culture, and the results are shown in FIGS. 11A (dendritic cells) and 11B (macrophages). The percentages of viable and GFP-positive cells were determined by gating on debris excluded/viable/single cells. Three independent experiments were carried out with PBMCs isolated from different donors. Graphed data represent means of duplicates of a representative experiment. The results presented in FIGS. 11A (dendritic cells) and 11B (macrophages) show that, for both cell types, while slight differences were observed between the adjuvanted vectors, significant expression of the GFP transgene was observed with IRES constructions. The removal of Pro domain in constructs resulted in an increased GFP transgene expression with constructs 2 and 5, most likely due to the presence of a shorter DNA cassette. The inversion of the orientation of the IPS1 CARD and PRO domains strongly reduced the expression of GFP transgene as observed with constructs 3 and 6.

Figure 12A:
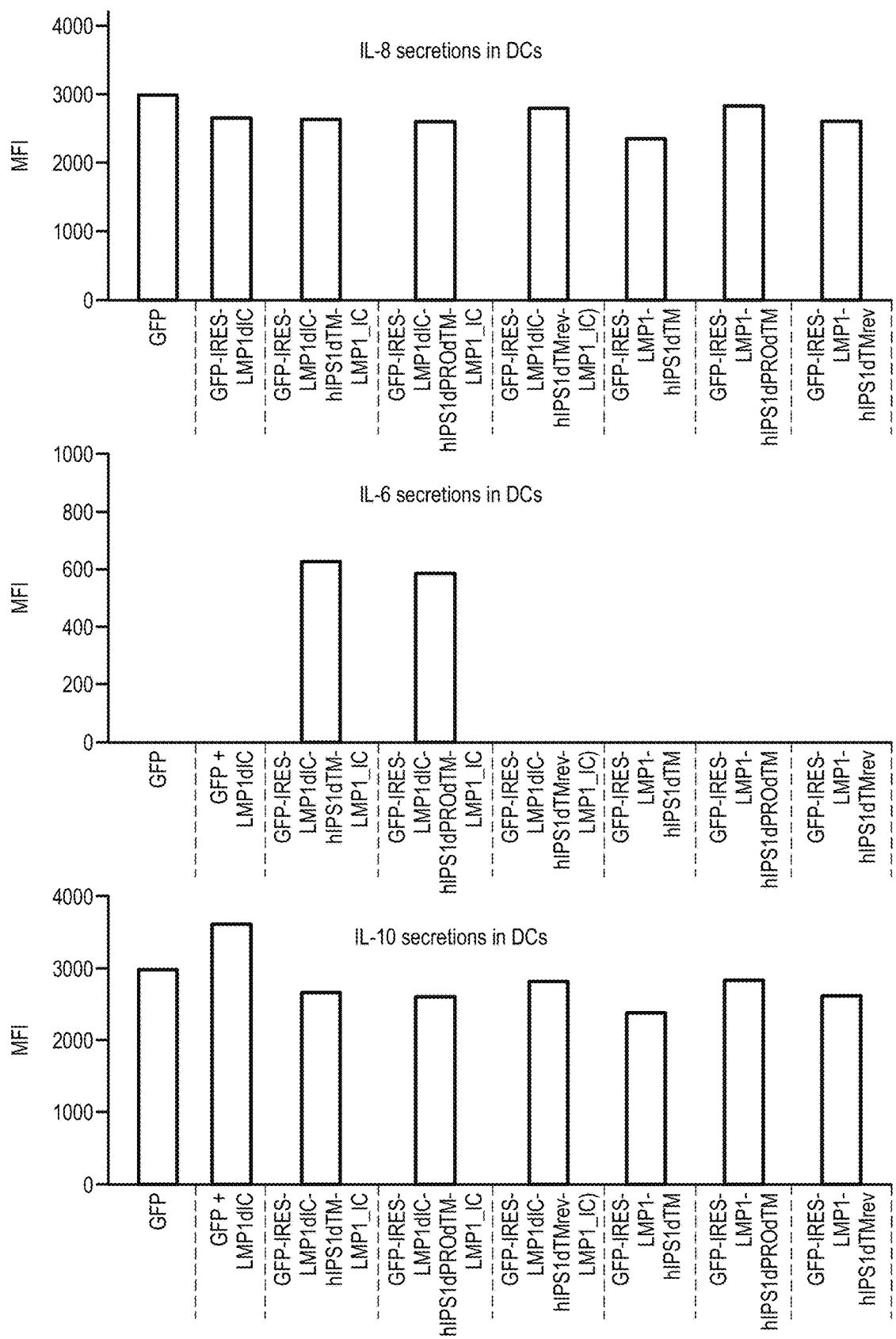
FIGS. 12A-12D show the activation and maturation of human dendritic cells and macrophages induced in vitro by the lentiviral vectors.
Figure 12A:
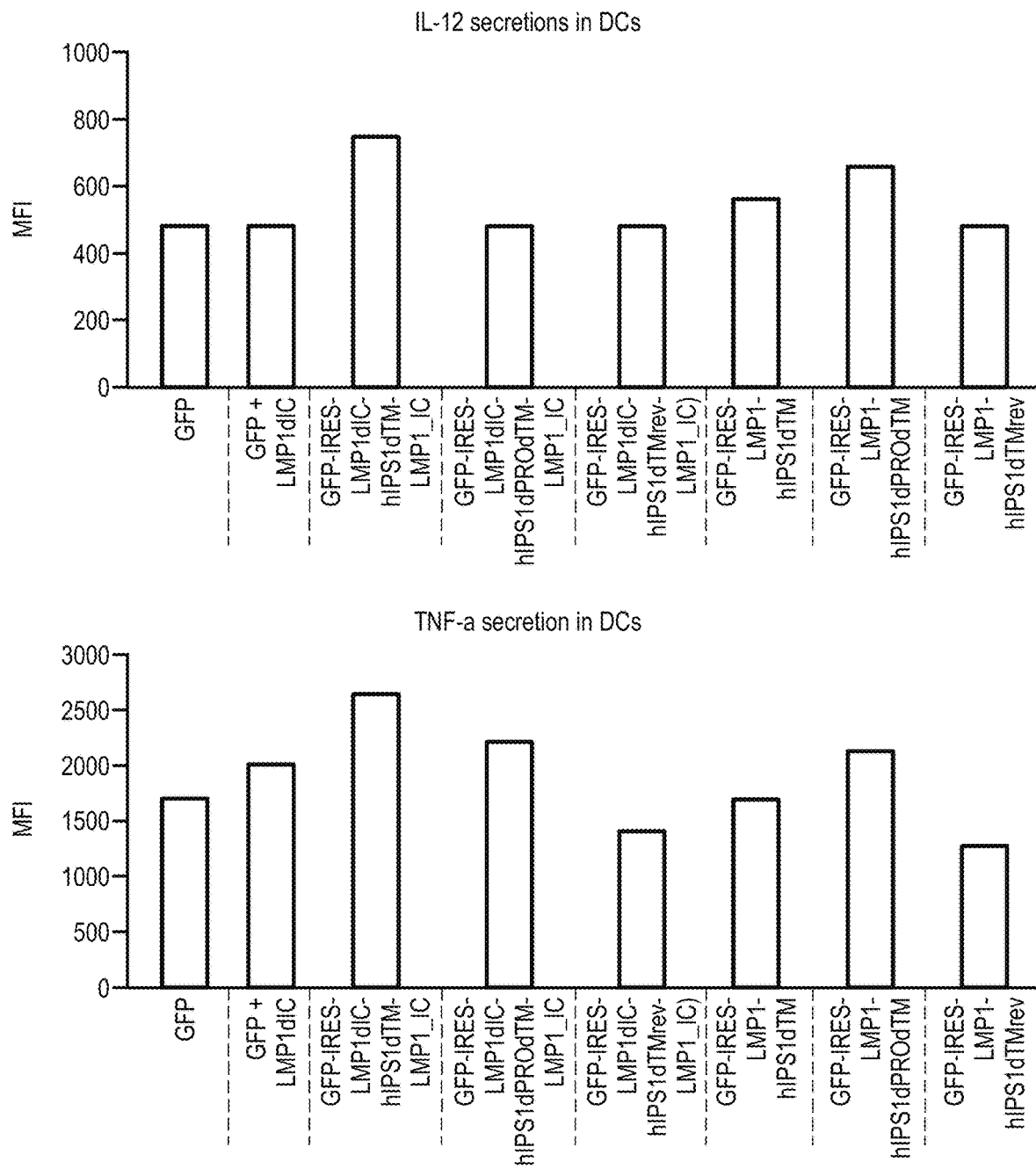
Figure 12B:
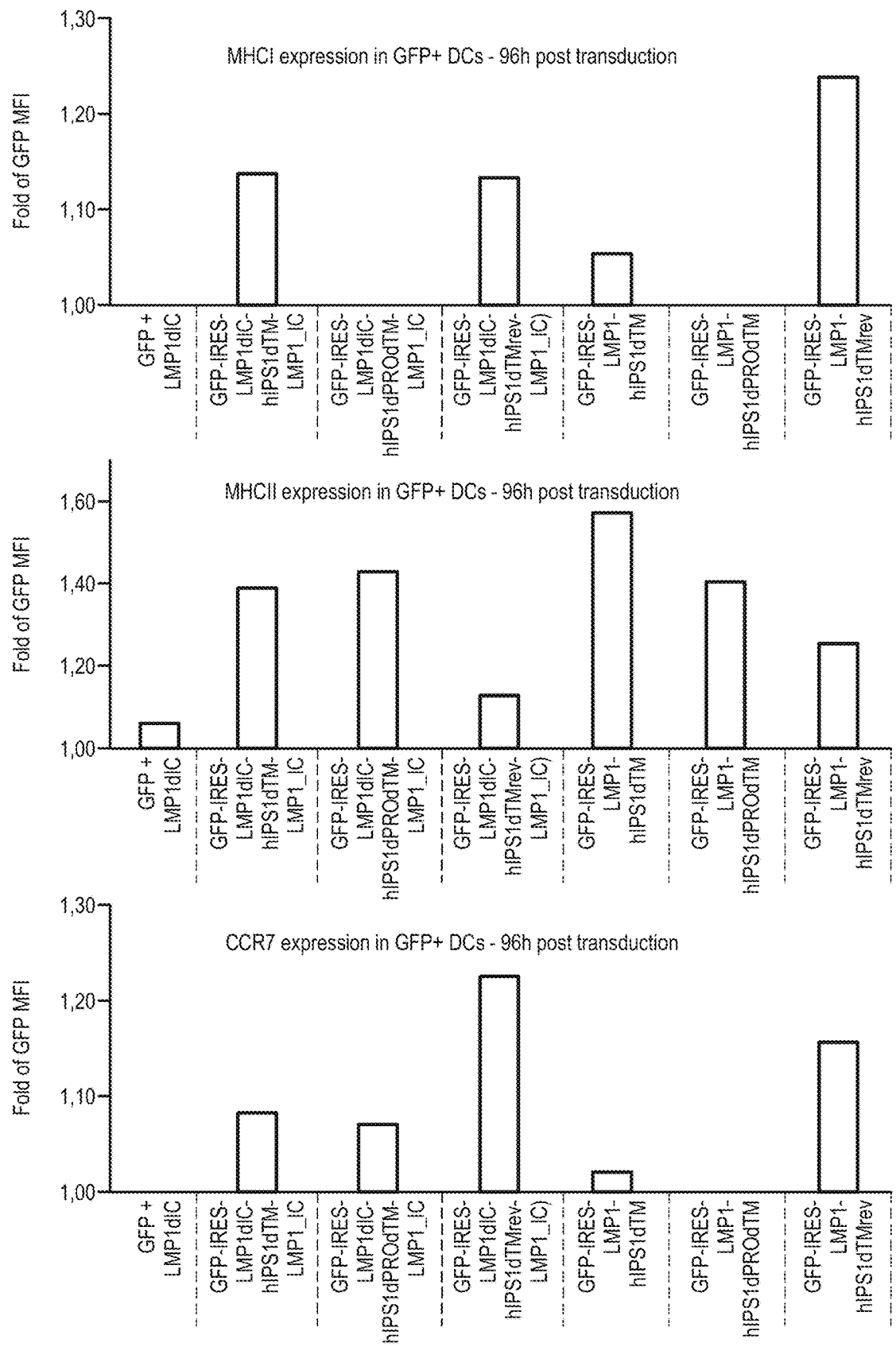
Figure 12B:
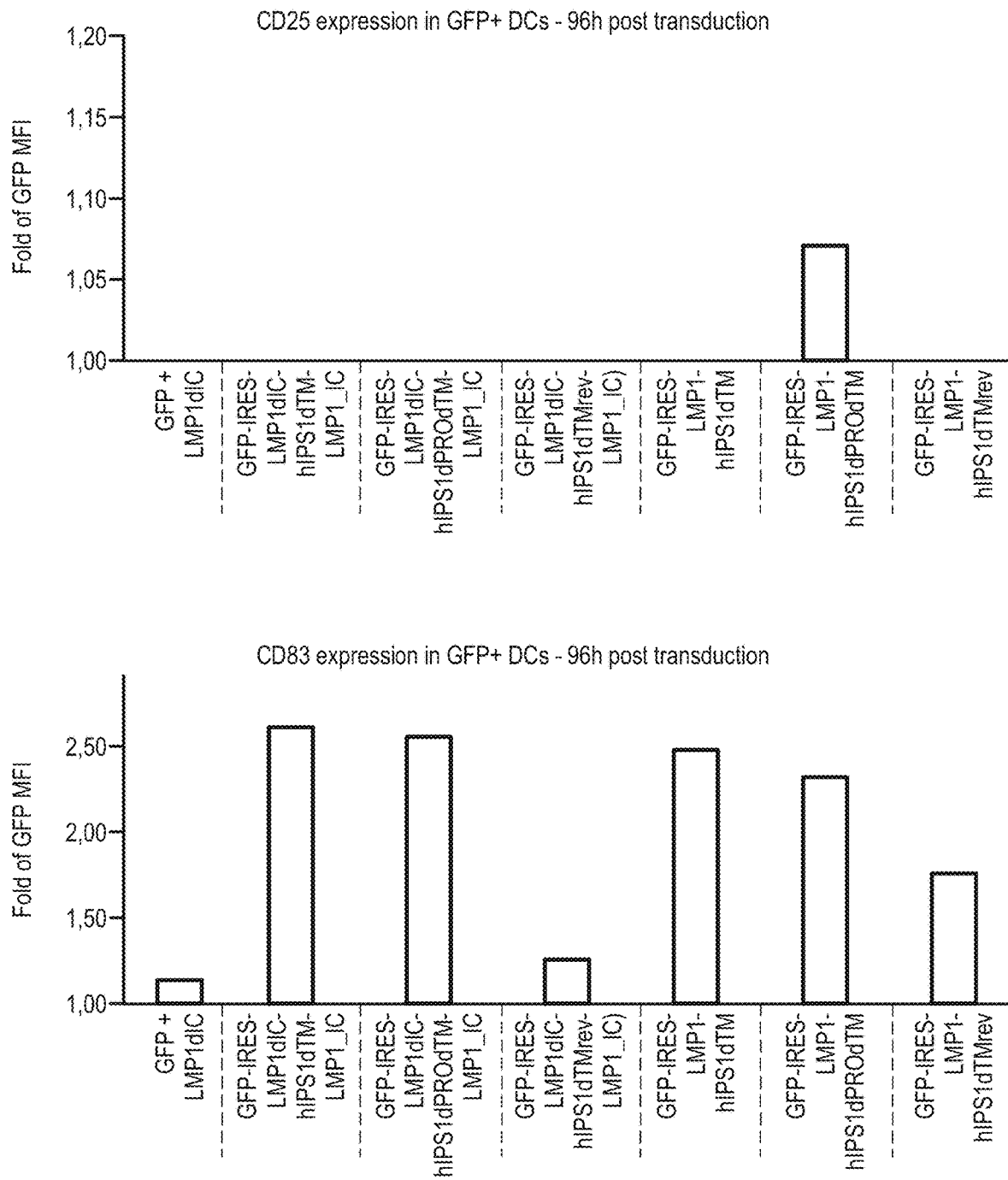
Figure 12B:
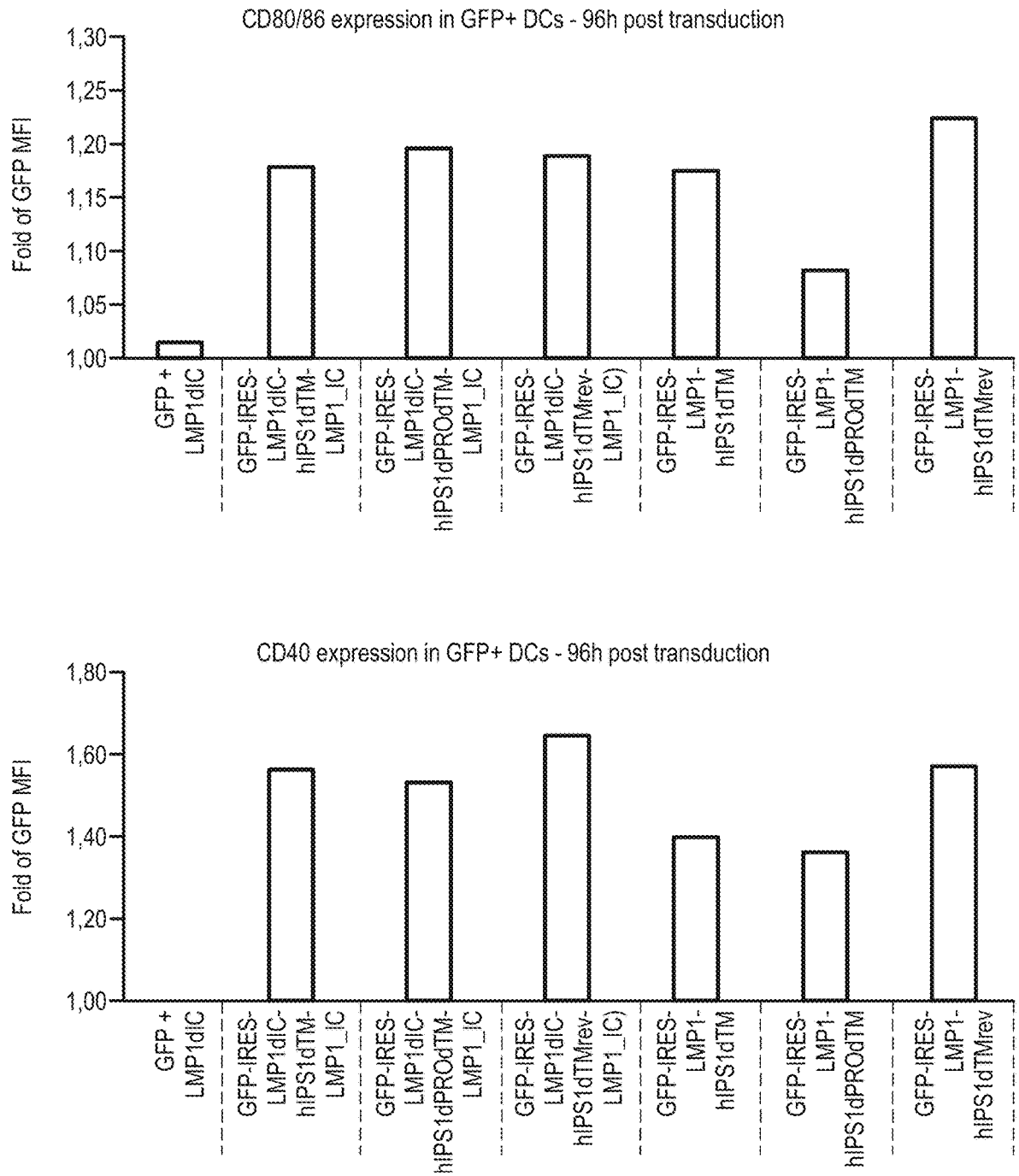
Figure 12C:
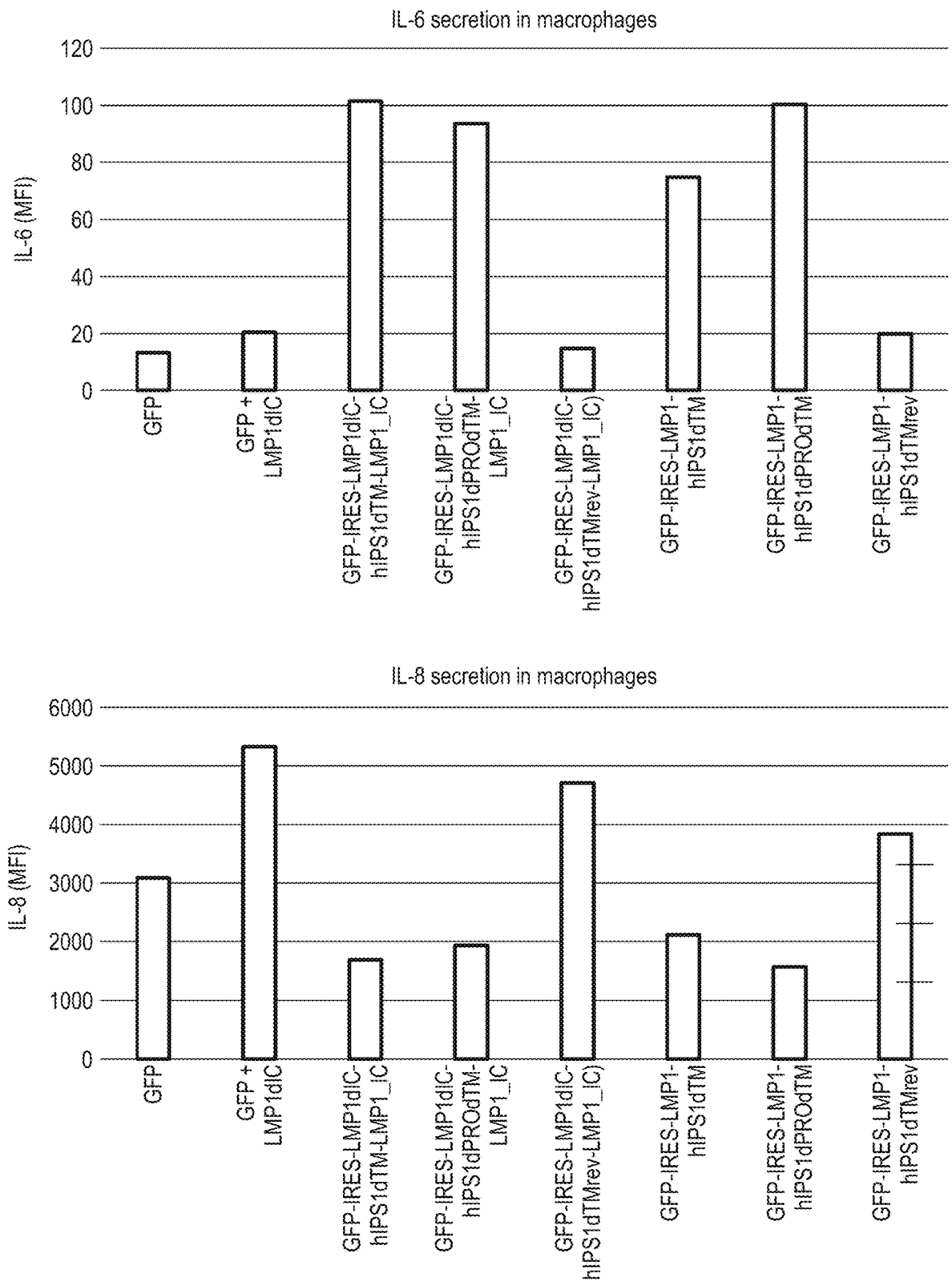
Figure 12C:
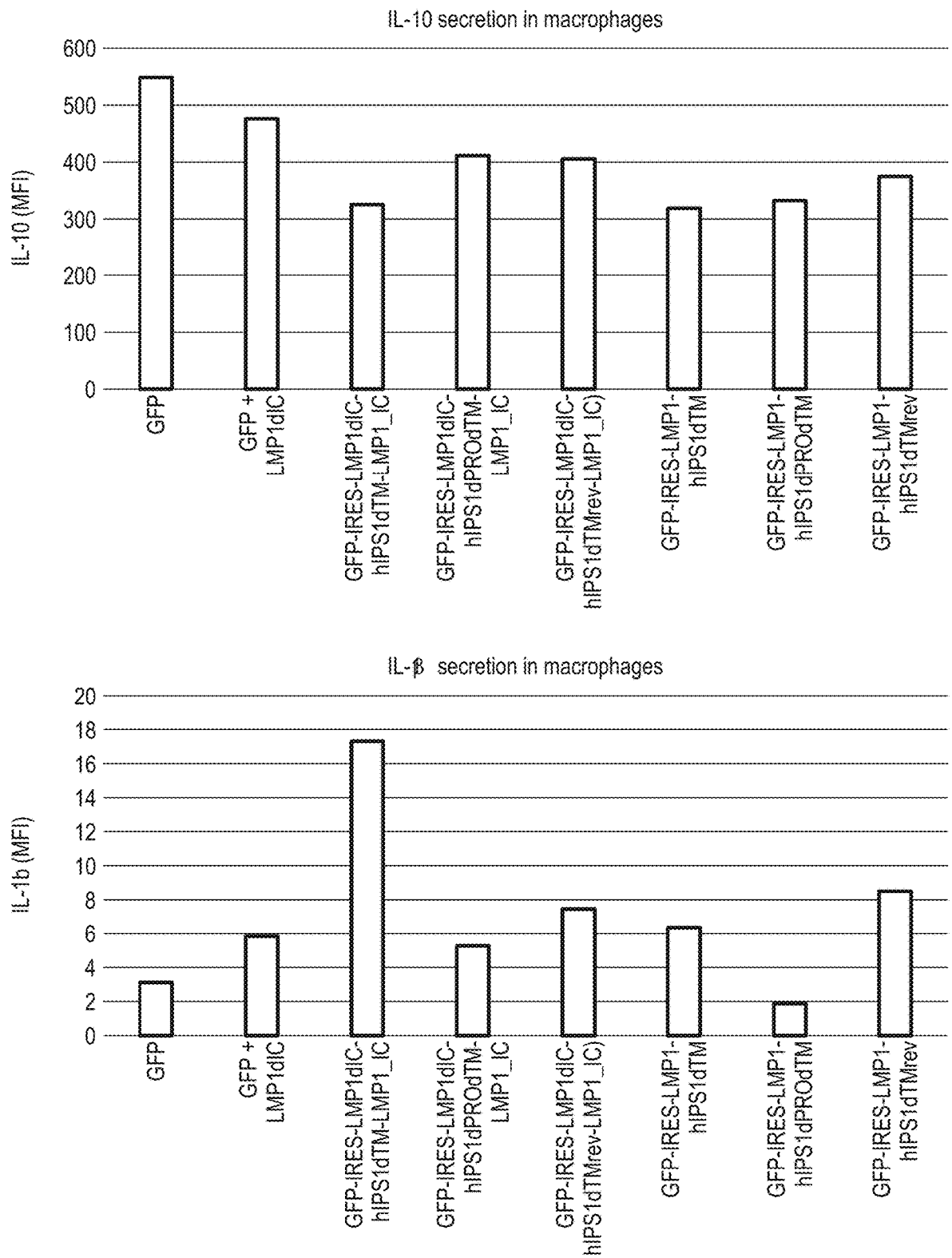
Figure 12C:
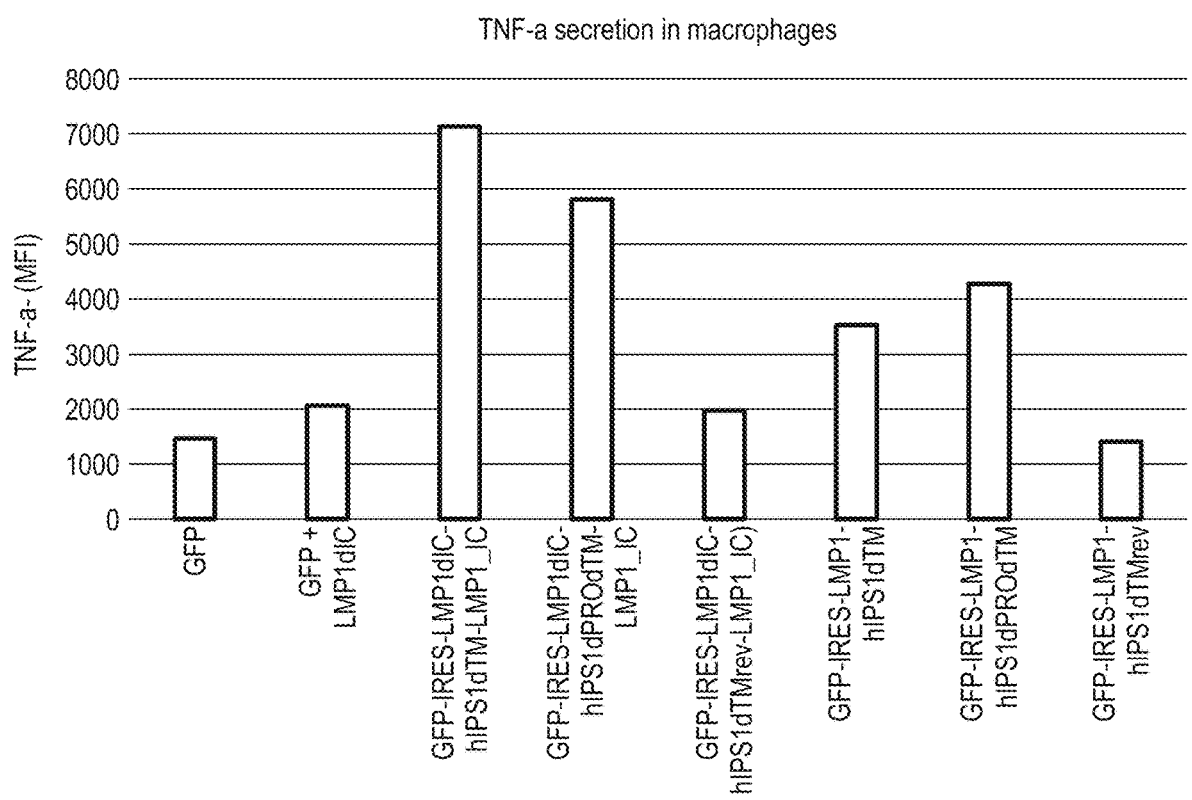
Figure 12D:
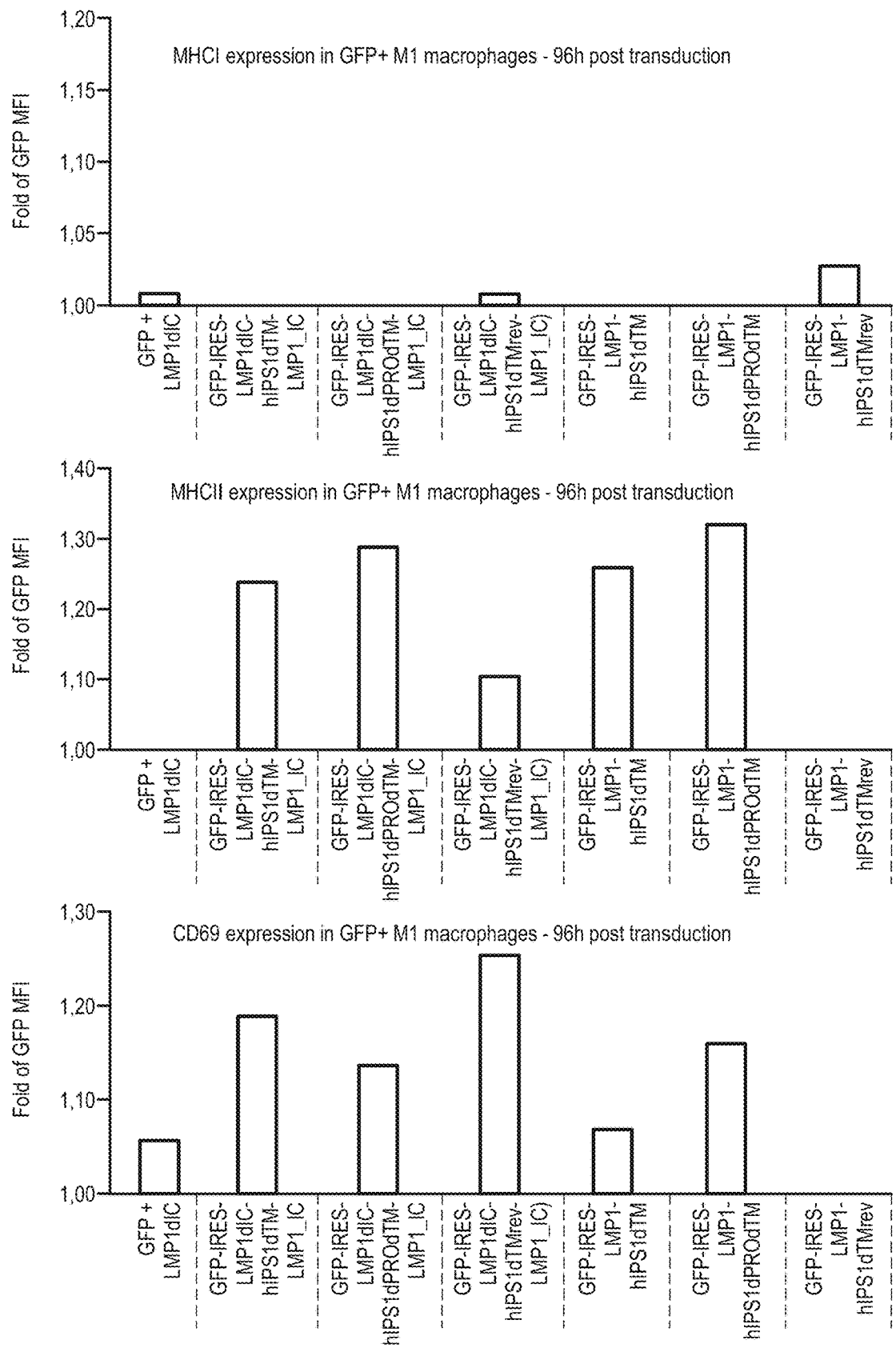
Figure 12D:
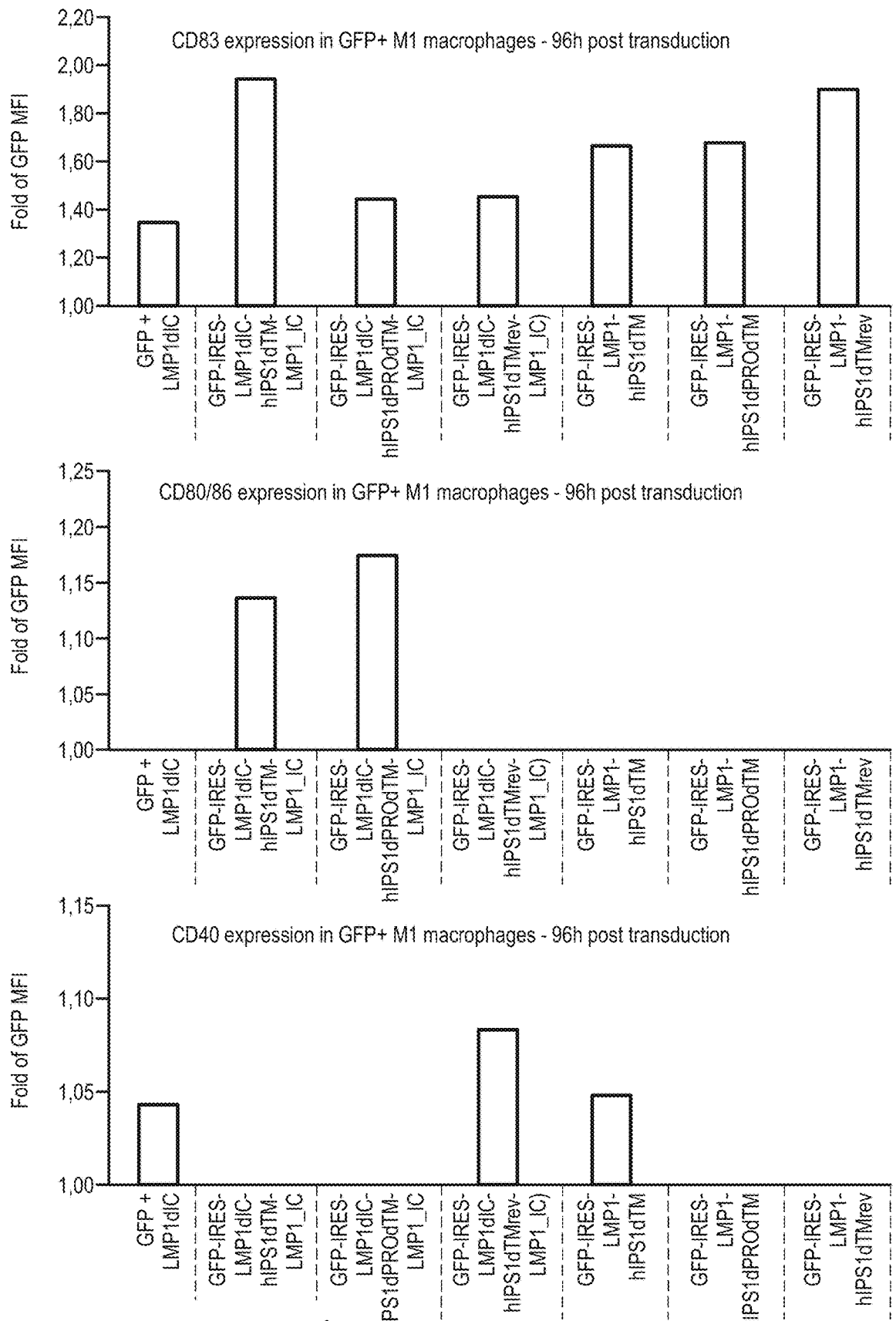

Activation and maturation of the dendritic cells and macrophages elicited by the lentiviral vectors were evaluated by measuring the expression of surface markers and assessing their cytokine and chemokine release profile. To determine levels of lentiviral integration and DC/macrophages activation, cells were harvested after 96 h culture, stained with a fixable viability dye and a panel of staining antibodies recognizing the following surface markers; CD25, CD40, CD69, CD80/86, CD83, CCR7, MHC I and MHC II, before analysis using a BD FACS Canto System flow cytometer. Cell frequencies and Geometric mean (Gmean) marker expression values were determined by gating on debris excluded/viable/single cells. All expression levels were normalized to the expression of GFP. For both dendritic cells and macrophages, activation of the STING and CD40 pathways was assessed by measuring the production of IFN-alpha and IFN-beta, as well as the immune-stimulatory cytokines IL-8, IL-1beta, TNF-alpha, IL-6, and IL-12p70 after 96 h of culture by Luminex analysis with a Bioplex 200 system with high throughput fluidics (Biorad). The production of immune-suppressive cytokine IL-10 was measured as control. Three independent experiments were carried out with PBMCs isolated from different healthy donors. Graphed data represent means of duplicates of a representative experiment. The results are presented in FIGS. 12A (dendritic cells, cytokines), 12B (dendritic cells, membrane markers), 12C (macrophages, cytokines), and 12D (macrophages, membrane markers).

For transduced dendritic cells, the results for expression of surface markers by GFP positive cells showed that IRES constructs upregulated the expression of the following immune activation markers: MHCII (upregulation observed with constructs 1, 2, 4 and 5); CD40 (significant increase with constructs 1, 2, 3, and 6); CD83 (2-fold increase with constructs 1, 3, 4, and 5), CD80/86 (slight upregulation with constructs 1, 2, 3, 4, and 6). Consistent with the upregulation of these activation markers, increases in cytokine expression were as follows: pro-inflammatory IL-6 was expressed with constructs 1 and 2; pro-inflammatory TNF-alpha significantly increased significantly with constructs 1, 2, and 5; IL-12 significantly increased with constructs 1 and 5. Anti-inflammatory IL-10 levels were not affected by any of the evaluated constructs.

Similarly, in transduced macrophages, the results for expression of markers by GFP-positive cells showed that the IRES constructs upregulated the expression of immune activation markers: MHCII was induced by constructs 1, 2, 4 and 5; CD83 increased 2-fold with constructs 1 and 6; and CD80/86 increased with constructs 1 and 2. Consistent with the upregulation of these activation markers, increases in cytokine expression were as follows: pro-inflammatory IL-1beta increased by a 4-fold factor with construct 1 and to a lower extant with constructs 3, 4 and 6; a significant increase of pro-inflammatory IL-6 levels with constructs 1, 2, 4 and 5; and a 4-fold increase in pro-inflammatory TNF-alpha with constructs 1 and 2. Anti-inflammatory IL-10 levels were not affected by any of the evaluated constructs.

In conclusion, the removal of the IPS1 transmembrane domain while reversing the orientation of the IPS1 CARD and PRO domains did not show any immune stimulatory effect. Removal of the IPS1 transmembrane domain increased the activity of the adjuvant while the orientation of LMP1 and IPS1 did not have a significant impact on the adjuvant effect by IRES constructs.

Example 4. In Vivo Immunogenicity in Healthy Mice Treated with Single or Multiple Antigens Shows Superior Immunogenicity Using Double Adjuvanted LMP1-IPS1 (CD40L and STING) Lentiviral Vectors Healthy mice are treated with different with viral vectors containing expression cassettes as described in Example 1. Experiments are performed to compare the immune response when the antigen and adjuvants (i.e., CD40L and STING pathways) are expressed alone or together after two administrations (prime+boost). Short-(3 weeks) and long-term (3 months) evaluation of in vivo immunogenicity is conducted by FACS analysis of mouse blood biomarkers (IFN-gamma and various interleukins), which allows for the detection and quantification of antigen-specific immune cells such as $CD4^+$, and $CD8^+$, and memory T cells targeting the antigen present into the vector. Treatment with double adjuvanted lentiviral vector coding for an antigen(s) and LMP1-IPS1 fusions is expected to increase specific immunogenicity when compared to single adjuvanted lentiviral vectors, or expressing only the membrane domain of LMP1.

Example 5. In Vivo Immunogenicity in Mouse Models of Specific Tumors Shows Superior Effectiveness of Double Adjuvanted Lentiviral Vectors Containing a Combination of Multiple Antigens and CD40L and STING Pathway Activators Mouse models of specific tumors are treated with viral vectors containing expression cassettes as described in Example 1. Mice are divided into different treatment groups according to vector type and construct, dose and number of injections (prime+boost injections). In vivo efficacy and immunogenicity is evaluated by tumor growth rates, survival, and detection of antigen specific as $CD4^+$, $CD8^+$ and memory T cells by FACS analysis of mouse blood biomarkers (IFN-gamma and various interleukins). Double adjuvanted lentiviral vectors encoding indication-specific antigens are expected to induce the most potent and long-lasting immune response of all experimental groups, thus inducing a higher survival rate and/or lower tumor growth in the treated groups of mice.

Example 6. In Vivo Immunogenicity in Mouse Models of Specific Anticheckpoint Sensitive Tumors Shows Superior Effectiveness of Double Adjuvanted Lentiviral Vectors Containing a Combination of Multiple Antigens and Anticheckpoint Mouse models of specific tumors are treated with viral vectors containing expression cassettes as described in Example 1 and a soluble and secreted form of one or more anticheckpoint molecules. Mice are divided into different treatment groups according to vector constructs, dose, and number of injections (prime+boost injections). In vivo efficacy and immunogenicity is evaluated by tumor growth rates, survival, and detection of antigen specific as $CD4^+$, $CD8^+$ and memory T cells by FACS analysis of mouse blood biomarkers (IFN-gamma and various interleukins). Double adjuvanted Lentiviral vectors encoding indication-specific antigen and anti-checkpoint molecules are expected to induce the most potent and long-lasting immune response of all experimental groups.

This application claims priority to U.S. Provisional Appl. No. 62/426,860, filed 28 Nov. 2016, which is hereby incorporated by reference in its entirety.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

REFERENCES

Barry, M. et al. Role of endogenous endonucleases and tissue site in transfection and CpG-mediated immune activation after naked DNA injection Hum Gene Ther, 10 (15) (1999), pp. 2461-2480

McNamara, M. et al. RNA-Based Vaccines in Cancer Immunotherapy. J Immunol Res. 2015; 2015: 794528.

Nasri et al., Production, Purification and Titration of a Lentivirus-Based Vector for Gene Delivery Purposes, Cytotechnology 66, 1031-8 (2014).

The content of the ASCII text file of the sequence listing named Sequence-Listing-12268-0303, having a size of 108 kb and a creation date of 4 Feb. 2020, and electronically submitted via EFS-Web on 4 Feb. 2020, is incorporated herein by reference in its entirety.

What is claimed is:

1. A viral vector comprising a first nucleic acid sequence encoding an antigen or an antigenic epitope, a second nucleic acid sequence encoding a full length latent membrane protein 1 (LMP1) of Epstein Barr virus, and a third nucleic acid sequence encoding a fusion protein comprising the transmembrane portion of LMP1 in which the intracytoplasmic domain has been replaced by human IPS1, wherein the encoded sequences of the vector are codon optimized for human expression, and wherein the second and third nucleic acid sequences follow the first nucleic acid sequence in any order, and wherein the vector further comprises a nucleic acid sequence encoding a soluble immune checkpoint inhibitor molecule selected from the group consisting of CTLA-4, PD-1, PDL-1, LAG-3, TIM 3, B7-H3, ICOS, IDO, CD47, B7-H4, TIGIT, CD160, and combinations thereof.

2. The viral vector of claim 1, wherein the vector is a lentiviral vector.

3. The viral vector of claim 1, wherein the first nucleic acid sequence encodes a fusion protein comprising two or more antigens or two or more antigenic epitopes.

4. The viral vector of claim 1, wherein the second nucleic acid sequence of claim 1, or the third nucleic acid sequence of claim 1, comprises a sequence selected from the group consisting of SEQ ID NO. 1, SEQ ID NO:3, SEQ ID NO:5, SEQ ID NO:7, SEQ ID NO:9, SEQ ID NO:11, SEQ ID NO:19, SEQ ID NO:21 and SEQ ID NO:23.

5. The viral vector of claim 1, wherein the vector further comprises a functional lentiviral integrase protein, wherein the vector is self-inactivating.

6. The viral vector of claim 1, wherein the antigen is selected from the group consisting of NY-ESO-1, mesothelin, PSA, MART-1, MART-2, Gp100, tyrosinase, p53, ras, MUC1, SAP-1, survivin, CEA, Ep-CAM, Her2, BRCA1/2, gag, reverse transcriptase, tat, circumsporozoite protein, HCV nonstructural proteins, hemaglutinins, and combinations thereof.

7. An immunotherapeutic formulation for treating cancer or infection in a subject, the formulation comprising the viral vector of claim 1.

8. A method of inducing or enhancing an immune response against a cancer or an infectious disease in a subject, the method comprising administering the viral vector of claim 1 to a subject in need thereof, whereby an immune response against said cancer or infectious disease is induced or enhanced in the subject.

9. The method of claim 8, whereby an immune response is induced or enhanced against a cancer, and the cancer is selected from the group consisting of: melanoma, glioma, prostate cancer, breast cancer, cervical cancer, colorectal cancer, kidney cancer, lung cancer, lymphoma and pancreatic cancer.

10. The method of claim 8, whereby an immune response is induced or enhanced against an infectious disease, and the infectious disease is selected from the group consisting of: HIV/AIDS, hepatitis C, HPV, pneumonia, influenza, malaria, leishmaniosis, tuberculosis, Hansen's disease, rabies, dengue, Zika, Ebola, and schistosomiasis.

* * * * *